US006297048B1

(12) United States Patent
Jolly et al.

(10) Patent No.: US 6,297,048 B1
(45) Date of Patent: Oct. 2, 2001

(54) HEPATITIS THERAPEUTICS

(75) Inventors: Douglas J. Jolly, Leucadia; Stephen M. W. Chang, Poway; William T. L. Lee, Carlsbad; Kay Townsend, Encinitas; Joanne O'Dea, La Jolla, all of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 08/483,511

(22) Filed: Jun. 7, 1995

Related U.S. Application Data

(63) Continuation-in-part of application No. 08/374,414, filed on Jan. 19, 1995, now abandoned, which is a continuation-in-part of application No. 08/286,829, filed on Aug. 5, 1994, now abandoned, which is a continuation-in-part of application No. 08/102,132, filed on Aug. 4, 1993, now abandoned, which is a continuation-in-part of application No. 08/032,385, filed on Mar. 17, 1993, now abandoned, which is a continuation-in-part of application No. 07/830,417, filed on Feb. 4, 1992, now abandoned.

(51) Int. Cl.$^7$ .............................. C12N 15/63; C12P 21/02
(52) U.S. Cl. ........................................ 435/320.1; 435/69.3
(58) Field of Search .................................. 435/69.1, 69.3, 435/320.1; 424/228.1

(56) References Cited

U.S. PATENT DOCUMENTS

| 4,547,368 | * 10/1985 | Tabor et al. . | |
| 4,696,898 | 9/1987 | Fitts et al. ............................ | 435/69.3 |
| 4,710,463 | 12/1987 | Murray ................................. | 435/69.3 |

(List continued on next page.)

FOREIGN PATENT DOCUMENTS

| 241 021 A2 | 10/1987 | (EP) . |
| 243 204 A2 | 10/1987 | (EP) . |
| 278 940 A2 | 8/1988 | (EP) . |

(List continued on next page.)

OTHER PUBLICATIONS

Bachmann et al. (1994) In Vivo versus in vitro assays for assessment of T– and B– cell function. Curr. Opin. Immunol. 6:320–326.*
Koshy et al. (1996) Evaluation of hepatitis C virus protein epitopes for vaccine development. Trends Biotechnol. 14: 364–369, Oct. 1996.*
Verma et al. (1997) Gene therapy–promises, problems and prospects. Nature 389:239–242.*
Eck et al. In "Goodman & Gilman's The Pharmacological Basis of Therapeutics" McGraw–Hill, New York, 1995, pp. 77–101.*

Paoletti et al. (1984) Construction of live vaccines using genetically engineered poxviruses: biological activity of vaccinia virus recombinants expressing the hepatitis B virus surface antigen and the herpes simplex virus glycoprotein D. Proc. Natl. Acad, Jan. 1984.*
Shih et al. (1984) Expression of hepatitis B virus S gene by herpes simplex virus type 1 vectors carrying alpha– and beta–regulated gene chimeras. Proc. Natl. Acad. Sci. USA 81:5867–5870, Sep. 1984.*
Davis et al. (1985) Expression of hepatitis B surface antigen with a recombinant adenovirus. Proc. Natl. Acad. Sci. USA 82:7560–7564, Jan. 1984.*
Cheng et al., "Expression of hepatitis B virus C gene with different length of pre–core sequence by recombinant vaccinia viruses," *Chemical Abstracts* 115(23): Abstract No. 249504, pp. 225, 1991.
Jean–Jean et al., "Expression Mechanism of the Hepatitis B Virus (HBV) C Gene and Biosynthesis of HBe Antigen," *Virology 170:* 99–106, 1989.
Raney et al., "Retroviral–Mediated Transfer and Expression of Hepatitis B e Antigen in Human Primary Skin Fibroblasts and Epstein–Barr Virus–Transformed B Lymphocytes," *Virology 168:* 31–39, 1989.
Ye et al., "Co–expression of hepatitis B virus antigens by a non–defective adenovirus vaccine vectors," *Archives of Virology* 118(1/2): 11–27, 1991.
Moriarty et al., "Expression of the hepatitis B virus surface antigen gene in cell culture by using a simian virus 40 vector," *Proc. Natl. Acad. Sci. USA 78:* 2606–2610, 1981.
Eddleston, A., "Overview of HBV Pathogenesis," in *Viral Hepatitis and Liver Disease,* 1991, pp. 234–237.
Penna et al., "Cytotoxic T Lymphocytes Recognize an HLA–A2–restricted Epitope within the Hepatitis B Virus Nucleocapsid Antigen," *Journal of Experimental Medicine 174:* 1565–1570, 1991.
Vitiello et al., "Enhancement of Peptide Immunogenicity for CTL Induction By Linkage to a T Helper Peptide," in *Molecular Biology of Hepatitis B Virus Symposia,* p. 135, 1992.
Ishikawa et al., "Relative immunogenicity of hepatitis B virus–encoded antigens as targets for cytotoxic T–cell response," *Immunology 80:* 313–318, 1993.

(List continued on next page.)

*Primary Examiner*—Robert A. Schwartzman
(74) *Attorney, Agent, or Firm*—Robert P. Blackburn; David McMasters; Anne S. Dollard

(57) ABSTRACT

The present invention provides methods of treating hepatitis C infections comprising the step of administering a vector construct which directs the expression of at least one immunogenic portion of a hepatitis C antigen, such that an immune response is generated. Also provided are vector constructs which direct the expression of at least one portion of a hepatitis C antigen, as well as recombinant viruses which carry such vector constructs.

7 Claims, 17 Drawing Sheets

U.S. PATENT DOCUMENTS

| | | | |
|---|---|---|---|
| 4,777,240 | * 10/1988 | Moriarty et al. | |
| 4,868,116 | 9/1989 | Morgan et al. | 435/456 |
| 4,980,289 | 12/1990 | Temin et al. | 435/235.1 |
| 5,024,938 | 6/1991 | Nozaki et al. | 435/68.1 |
| 5,298,394 | * 3/1994 | Arima et al. | 435/7.1 |
| 5,670,153 | * 9/1997 | Weiner et al. | 424/189.1 |

FOREIGN PATENT DOCUMENTS

| | | |
|---|---|---|
| 2223755 A | 4/1990 | (GB). |
| WO 88/00971 | * 2/1988 | (WO). |
| WO 88/06185 | 8/1988 | (WO). |
| WO 88/10301 | 12/1988 | (WO). |
| WO 89/02468 | 3/1989 | (WO). |
| WO 89/05349 | 6/1989 | (WO). |
| WO 90/11092 | 10/1990 | (WO). |
| WO 93/15207 | 8/1993 | (WO). |

OTHER PUBLICATIONS

Warner et al., "Induction of HIV–Specific CTL and Antibody Responses in Mice Using Retroviral Vector–Transduced Cells," *Aids Research and Human Retroviruses* 7(8): 645–655, 1991.

Mosmann and Coffman, "Two types of mouse helper T–cell clone. Implications for immune regulation," *Immunology Today* 8(7/8): 223–227, 1987.

Maruyama et al., "The Serology of Chronic Hepatitis B Infection Revisited," *Journal of Clinical Investigation* 91: 2586–2595, 1993.

Clerici et al., "Restoration of HIV–Specific Cell–Mediated Immune Responses by Interleukin–12 in Vitro," *Science* 262: 1721–1724, 1993.

Wolf et al., "Cloning of cDNA for Natural Killer Cell Stimulatory Factor, A Heterodimeric Cytokine with Multiple Biologic Effects on T and Natural Killer Cells," *Journal of Immunology* 146(9): 3074–3081, 1991.

Kuo et al., "An Assay for Circulating Antibodies to a Major Etiologic Virus of Human Non–A, Non–B Hepatitis," *Science* 244: 362–364, 1989.

Choo et al., "Genetic organization and diversity of the hepatitis C virus," *Proc. Natl. Acad. Sci. USA* 88: 2451–2455, 1991.

Al–Sumidaie et al., "Particles with properties of retroviruses in monocytes from patients with breast cancer," *The Lancet* 1:5–9, 1988.

Allison and Byars, "Development of an Adjuvant Formulation That Can Elicit Protective Immunity against Retroviruses," in *Vaccine 87*, Cold Spring Harbor Laboratory, 1987, pp. 56–59.

Alter, H., "Transfusion–Associated Non–A, Non–B Hepatitis: The First Decade," in *Viral Hepatitis and Liver Disease*, Alan R. Liss, Inc., New York, 1988, pp. 537–542.

Altmann et al., "Cotransfection of ICAM–1 and HLA–DR reconstitutes human antigen–presenting cell function in mouse L cells," *Nature* 338: 512–514, 1989.

Anderson, W.F., "Prospects for Human Gene Therapy," *Science* 226: 401–409, 1984.

Acsadi et al., "Human dystrophin expression in mdx mice after intramuscular injection of DNA constructs," *Nature* 352: 815–818, 1991.

Ballay et al., "In vitro and in vivo synthesis of the hepatitis B virus surface antigen and of the receptor for polymerized human serum albumin from recombinant human adenoviruses," *EMBO Journal* 4(13B): 3861–3865, 1985.

Bancroft et al., "Detection of Additional Antigenic Determinants of Hepatitis B Antigen," *Journal of Immunology* 109(4): 842–848, 1972.

Bass et al., "Heterogeneous Mechanisms of Human Cytotoxic T Lymphocyte Generation. I. Differential Helper Cell Requirement for the Generation of Cytotoxic Effector Cells from $CD8^+$ Precursor Subpopulations," *Journal of Immunology* 149: 2489–2495, 1992.

Berkner, K., "Development of Adenovirus Vectors for the Expression of Heterologous Genes," *BioTechniques* 6(7): 616–624, 1988.

Berman et al., "Expression and Immunogenicity of the Extracellular Domain of the Human Immunodeficiency Virus Type 1 Envelope Glycoprotein, gp160," *Journal of Virology* 63(8): 3489–3498, 1989.

Blum et al., "The molecular biology of hepatitis B virus," *Trends in Genetics* 5(5): 154–158, 1989.

Brakenhoff et al., "Molecular Cloning and Expression of Hybridoma Growth Factor in *Escherichia coli*," *Journal of Immunology* 139(12): 4116–4121, 1987.

Burrell et al., "Expression in *Escherichia coli* of hepatitis B virus DNA sequences cloned in plasmid pBR322," *Nature* 279:43–47, 1979.

Chanock et al., "Immunization by Selective Infection With Type 4 Adenovirus Grown in Human Diploid Tissue Culture. I. Safety and Lack of Oncogenicity and Tests for Potency i Volunteers," *JAMA* 195(6): 151–158, 1966.

Choo et al., "Hepatitis C virus: The major causative agent of viral non–A, non–B hepatitis," *British Medical Bulletin* 46(2): 423–441, 1990.

Choo et al., "Isolation of a cDNA Clone Derived from a Blood–Borne Non–A, Non–B Viral Hepatitis Genome," *Science* 244: 359–362, 1989.

Colombo et al., "Prevalence of Antibodies to Hepatitis C Virus in Italian Patients With Hepatocellular Carcinoma," *The Lancet* (Oct. 28): 1006–1008, 1989.

Cristiano et al., "Hepatic gene therapy: Efficient gene delivery and expression in primary hepatocytes utilizing a conjugated adenovirus–DNA complex," *Proc. Natl. Acad. Sci. USA* 90: 11548–11552, 1993.

Curiel et al, "High–Efficiency Gene Transfer Mediated by Adenovirus Coupled to DNA–Polylysine Complexes," *Human Gene Therapy* 3: 147–154, 1992.

Davis et al., "Treatment of Chronic Hepatitis C With Recombinant Interferon Alpha. A Multicenter Randomized Controlled Trial," *New England Journal of Medicine* 321(22): 1501–1506, 1989.

Deres et al., "In vivo priming of virus–specific cytotoxic T lymphocytes with synthetic lipopeptide vaccine," *Nature* 342: 561–564, 1989.

Di Bisceglie et al., "Hepatocellular Carcinoma," *Annals of Internal Medicine* 108: 390–401, 1988.

Di Bisceglie et al., "The Role of Chronic Viral Hepatitis in Hepatocellular Carcinoma in the United States," *American Journal of Gastroenterology* 86(3): 335–338, 1991.

Doefler, W., "Expression of the *Autographa californica* Nuclear Polyhedrosis Virus Genome in Insect Cells: Homologous Viral and Heterologous Vertebrate Genes—The Baculovirus Vector System," *Current Topics in Microbiology and Immunology* 131: 51–68, 1986.

Dubensky et al., "Direct transfection of viral and plasmid DNA into the liver or spleen of mice," *Proc. Natl. Acad. Sci. USA* 81: 7529–7533, 1984.

Ellis and Gerety, "Key Issues in the Selection of an Expression System for Vaccine Antigens," *Journal of Medical Virology 31:* 54–58, 1990.

Evans et al., "An engineered poliovirus chimaera elicits broadly reactive HIV-1 neutralizing antibodies," *Nature 339:* 385–388, 1989.

Faktor and Shaul, "The identification of hepatitis B virus X gene responsive elements reveals functional similarity of X and HTLV–I tax," *Oncogene 5:* 867–872, 1990.

Familletti et al., "A Convenient and Rapid Cytopathic Effect Inhibition Assay for Interferon," *Methods in Enzymology 78:* 387–394, 1981.

Felgner et al., "Lipofection: A highly efficient, lipid–mediated DNA–transfection procedure," *Biochemistry 84:* 7413–7417, 1987.

Finter et al., "The Use of Interferon–α in Virus Infections," *Drugs 42*(5): 749–765, 1991.

Fisher–Hoch et al., "Protection of rhesus monkeys from fatal Lassa fever by vaccination with a recombinant vaccinia virus containing the Lassa virus glycoprotein gene," *Proc. Natl. Acad. Sci. USA 86:* 317–321, 1989.

Flexner et al., "Attenuation and immunogenicity in primates of vaccinia virus recombinants expressing human interleukin–2," *Vaccine 8:*17–21, 1990.

Foguet and Lübbert, "Precise and Efficient Construction of Synthetic Genes," *BioTechniques 13:* 674–675, 1992.

Friedmann, T., "Progress Toward Human Gene Therapy," *Science 244:* 1275–1281, 1989.

Furesz et al., "Tumorigenicity Testing of Various Cell Substrates for Production of Biologicals," *Develop. Biol. Standard. 70:* 233–243, 1989.

Ganem and Varmus, "The Molecular Biology of the Hepatitis B Viruses," *Ann. Rev. Biochem. 56:* 651–693, 1987.

Gansbacher et al., "Interleukin 2 Gene Transfer into Tumor Cells Abrogates Tumorigenicity and Induces Protective Immunity," *Journal of Experimental Medicine 172:* 1217–1224, 1990.

Gansbacher et al., "Retroviral Vector–mediated γ–Interferon Gene Transfer Into Tumor Cells Generates Potent and Long Lasting Antitumor Immunity," *Cancer Research 50:* 7820–7825, 1990.

Giovanella et al., "Development of Invasive Tumors in the "Nude" Mouse After Injection of Cultured Human Melanoma Cells," *Journal Natl. Cancer Inst. 48:* 1531–1533, 1972.

Golumbek et al., "Treatment of Established Renal Cancer By Tumor Cells Engineered to Secrete Interleukin–4," *Science 254:* 713–716, 1991.

Gregoriadis et al., "Liposomes as immunological adjuvants: antigen incorporation studies," *Vaccine 5:* 145–151, 1987.

Griffiths et al., "Induction of High–Titer Neutralizing Antibodies, Using Hybrid Human Immunodeficiency Virus V3–Ty Viruslike Particles in a Clinically Relevant Adjuvant," *Journal of Virology 65*(1): 450–456, 1991.

Hart et al., "Priming of anti–human immunodeficiency virus (HIV) CD8 + cytotoxic T cells in vivo by carrier–free HIV synthetic peptides," *Proc. Natl. Acad. Sci. USA 88:* 9448–9452, 1991.

Hayata et al., "Effects of Interferon on Intrahepatic Human Leukocyte Antigens and Lymphocyte Subsets in Patients with Chronic Hepatitis B and C," *Hepatology 13:* 1022–1028, 1991.

Houghton et al., "Molecular Biology of the Hepatitis C Viruses: Implications for Diagnosis, Development and Control of Viral Disease," *Hepatology 14*(2): 381–388, 1991.

Jacyna and Thomas, "Antiviral therapy: Hepatitis B," *British Medical Bulletin 46*(2): 368–382, 1990.

Jayaraman et al., "Enhancement of In Vivo Cell–Mediated Immune Responses By Three Distinct Cytokines," *Journal of Immunology 144:* 942–951, 1990.

Karupiah et al., "Elevated Natural Killer Cell Responses in Mice Infected With Recombinant Vaccinia Virus Encoding Murine IL–2," *Journal of Immunology 144*(1): 290–298, 1990.

Kato et al., "Molecular cloning of the human hepatitis C virus genome from Japanese patients with non–A, non–B hepatitis," *Proc. Natl. Acad. Sci. USA 87:* 9524–9528, 1990.

Kit, S., "Recombinant–Derived Modified–Live Herpesvirus Vaccines," *Advances in Experimental Medicine and Biology 251:* 219–236, 1989.

Koike et al., "Transgenic mouse model for human gastric carcinoma," *Proc. Natl. Acad. Sci. USA 86:* 5615–5619, 1989.

Le Bouvier, G. L., "The Heterogeneity of Australia Antigen," *Journal of Infectious Diseases 123*(6): 671–675, 1971.

Levenbook et al., "Tumorigenicity testing of primate cell lines in nude mice, muscle organ culture and for colony formation in soft agarose," *Journal of Biological. Standardization 13:* 135–141, 1985.

Linsley et al., "Binding of the B Cell Activation Antigen B7 to CD28 Costimulates T Cell Proliferation and Interleukin 2 mRNA Accumulation," *Journal of Experimental Medicine 173:* 721–730, 1991.

Linsley et al., "CTLA–4 Is a Second Receptor for the B Cell Activation Antigen B7," *Journal of Experimental Medicine 174:* 561–569, 1991.

Luytjes et al., "Amplification, Expression, and Packaging of a Foreign Gene by Influenza Virus," *Cell 59:* 1107–1113, 1989.

MacPherson and Montagnier, "Agar Suspension Culture for the Selective Assay of Cells Transformed by Polyoma Virus," *Virology 23:*291–294, 1964.

Maio et al., "Modulation by cytokines of HLA antigens, intercellular adhesion molecule 1 and high molecular weight melanoma associated antigen expression and of immune lysis of clones derived from the melanoma cell line MeM 50–10," *Cancer Immunol. Immunother. 30:* 34–42, 1989.

McAleer et al., "Human hepatitis B vaccine from recombinant yeast," *Nature 307:* 178–180, 1984.

McMichael et al., "Cytotoxic T–Cell Immunity to Influenza," *New England Journal of Medicine 309*(1): 13–17, 1983.

Mendelson et al., "Expression and Rescue of a Nonselected Marker from an Integrated AAV Vector," *Virology 166:* 154–165, 1988.

Milich et al., "Hepatitis B synthetic immunogen comprised of nucleocapsid T– cell sites and an envelope B–cell epitope," *Proc. Natl. Acad. Sci. USA 85:* 1610–1614, 1988.

Miller et al., "Compact Organization of the Hepatitis B Virus Genome," *Hepatology 9*(2): 322–327, 1989.

Miller, A. D. "Retrovirus Packaging Cells," *Human Gene Therapy 1:* 5–14, 1990.

Miller, A. D., "Human gene therapy comes of age," *Nature 357:* 455–460, 1992.

Mondelli et al., "Specificity of T lymphocyte cytotoxicity to autologous hepatocytes in chronic hepatitis B virus infection: Evidence that T cells are directed against HBV core antigen expressed on hepatocytes," *Journal of Immunology* 129(6): 2773–2778, 1982.

Moore et al., "Introduction of Soluble Protein into the Class 1 Pathway of Antigen Processing and Presentation," *Cell 54:* 777–785, 1988.

Morein, B., "The iscom: an immunostimulating system," *Immunology Letters 25:* 281–284, 1990.

Moss and Flexner, "Vaccinia Virus Expression Vectors," *Annals of the New York Academy of Sciences 569:* 86–103, 1989.

Nagata et al., "Synthesis in *E. coli* of a polypeptide with human leukocyte interferon activity," *Nature 284:* 316–320, 1980.

Newton et al., "Immune Response to Cholera Toxin Epitope Inserted in *Salmonella Flagellin,*" *Science 244:* 70–72, 1989.

Okamoto et al, "Nucleotide sequence of the genomic RNA of hepatitis C virus isolated from a human carrier: comparison with reported isolates for conserved and divergent regions," *Journal of General Virology 72:* 2697–2704, 1991.

Ouchterlony, O., "Diffusion–in–Gel Methods for Immunological Analysis," *Progr. Allergy 5:* 1–78, 1958.

Perrillo et al., "A Randomized, Controlled Trail of Interferon Alpha–2b Alone and After Prednisone Withdrawal for the Treatment of Chronic Hepatitis B," *New England Journal of Medicine 323*(5): 295–301, 1990.

Powis et al., "Effect of polymorphism of an MHC–linked transporter on the peptides assembled in a class I molecule," *Nature 357:* 211–215, 1992.

Poznansky et al., "Gene Transfer into Human Lymphocytes by a Defective Human Immunodeficiency Virus Type 1 Vector," *Journal of Virology 65:* 532–536, 1991.

Radford et al., "Cell–Type Specificity of Interferon–γ–Mediated HLA Class I Gene Transcription in Human Hematopoietic Tumor Cells," *Blood* 77(9): 2008–2015, 1991.

Raney et al., "Retroviral–Mediated Transfer of Hepatitis B Surface Antigen Expression," in *Viral Hepatitis and Liver Disease,* Alan R. Liss (ed.), New York, 1988, pp. 309–312.

Robinson, W., "Hepadnaviridae and Their Replication," in *Virology,* B.N. Fields et al. (eds), Raven Press Ltd., New York, 1990, pp. 2137–2169.

Rosenfeld et al., "Adenovirus–Mediated Transfer of a Recombinant α1–Antitrypsin Gene to the Lung Epithelium in Vivo," *Science 252:* 431–434, 1991.

Sabin and Boulger, "History of Sabin attenuated poliovirus oral live vaccine strains," *Journal of Biological Standardization 1:* 115–118, 1973.

Samulski et al., "Helper–Free Stocks of Recombinant Adeno–Associated Viruses: Normal Integration Does Not Require Viral Gene Expression," *Journal of Virology 63*(9): 3822–3828, 1989.

Seif et al., "Stable Antiviral Expression in BALB/c 3T3 Cells Carrying a Beta Interferon Sequence behind a Major Histocompatibility Complex Promoter Fragment," *Journal of Virology 65:* 664–671, 1991.

Stewart et al., "Spontaneous Mammary Adenocarcinomas in Transgenic Mice That Carry and Express MTV/myc Fusion Genes," *Cell 38:* 627–637, 1984.

Stover et al., "New use of BCG for recombinant vaccines," *Nature 351:* 456–460, 1991.

Stratowa et al., "Recombinant retroviral DNA yielding high expression of hepatitis B surface antigen," *EMBO Journal* 1(12): 1573–1578, 1982.

Takahashi et al., "Induction of $CD8^+$ cytotoxic T cells by immunization with purified HIV–1 envelope protein in ISCOMs," *Nature 344:*873–875, 1990.

Tepper et al., "Murine Interleukin–4 Displays Potent Anti–Tumor Activity in Vivo," *Cell 57:* 503–512, 1989.

Tiollais et al., "Biology of Hepatitis B Virus," *Science 213:* 406–411, 1981.

Tiollias et al., "The hepatitis B Virus," *Nature 317:* 489–495, 1985.

Twu and Robinson, "Hepatitis B virus X gene can transactivate heterologous viral sequences," *Proc. Natl. Acad. Sci. USA 86:* 2046–2050, 1989.

Valenzuela et al., "Nucleotide sequence of the gene coding for the major protein of hepatitis B virus surface antigen," *Nature 280:* 815–819, 1979.

Vitiello et al., "Analysis of the HLA–restricted Influenza–specific Cytotoxic T Lymphocyte Response in Transgenic Mice Carrying a Chimeric Human–Mouse Class I Major Histocompatibility Complex," *Journal of Experimental Medicine 173:* 1007–1015, 1991.

Wang and Huang, "pH–sensitive immunoliposomes mediate target–cell–specific delivery and controlled expression of a foreign gene in mouse," *Proc, Natl. Acad. Sci. USA 84:* 7851–7855, 1987.

Watanabe et al., "Exogenous expression of mouse interferon γ cDNA in mouse neuroblastoma C1300 cells results in reduced tumorigenicity by augmented anti–tumor immunity," *Proc. Natl. Acad. Sci. USA 86:* 9456–9460, 1989.

Watanabe et al., "Prevalence of Antibody Against the Core Protein of Hepatitis C Virus in Patients with Hepatocellular Carcinoma," *International Journal of Cancer 48:* 340–343, 1991.

Williams et al., "Introduction of foreign genes into tissues of living mice by DNA–coated microprojectiles," *Proc. Natl. Acad. Sci. USA 88:* 2726–2730, 1991.

Willis, J., "Retro–secretion of recombinant proteins," *Nature 340:* 323–324, 1989.

Wu et al., "Targeting Genes: Delivery and Persistent Expression of a Foreign Gene Driven by Mammalian Regulatory Elements in Vivo," *Journal of Biological Chemistry 264*(29): 16985–16987, 1989.

Xiong et al., "Sindbis Virus: An Efficient, Broad Host Range Vector for Gene Expression in Animal Cells," *Science 243:* 1188–1191, 1989.

Yap et al., Transfer of specific cytotoxic T lymphocytes protects mice inoculated with influenza virus, *Nature 273:* 283–239, 1978.

\* cited by examiner

```
C ACC AGC AAC

→ Precore
ATG CAA CTT TTT CAC CTC TGC CTA ATC ATC TCT TGT ACA TGT CCC

→ core
ACT GTT CAA GCC TCC AAG CTG TGC CTT GGG TGG CTT TGG GGC ATG

GAC ATT GAC CCT TAT AAA GAA TTT GGA GCT ACT GTG GAG TTA CTC

TCG TTT TTG CCT TCT GAC TTC TTT CCT TCC GTC AGA GAT CTC CTA GAC

ACC GCC TCA GCT CTG TAT CGG GAA GCC TTA GAG TCT CCT GAG CAT

TGC TCA CCT CAC CAC ACC GCA CTC AGG CAA GCC ATT CTC TGC TGG GGG

GAA TTG ATG ACT CTA GCT ACC TGG GTG GGT AAT AAT TTG GAA GAT
79       81            34   85
CC G CAT CAA GGG ATC TAG TAG
CCA GCA TCT AGG GAT CTA GTA GTC AAT TAT GTT AAT ACT AAC ATG

GGT TTA AAA ATT AGG CAA CTA TTG TGG TTT CAT ATA TCT TGC CTT

ACT TTT GGA AGA GAG ACT GTA CTT GAA TAT TTG GTA TCT TTC GGA

GTG TGG ATT CGC ACT CCT CCA GCC TAT AGA CCA CCA AAT GCC CCT

ATC TTA TCA ACA CTT CCG GAA ACT ACT GTT GTT AGA CGA CGG GAC

CGA GGC AGG TCC CCT AGA AGA AGA ACT CCC TCG CCT CGC AGA CGC

AGA TCT CCA TCG CCG CGT CGC AGA AGA TCT CAA TCT CGG GAA TCT

CAA TGT TAG
```

FIG. 2

| ELISA for HBe | | | | ELISA for HB core | |
|---|---|---|---|---|---|
| Sample Supernatant | ng/ml* (Incstar) | Sample Lysate | ng/ml* (Incstar) | Sample Lysate | ng/ml** (Abbott) |
| BC10ME | 0.0 | BC10ME | 0.0 | BC10ME | 0 |
| BC/HBe 1-10 | 38.0 | BC/HBe 1-10 | 24.8 | BC core 6621 | 750 |
| BL/6 | 0.0 | BL/6 | 0.0 | BL/6 | 0 |
| BL/6/HBe 1-12 | 27.2 | BL/6/HBe 1-12 | 26.0 | BL/6 core 6625 | 100 |
| LMTK⁻ | 0.0 | LMTK⁻ | 0.0 | LMTK | 0 |
| LM/HBe 1-3 | 24.8 | LM/HBe 1-3 | 18.1 | LM core 1-2 | 250 |
| EA2/K$^b$ | 0.0 | | | EA2/K$^b$ | 0 |
| EA2/K$^b$/HBe 2-1 | 24.8 | | | EA2/K$^b$ core 1-2 | 38 |
| JA2/K$^b$ | 0.0 | | | JA2/K$^b$ | 0 |
| JA2/K$^b$/HBe 2-3 | 22.4 | | | JA2/K$^b$ core 10-1 | 200 |

Standard: rHBeAg (Biogen)
* Standard: rHBcAg (Biogen)

FIG. 5

Antibody Responses to HBcore

| No. of I.M. Injections (2 sites) | IgG Titer to HBcore |
|---|---|
| 2 | 640<br>160<br>2560<br>40<br>160 |
| 4 | 640<br>640<br>2560<br>640<br>640 |
| 6 | 2560<br>2560<br>2560<br>640<br>2560 |

FIG. 7

CD4-Depleted Cells

CD8-Depleted Cells

Ab Isotype Titers in C3H/He Mice Immunized with Formulated Vectors

| # of Ins. IM (2 sites) | Formulated Vector | Anti-HBc/HBe | | | | | |
|---|---|---|---|---|---|---|---|
| | | IgG | G1 | G2 | G2b | G3 | CTL |
| x2 | Core 6A3 | 2560 | 40 | 10,240 | 40 | 0 | + |
| x6 | Core 6A3 | 2560 | 2560 | 10,240 | 160 | 0 | + |
| x4 | Prescore/e5A 2 | 640 | 640 | 40 | 0 | 0 | – |

FIG. 12

Anti-HB core Analysis

Anti-neo^r Analysis

K3L1-CE1E2$_{715}$
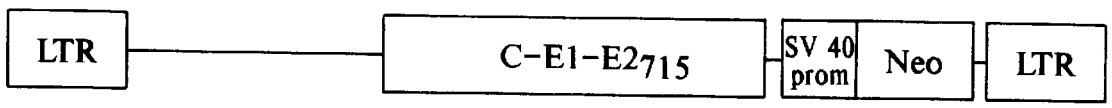
K3L1-CE1$_{330}$
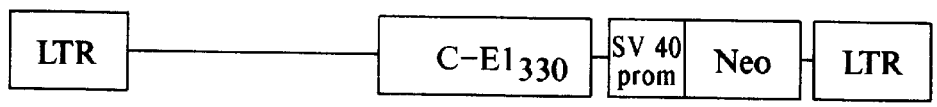
FIG. 17

SEQUENCE LISTING (1) GENERAL INFORMATION:

(iii) NUMBER OF SEQUENCES: 84

(2) INFORMATION FOR SEQ ID NO:1:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (xi) SEQUENCE DESCRIPTION: SEQ ID NO:1:

CTCGAGCTCG AGGCACCAGC ACCATGCAAC TTTTT        35

(2) INFORMATION FOR SEQ ID NO:2:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (xi) SEQUENCE DESCRIPTION: SEQ ID NO:2:

CTACTAGATC CCTAGATGCT GGATCTTCC        29

(2) INFORMATION FOR SEQ ID NO:3:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (xi) SEQUENCE DESCRIPTION: SEQ ID NO:3:

GGAAGATCCA GCATCTAGGG ATCTAGTAG         29

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:4:

GGGCGATATC AAGCTTATCG ATACCG            26

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:5:

AATACGACTC ACTATAGGG                    19

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:6:

ATTAACCCTC ACTAAAG                      17

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:7:

AATACGACTC ACTATAGGG                    19

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:8:

CCTCGAGCTC GAGCTTGGGT GGCTTTGGGG CATG    34

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:9:

ATTACCCCTC ACTAAAG                                                      17

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:10:

GTAGACCGTG CATCATGAGC                                                   20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:11:

ATAGCGGAAC AGAGAGCAGC                                                   20

(2) INFORMATION FOR SEQ ID NO:12:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO:12:

CTCGAGCTCG AGCCACCATG AGCACAAATC CTAAACCTCA AGAAAAACC AAACG             55

(2) INFORMATION FOR SEQ ID NO:13:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:13:

GCAAGCTTAA GCTTCTATCA AGCGGAAGCT GGGATGGTCA AACAAGACAG CAAAGCTAAG       60

AG                                                                      62

(2) INFORMATION FOR SEQ ID NO:14:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO:14:

AAGCTTAAGC TTCCACCATG AGCACAAATC CTAAACCTCA AGAAAAACC AAACG             55

(2) INFORMATION FOR SEQ ID NO:15:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:15:

GCCTCGAGCT CGAGCTATCA AGAGGAAGCT GGGATGGTCA AACAAGACAG CAAAGCTAAG        60

AG        62

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:16:

GTGCATGCAT GTTAGTGCG        19

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

CGTGGTGTAT GCGTTGATGG        20

(2) INFORMATION FOR SEQ ID NO:18:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:18:

CCTCGAGCTC GAGCCACCAT GGGGAAGGAG ATACTTCTAG GACCGGCCGA TAGTTTTGG        59

(2) INFORMATION FOR SEQ ID NO:19:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:19:

GCAAGCTTAA GCTTCTATCA GCGTTGGCAT GACAGGAAAG GGAGTCCCGG TAACCGCGGC        60

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:20:

ATAAATAGAA GGCCTGATAT G        21

(2) INFORMATION FOR SEQ ID NO:21:

(i) SEQUENCE CHARACTERISTICS:
        (A) LENGTH: 35 base pairs
        (B) TYPE: nucleic acid (C) STRANDEDNESS: single
            (D) TOPOLOGY: linear (xi) SEQUENCE DESCRIPTION: SEQ ID NO:21:

GCAAGCTTAC AATGTACAGG ATGCAACTCC TGTCT                              35

(2) INFORMATION FOR SEQ ID NO:22:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (xi) SEQUENCE DESCRIPTION: SEQ ID NO:22:

GACTCGAGTT ATCAAGTCAG TGTTGAGATG ATGCT                              35

(2) INFORMATION FOR SEQ ID NO:23:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (xi) SEQUENCE DESCRIPTION: SEQ ID NO:23:

GCCTCGAGAC AATGTACAGG ATGCAACTCC TGTCT                              35

(2) INFORMATION FOR SEQ ID NO:24:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (xi) SEQUENCE DESCRIPTION: SEQ ID NO:24:

GAGGGCCCTT ATCAAGTCAG TGTTGAGATG ATGCT                              35

(2) INFORMATION FOR SEQ ID NO:25:

(i) SEQUENCE CHARACTERISTICS:
            (A) LENGTH: 53 base pairs
            (B) TYPE: nucleic acid
            (C) STRANDEDNESS: single
            (D) TOPOLOGY: linear (xi) SEQUENCE DESCRIPTION: SEQ ID NO:25:

CGAAGCTTAA GCTTGCCATG GGCCACACAC GGAGGCAGGG AACATCACCA TCC          53

(2) INFORMATION FOR SEQ ID NO:26:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (xi) SEQUENCE DESCRIPTION: SEQ ID NO:26:

CCTCGAGCTC GAGCTGTTAT ACAGGGCGTA CACTTTCCCT TCTCAATCTC TC           52

(2) INFORMATION FOR SEQ ID NO:27:

(i) SEQUENCE CHARACTERISTICS:
            (A) LENGTH: 52 base pairs
            (B) TYPE: nucleic acid (C) STRANDEDNESS: single
        (D) TOPOLOGY: linear (xi) SEQUENCE DESCRIPTION: SEQ ID NO:27:

CCTCGAGCTC GAGGCCATGG GCCACACACG GAGGCAGGGA ACATCACCAT CC         52

(2) INFORMATION FOR SEQ ID NO:28:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:28:

CGGGCCCGGG CCCCTGTTAT ACAGGGCGTA CACTTTCCCT TCTCAATCTC TC         52

(2) INFORMATION FOR SEQ ID NO:29:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:29:

GCAAGCTTAA GCTTGAGGAT GTGGCTGCAG AGCCTGCTGC TCTTGGGCAC TGTGGCCTGC   60

AGCATCTCTG CA                                                     72

(2) INFORMATION FOR SEQ ID NO:30:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:30:

TCCTGGATGG CATTCACATG CTCCCAGGGC TGCGTGCTGG GGCTGGGCGA GCGGGCGGGT   60

GCAGAGATGC TGCAG                                                  75

(2) INFORMATION FOR SEQ ID NO:31:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:31:

GAATGCCATC CAGGAGGCCC GGCGTCTCCT GAACCTGAGT AGAGACACTG CTGCTGAGAT   60

G                                                                 61

(2) INFORMATION FOR SEQ ID NO:32:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (xi) SEQUENCE DESCRIPTION: SEQ ID NO:32:

CTTGTACAGC TCCAGGCGGG TCTGTAGGCA GGTCGGCTCC TGGAGGTCAA ACATTTCTGA   60

GATGACTTCT ACTGTTTCAT TCATCTCAGC AGCAGT                           96

(2) INFORMATION FOR SEQ ID NO:33:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (xi) SEQUENCE DESCRIPTION: SEQ ID NO:33:

```
CCTGGAGCTG TACAAGCAGG GCCTGCGGGG CAGCCTCACC AAGCTCAAGG GCCCCTTGAC      60

CATGATGGCC AGCCACTACA AGCAGCACTG                                      90
```

(2) INFORMATION FOR SEQ ID NO:34:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO:34:

```
GGTGATAATC TGGGTTGCAC AGGAAGTTTC CGGGGTTGGA GGGCAGTGCT GCTTGTAG        58
```

(2) INFORMATION FOR SEQ ID NO:35:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:35:

```
CAACCCAGAT TATCACCTTT GAAAGTTTCA AGAGAACCT GAAGGACTTT CTGCTTGTC        59
```

(2) INFORMATION FOR SEQ ID NO:36:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:36:

```
GCCTCGAGCT CGAGGTCTCA CTCCTGGACT GGCTCCCAGC AGTCAAAGGG GATGACAAGC      60

AGAAAGTCC                                                             69
```

(2) INFORMATION FOR SEQ ID NO:37:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:37:

```
GCTCTAGATC TAGAGTCTCA CTCCTGGACT GGCTCCCAGC AGTCAAAGGG GATGACAAGC      60

AGAAAGTCC                                                             69
```

(2) INFORMATION FOR SEQ ID NO:38:

(i) SEQUENCE CHARACTERISTICS:
        (A) LENGTH: 25 base pairs
        (B) TYPE: nucleic acid (C) STRANDEDNESS: single
            (D) TOPOLOGY: linear (xi) SEQUENCE DESCRIPTION: SEQ ID NO:38:

TTCAAGCCTC CAAGCTGTGC CTTGG                                             25

(2) INFORMATION FOR SEQ ID NO:39:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:39:

TCTGCGACGC GGCGATTGAG A                                                 21

(2) INFORMATION FOR SEQ ID NO:40:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:40:

GGAAAGAAGT CAGAAGGCAA                                                   20

(2) INFORMATION FOR SEQ ID NO:41:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:41:

CATGAGCACA AATCC                                                        15

(2) INFORMATION FOR SEQ ID NO:42:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:42:

GGGATGGTCA AACAAG                                                       16

(2) INFORMATION FOR SEQ ID NO:43:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:43:

GTCGCGTAAT TTGGGTAAGG                                                   20

(2) INFORMATION FOR SEQ ID NO:44:

(i) SEQUENCE CHARACTERISTICS:
            (A) LENGTH: 21 base pairs
            (B) TYPE: nucleic acid

```
            (C) STRANDEDNESS: single
            (D) TOPOLOGY: linear (xi) SEQUENCE DESCRIPTION: SEQ ID NO:44:

TCCTGTGTGA GTGCTATGAC G                                              21

(2) INFORMATION FOR SEQ ID NO:45:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:45:

GAAGTCACTC AACACCGTGC                                                20

(2) INFORMATION FOR SEQ ID NO:46:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:46:

CACATGTGGA ACTTCATCAG                                                20

(2) INFORMATION FOR SEQ ID NO:47:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (xi) SEQUENCE DESCRIPTION: SEQ ID NO:47:

GCCTCGAGCT CGAGGAGGAT GTGGCTGCAG AGCCTGCTGC TCTTGGGCAC TGTGGCCTGC    60

AGCATCTCTG CA                                                        72

(2) INFORMATION FOR SEQ ID NO:48:

(i) SEQUENCE CHARACTERISTICS:
            (A) LENGTH: 68 base pairs
            (B) TYPE: nucleic acid
            (C) STRANDEDNESS: single
            (D) TOPOLOGY: linear (xi) SEQUENCE DESCRIPTION: SEQ ID NO:48:

GCCTCGAGCT CGAGGTCATC CTCAGGCCAT GCAGTGGAAT TCCACTGCCT TGCACCAAGC    60

TCTGCAGG                                                             68

(2) INFORMATION FOR SEQ ID NO:49:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (xi) SEQUENCE DESCRIPTION: SEQ ID NO:49:

GCATCGATAT CGATGTTCCC CAACTTCCAA TTATGTAGCC CATGAAGTTT AGGGAATAAC    60

CCC                                                                  63
```

(2) INFORMATION FOR SEQ ID NO:50:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:50:

```
GCCTCGAGCT CGAGACCATG CCCCTATCTT ATCAACACTT CCGGAAACTA CTGTTGTTAG      60

ACGACGGGAC CGAGGCAGG                                                   79
```

(2) INFORMATION FOR SEQ ID NO:51:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:51:

```
GCATCGATAT CGATGGGCAG GATCTGATGG GCGTTCACGG TGGTCGCCAT GCAACGTGCA      60

GAGGTG                                                                 66
```

(2) INFORMATION FOR SEQ ID NO:52:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:52:

```
GCCTCGAGCT CGAGACCATG TCCCGTCGGC GCTGAATCCC GCGGACGACC CCTCTCGGGG      60

CCGCTTGGGA C                                                           71
```

(2) INFORMATION FOR SEQ ID NO:53:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:53:

```
GCATCGATAT CGATGGTCGG TCGTTGACAT TGCTGGGAGT CCAAGAGTCC TCTTATGTAA      60

GACC                                                                   64
```

(2) INFORMATION FOR SEQ ID NO:54:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (xi) SEQUENCE DESCRIPTION: SEQ ID NO:54:

```
GCCTCGAGCT CGAGACCATG ATTAGGCAGA GGTGAAAAAG TTGCATGGTG CTGGTGCGCA      60

GACCAATTTA TGCC                                                        74
```

(2) INFORMATION FOR SEQ ID NO:55:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (xi) SEQUENCE DESCRIPTION: SEQ ID NO:55:

```
GCATCGATAT CGATGCTGAC GCAACCCCCA CTGGCTGGGG CTTAGCCATA GGCCATCAGC      60

GCATGCG                                                                67
```

(2) INFORMATION FOR SEQ ID NO:56:

(i) SEQUENCE CHARACTERISTICS:
        (A) LENGTH: 655 base pairs
        (B) TYPE: nucleic acid
        (C) STRANDEDNESS: single
        (D) TOPOLOGY: linear (xi) SEQUENCE DESCRIPTION: SEQ ID NO:56:

```
CACCAGCAAC ATGCAACTTT TTCACCTCTG CCTAATCATC TCTTGTACAT GTCCCACTGT      60

TCAAGCCTCC AAGCTGTGCC TTGGGTGGCT TTGGGGCATG GACATTGACC CTTATAAAGA     120

ATTTGGAGCT ACTGTGGAGT TACTCTCGTT TTTGCCTTCT GACTTCTTTC CTTCCGTCAG     180

AGATCTCCTA GACACCGCCT CAGCTCTGTA TCGGGAAGCC TTAGAGTCTC CTGAGCATTG     240

CTCACCTCAC CACACCGCAC TCAGGCAAGC CATTCTCTGC TGGGGGGAAT TGATGACTCT     300

AGCTACCTGG GTGGGTAATA ATTTGGAAGA TCCAGCATCT AGGGATCTAG TAGTCAATTA     360

TGTTAATACT AACATGGGTT TAAAAATTAG GCAACTATTG TGGTTTCATA TATCTTGCCT     420

TACTTTTGGA AGAGAGACTG TACTTGAATA TTTGGTATCT TTCGGAGTGT GGATTCGCAC     480

TCCTCCAGCC TATAGACCAC CAAATGCCCC TATCTTATCA ACACTTCCGG AAACTACTGT     540

TGTTAGACGA CGGGACCGAG GCAGGTCCCC TAGAAGAAGA ACTCCCTCGC CTCGCAGACG     600

CAGATCTCCA TCGCCGCGTC GCAGAAGATC TCAATCTCGG GAATCTCAAT GTTAG          655
```

(2) INFORMATION FOR SEQ ID NO:57:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:57:

```
GATGATCTAG GGATCTACGA CC                                               22
```

(2) INFORMATION FOR SEQ ID NO:58:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:58:

```
ATAGTCGACT TAATTCCGGT TATTTTCCAC C                                     31
```

(2) INFORMATION FOR SEQ ID NO:59:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:59:

GCCATCGATT TATCATCGTG TTTTTCAAAG G                                 31

(2) INFORMATION FOR SEQ ID NO:60:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:60:

GCAGATCTCC CAGAGCAAGA TG                                          22

(2) INFORMATION FOR SEQ ID NO:61:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:61:

GCGTTACCTG GGTCTATTCC GTTGTGTC                                   28

(2) INFORMATION FOR SEQ ID NO:62:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:62:

GCAAGAGACC AGAGTCCC                                                18

(2) INFORMATION FOR SEQ ID NO:63:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:63:

GACAACGGTT TGGAGGG                                                 17

(2) INFORMATION FOR SEQ ID NO:64:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:64:

TCGAGGATCC GCCCGGGCGG CCGCATCGAT GTCGACG                       37

(2) INFORMATION FOR SEQ ID NO:65:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:65:

CGCGTCGACA TCGATGCGGC CGCCCGGGCG GATCC                           35

(2) INFORMATION FOR SEQ ID NO:66:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:66:

CGATAGATCT ACCGGTTAAC GCG                                        23

(2) INFORMATION FOR SEQ ID NO:67:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:67:

ACTCACCAGG ATGCTCACAT                                             20

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:68:

AGGTAATCCA TCTGTTCAGA                                             20

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:69:

CTTCCCCCTC TGTTCTTCCT                                           20

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:70:

TTCCTGTCGA GCCGTTTCAG                                           20

(2) INFORMATION FOR SEQ ID NO:71:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:71:

ATGCCCCAAG CTGAGAACCA AGACCCA                                27

(2) INFORMATION FOR SEQ ID NO:72:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:72:

TCTCAAGGGG CTGGGTCAGC TATCCCA                                27

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:73:

AGTTATATCT TGGCTTTTCA                                          20

(2) INFORMATION FOR SEQ ID NO:74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:74:

ACCGAATAAT TAGTCAGCTT                                          20

(2) INFORMATION FOR SEQ ID NO:75:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:75:

AGCTAAATTT AGGCACTTCC TCCAG                                  25

(2) INFORMATION FOR SEQ ID NO:76:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:76:

CTCGGTGCTC AGAGTCTTCT GCTCT                                  25

(2) INFORMATION FOR SEQ ID NO:77:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:77:

```
CAGGTGAAGA ATGCCTTTAA TAAGCTCCAA CAGAAAGGCA TCTACAAAGC CATGAGTGAC      60

TTTGACATC                                                             69
```

(2) INFORMATION FOR SEQ ID NO:78:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:78:

```
ATTTGGCTCT GCATTATTTT TCTGT                                           25
```

(2) INFORMATION FOR SEQ ID NO:79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:79:

```
CTCGAGGCAC CAGCACCATG                                                 20
```

(2) INFORMATION FOR SEQ ID NO:80:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:80:

```
CTCTCCACCC AAGCCGCCGG AGAACATTGA GATTCCCGAG                            40
```

(2) INFORMATION FOR SEQ ID NO:81:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:81:

```
CTCGGGAATC TCAATGTTCT CCGGCCGCTT GGGTGGAGAG                            40
```

(2) INFORMATION FOR SEQ ID NO:82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:82:

CGATGCGATG TTTCGCTTGG                                                                20

(2) INFORMATION FOR SEQ ID NO:83:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:83:

TCGACGCGTT AACCGGTAGA TCTAT                                                          25

(2) INFORMATION FOR SEQ ID NO:84:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:84:

CCGCATCAAG GGATCTAGTA G                                                              21

HEPATITIS THERAPEUTICS

CROSS-REFERENCE TO RELATED APPLICATIONS

This application is a continuation-in-part of pending U.S. application Ser. No. 081374,414, filed Jan. 19, 1995, abandoned, which is a continuation-in-part of pending U.S. application Ser. No. 08/286,829, filed Aug. 5, 1994, abandoned, which is a continuation-in-part of pending U.S. application Ser. No. 08/102,132, filed Aug. 4, 1993, abandoned, which is a continuation-in-part of now abandoned U.S. application Ser. No. 08/032,385, filed Mar. 17, 1993, abandoned, which is continuation-in-part of abandoned U.S. application Ser. No. 07/830,417, filed Feb. 4, 1992, abandoned.

TECHNICAL FIELD

The present invention relates generally to methods for treating hepatitis infections, as well as hepatitis-associated carcinomas.

BACKGROUND OF THE INVENTION

Hepatitis is a systemic disease which predominantly affects the liver. The disease is typified by the initial onset of symptoms such as anorexia, nausea, vomiting, fatigue, malaise, arthralgias, myalgias, and headaches, followed by the onset of jaundice. The disease may also be characterized by increased serum levels of the aminotransferases AST and ALT. Quantification of these enzymes in serum indicates the extent of liver damage.

There are five general categories of viral agents which have been associated with hepatitis: the hepatitis A virus (HAV); the hepatitis B virus (HBV); two types of non-A, non-B (NANB) agents, one blood-borne (hepatitis C) and the other enterically transmitted (hepatitis E); and the HBV-associated delta agent (hepatitis D).

There are two general clinical categories of hepatitis, acute hepatitis and chronic hepatitis. Symptoms for acute hepatitis range from asymptomatic and non-apparent to fatal infections. The disease may be subclinical and persistent, or rapidly progress to chronic liver disease with cirrhosis, and in some cases, to hepatocellular carcinoma. Acute hepatitis B infection in adult Caucasians in the United States progresses to chronic hepatitis B in about 5% to 10% of the cases. In the remainder of the cases, approximately 65% are asymptomatic. In the Far East, infection is usually perinatal, and 50% to 90% progress to the chronic state. It is likely that the different rates of progression are linked to the age at infection rather than genetic differences in the hosts. In the United States, about 0.2% of the population is chronically infected, with higher percentages in high-risk groups such as physicians, drug addicts and renal dialysis patients. In countries such as Taiwan, Hong Kong and Singapore, the level in the population with hepatitis infection may be as high as 10%.

In the United States, about 20% of patients with chronic hepatitis die of liver failure, and a further 5% develop hepatitis B-associated carcinoma. In the Far East, a large percentage of the population is infected with HBV, and after a long chronic infection (20 to 40 years), approximately 25% of these will develop hepatocellular carcinoma.

After the development of serologic tests for both hepatitis A and B, investigators identified other patients with hepatitis-like symptoms, and with incubation periods and modes of transmission consistent with an infectious disease, but without serologic evidence of hepatitis A or B infection. After almost 15 years, the causative agent was identified as an RNA virus. This virus (designated "hepatitis C") has no homology with HBV, retroviruses, or other hepatitis viruses.

Hepatitis C (HCV) appears to be the major cause of post-transfusion and sporadic non-A, non-B (NANB) hepatitis worldwide, and plays a major role in the development of chronic liver disease, including hepatocellular carcinoma (Kuo et al., *Science* 244:362–364, 1989; Choo et al., *British Medical Bulletin* 46(2):423–441, 1990). Of the approximately 3 million persons who receive transfusions each year, approximately 150,000 will develop acute hepatitis C (Davis et al., *New Eng.J. Med.* 321(22):1501–1506, 1989). In addition, of those that develop acute hepatitis C, at least one-half will develop chronic hepatitis C.

Until recently, no therapy has proven effective for treatment of acute or chronic hepatitis B or C infections, and patients infected with hepatitis must generally allow the disease to run its course. Most anti-viral drugs, such as acyclovir, as well as attempts to bolster the immune system through the use of corticosteroids have proven ineffective (Alter, "Viral hepatitis and liver disease," Zuckerman (ed.), New York: Alan R. Liss, pp. 537–42, 1988). Some anti-viral activity has been observed with adenosine arabinoside (Jacyna et al., *British Med. Bull.* 46:368–382, 1990), although toxic side effects which are associated with this drug render such treatment unacceptable.

One treatment that has provided some benefit for chronic hepatitis B and C infections is the use of recombinant alpha interferon (Davis et al., *New Eng. J. Med.* 321(22):1501–1506, 1989; Perrillo etal., *New Eng. J. Med.* 323:295–301, 1990). However, for patients with hepatitis B infections only about 35% of infectees responded to such treatment, and in perinatal infectees only about 10% responded to treatment. For hepatitis C infections, despite apparent short-term success utilizing such therapy, six months after termination of treatment half of the patients who responded to therapy had relapsed. In addition, a further difficulty with alpha interferon therapy is that the composition frequently has toxic side effects such as nausea, and flu-like symptoms, which require reduced dosages for sensitive patients.

A disease which is related to hepatitis B and hepatitis C infections, is hepatocellular carcinoma. Briefly, hepatocellular carcinoma is the most common cancer worldwide. It is responsible for approximately 1,000,000 deaths annually, most of them in China and in sub-Saharan Africa. There is strong evidence of an etiologic role for hepatitis B infection in hepatocellular carcinoma. Carriers of the HBV are at greater than 90 times higher risk for the development of hepatocellular carcinoma than noncarriers. In many cases, hepatitis B virus DNA is integrated within the cellular genome of the tumor. Similarly, hepatitis C virus has also recently been found to be associated with hepatocellular carcinoma, based upon the observation that circulating HCV antibodies can be found in some patients with hepatocellular carcinoma. At present, surgical resection offers the only treatment for hepatocellular carcinoma, as chemotherapy, radiotherapy, and immunotherapy have not shown much promise (Colombo et al., *Lancet* 1006–1008, 1989; Bisceglie et al., *Ann. of Internal Med.* 108:390–401, 1988; Watanabe et al., *Int. J. Cancer* 48:340–343, 1991; Bisceglie et al., *Amer. J. Gastro.* 86:335–338, 1991).

Therefore, therapeutics that could serve to augment natural host defenses against hepatitis, or against tumor induction and progression, with reduced cytotoxicity, or that

SUMMARY OF THE INVENTION

Briefly stated, the present invention is directed toward methods of treating hepatitis B and hepatitis C infections, as well as hepatocellular carcinomas (HCC). Within one aspect of the present invention, method are provided for treating hepatitis B infections in warm-blooded animals comprising the step of administering to a warm-blooded animal a vector construct which directs the expression of at least one immunogenic portion of a hepatitis B antigen, such that an immune response is generated. Within another aspect of the invention, an immunomodulatory cofactor may also be administered, or co-expressed along with an immunogenic portion of a hepatitis B antigen. Within another aspect, an immunogenic portion of a hepatitis B antigen is fused with a marker (e.g., an antibiotic resistance gene such as the neomycin gene), and administered such that an immune response is generated. Within various embodiments, the vector construct directs the expression of HBeAg, HBcAg, HBsAgs, ORF 5, ORF 6, the HBV pol antigen, or any combination of these antigens (e.g., HBeAg and HBcAg). Within one embodiment, the HBsAgs are selected from the group consisting of S, pre-S1, and pre-S2.

Within a related aspect of the present invention, vector constructs are provided which direct the co-expression of at least one immunogenic portion of a hepatitis B antigen and an immunomodulatory cofactor. Also provided are pharmaceutical compositions comprising the recombinant viruses in combination with a pharmaceutically acceptable carrier or diluent.

Within another aspect of the present invention, methods are provided for destroying hepatitis B carcinoma cells in warm-blooded animals, comprising the step of administering to a warm-blooded animal a vector construct which directs the expression of an immunogenic portion of antigen X such that an immune response is generated. Within other aspects of the invention, an immunomodulatory cofactor may also be administered, or co-expressed along with, the immunogenic portion of antigen X. Within yet another aspect of the invention, vector constructs are provided which direct the expression of an immunogenic portion of antigen X, or co-expresses this antigen with an immunomodulatory cofactor.

Within a further aspect of the present invention, methods of treating hepatitis C infections in warm-blooded animals are provided, comprising the step of administering to a warm-blooded animal a vector construct which directs the expression of at least one immunogenic portion of a hepatitis C antigen such that an immune response is generated. Within other aspects, an immunomodulatory cofactor may also be administered or co-expressed with the immunogenic portion of a hepatitis C antigen. Within various embodiments, the vector construct may express the core antigen C, antigen E1, antigen E2/NS1, antigen NS2, antigen NS3, antigen NS4, antigen NS5, or combinations thereof.

Within a related aspect of the invention, vector constructs are provided which direct the expression of at least one immunogenic portion of a hepatitis C antigen, or co-expresses this antigen in combination with an immunomodulatory cofactor. Within another embodiment, vector constructs are provided which direct the co-expression of at least one immunogenic portion of a hepatitis B antigen and at least one immunogenic portion of a hepatitis C antigen.

Within another aspect of the present invention, methods are provided for destroying hepatitis C carcinoma cells in warm-blooded animals, comprising the step of administering to a warm-blooded animal a vector construct which directs the expression of an immunogenic portion of the polyprotein antigen, such that an immune response is generated. Briefly, the Hepatitis C virus is initially expressed as a polyprotein, which is then cleaved to yield structural and non-structural proteins. Within other aspects of the invention, an immunomodulatory cofactor may also be administered, or expressed along with an immunogenic portion of a hepatitis C antigen.

Within a related aspect of the invention, vector constructs are provided which direct the expression of an immunogenic portion of the polyprotein antigen, or co-expresses this antigen with an immunomodulatory cofactor. Also provided are pharmaceutical compositions comprising these recombinant viruses in combination with a pharmaceutically acceptable carrier or diluent.

Within a further aspect of the present invention, methods are provided for treating chronic hepatitis infections in warm-blooded animals, comprising the step of administering to a warm-blooded animal a vector construct which directs the expression of at least one immunogenic portion of a hepatitis B antigen, and at least one immunogenic portion of a hepatitis C antigen, such that an immune response is generated.

Vector constructs of the present invention may be delivered by a variety of methods, including for example by a recombinant retrovirus, or a recombinant virus selected from the group consisting of poliovirus, rhinovirus, pox virus (e.g., the canary pox virus or the vaccinia virus), influenza virus, adenovirus, parvovirus (e.g., the adeno-associated virus, B19 or MVN), herpes virus, SV40, HIV, measles and alpha viruses such as the Sindbis virus and corona virus. In addition, the vector construct, or nucleic acids which encode the relevant immunogenic portion, may be administered to a patient directly, for example by transfection methods such as lipofection, direct DNA injection, microprojectile bombardment, liposomes, $CaPO_4$, or DNA ligand. The present invention also provides pharmaceutical compositions (including, for example, various adjuvants) and methods suitable for administering the immunogenic proteins themselves, vector constructs, retroviral vectors, or retroviral vectors along with immunomodulatory cofactors.

These and other aspects of the present invention will become evident upon reference to the following detailed description and attached drawings.

BRIEF DESCRIPTION OF THE DRAWINGS

FIG. 2 is a diagrammatic representation of the nucleotide sequence of HBV (adw) precore/core (SEQ ID. NO. 56) and the region of the incorrect sequence from pAM6 (ATCC 95020) clone (SEQ ID. NO. 57).

FIG. 5 is a table showing the level of expression of HBVe protein and HBV core protein from the following retrovirally transduced murine cell lines BC10ME, B1/6, L-M (TK⁻), EA2K$^b$, and retrovirally transduced human T-cell line JA2/K$^b$ as determined by ELISA.

FIG. 7 is a table which shows induction of antibody responses against HBV core antigen in C3H He CR mice injected with formulated HB Fcore/neo$^R$ vector.

FIG. 12 is a table showing the isotypes of the antibody responses against HBV core antigen and HBV e antigen in C3H/He CR mice injected with formulated HB Fcore/neo$^R$ vector.

FIG. 17 is a diagrammatic representation of vector constructs. K3L1-Ce1E2$_{715}$ which expresses HCV core, E1 and terminating at amino acid 715 of E2, and K3L1-CE1$_{330}$ which expresses HCV core and terminating at amino acid 330 of E1.

DETAILED DESCRIPTION OF THE INVENTION

Figure 1:
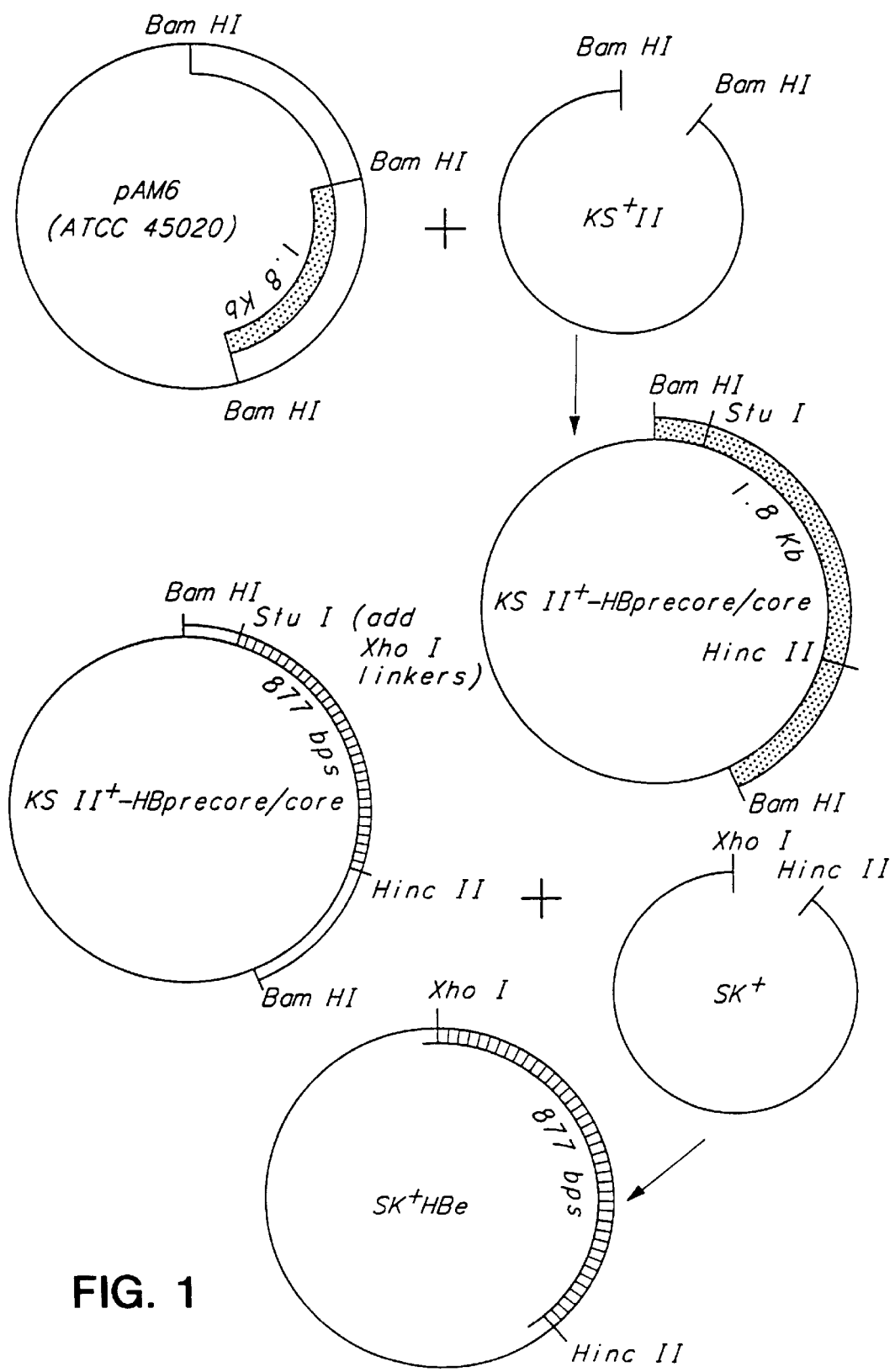
FIG. 1 is a schematic illustration which outlines the recovery of Hepatitis B e sequence from ATCC 45020.

Prior to setting forth the invention, it may be helpful to an understanding thereof to first define certain terms that will be used hereinafter. All references which have been cited below are hereby incorporated by reference in their entirety.

"Immunogenic portion" as utilized within the present invention, refers to a portion of the respective antigen which is capable, under the appropriate conditions, of causing an immune response (ie., cell-mediated or humoral). "Portions" may be of variable size, but are preferably at least 9 amino acids long, and may include the entire antigen. Representative assays which may be utilized to determine immunogenicity (e.g., cell-mediated immune response), are described in more detail below, as well as in Example 15Ai. Cell mediated immune responses may be mediated through Major Histocompatability Complex ("MHC") class I presentation, MHC Class II presentation, or both.

"Vector construct" refers to an assembly which is capable of directing the expression of the sequence(s) or gene(s) of interest. The vector construct must include promoter elements and preferably includes a signal that directs polyadenylation. In addition, the vector construct must include a sequence which, when transcribed, is operably linked to the sequence(s) or gene(s) of interest and acts as a translation initiation sequence. Preferably, the vector construct also includes a selectable marker such as Neo, SV$_2$ Neo, TK, hygromycin, phleomycin, histidinol, puromycin N-acetyl transferase, or DHFR, as well as one or more restriction sites and a translation termination sequence. In addition, if the vector construct is placed into a retrovirus, the vector construct must include a packaging signal and long terminal repeats (LTRs) appropriate to the retrovirus used (if these are not already present).

"Immunomodulatory cofactor" refers to factors which, when manufactured by one or more of the cells involved in an immune response, or, which when added exogenously to the cells, causes the immune response to be different in quality or potency from that which would have occurred in the absence of the cofactor. The quality or potency of a response may be measured by a variety of assays known to one of skill in the art including, for example, in vitro assays which measure cellular proliferation (e.g., $^3$H thymidine uptake), and in vitro cytotoxic assays (e.g., which measure $^{51}$Cr release) (see, Warner et al., *AIDS Res. and Human Retroviruses* 7:645–655, 1991). Immunomodulatory cofactors may be active both in vivo and ex vivo. Representative examples of such cofactors include cytokines, such as interleukins 2, 4, 6, and 12 (among others), alpha interferons, beta interferons, gamma interferons, GM-CSF, G-CSF, and tumor necrosis factors (TNFs). Other immunomodulatory cofactors include, for example, CD3, ICAM-1, ICAM-2, LFA-1, LFA-3, MHC class I molecules, MHC class II molecules, B7, β$_2$-microglobulin, chaperones, or analogs thereof.

As noted above, the present invention is directed towards methods and compositions for treating hepatitis B and C infections, as well as hepatocellular carcinomas. Briefly, the ability to recognize and defend against foreign pathogens is central to the function of the immune system. This system, through immune recognition, is capable of distinguishing "self" from "nonself" (foreign), which is essential to ensure that defensive mechanisms are directed towards invading entities rather than against host tissues. The methods which are described in greater detail below provide an effective means of inducing potent class I-restricted protective and therapeutic CTL responses, as well as humoral responses.

As noted above, within one aspect of the present invention, methods are provided for treating hepatitis B infections in warm-blooded animals, comprising the step of administering a vector construct to a warm-blooded animal which directs the expression of at least one immunogenic portion of a hepatitis B antigen, such that an immune response is generated.

Briefly, the hepatitis B genome is comprised of circular DNA of about 3.2 kilobases in length, and has been well characterized (Tiollais et al., *Science* 213:406–411, 1981; Tiollais et al., *Nature* 317:489–495, 1985; and Ganem and Varmus, *Ann. Rev. Biochem.* 56:651–693, 1987; see also EP 0 278,940, EP 0 241,021, WO 88/10301, and U.S. Pat. Nos. 4,696,898 and 5,024,938, which are hereby incorporated by reference). The hepatitis B virus presents several different antigens, including among others, three HB "S" antigens (HBsAgs), an HBc antigen (HBcAg), an HBe antigen (HBeAg), and an HBx antigen (HBxAg) (see Blum et al., "The Molecular Biology of Hepatitis B Virus," *TIG* 5(5):154–158, 1989). Briefly, the HBeAg results from proteolytic cleavage of P22 precore intermediate and is secreted from the cell. HBeAg is found in serum as a 17 kD protein. The HBcAg is a protein of 183 amino acids, and the HBxAg is a protein of 145 to 154 amino acids, depending on subtype.

HBsAg synthesized in animal cells is glycosylated, assembled and secreted into the cell supernatant (Tiollais et al., *Nature* 317:489–495, 1985). Three different env proteins are encoded by the S region of the HBV genome, which contains three translation start codons (Heernan et al., *J. Virol* 52:396–402, 1984; Tiollais et al., *Nature* 317:489–495, 1985). The large, middle, and major env proteins initiate translation at the first, second and third ATG and the synthesis proceeds to the end of the ORF. The $preS_1$, $preS_2$ and the S gene segments of this ORF are located between the first and second ATG, the second and third ATG, and the third ATG and the end of the ORF, respectively. The three segments encode 119, 55 or 226 amino acids, respectively. The $preS_2$ product binds pHSA (Machida et al., *Gastroenterology* 86:910–918, 1984; Michel et al., *Proc. Natl. Acad. Sci. USA* 81:7708–7712, 1985; Persing et al., *Proc. Natl. Acad. Sci. USA* 82:3440–3444, 1985). Since hepatocytes express a receptor for HSA it has been suggested that pHSA may act as an intermediate receptor, binding to middle S protein and to hepatocyte, resulting virus attachment (Michel, et al., *Proc. Natl. Acad. Sci. USA* 81:7708–7712, 1985). The major and large env proteins are either non-glycosylated (p24, p39) or are glycosylated at a site within the S region (gp27, gp42). The middle env protein is glycosylated at a site within the pre-$S_2$ region (gp33) and may also be glycosylated in the S region (gp36).

As will be evident to one of ordinary skill in the art, various immunogenic portions of the above described S antigens may be combined in order to present an immune response when administered by one of the vector constructs described herein. In addition, due to the large immunological variability that is found in different geographic regions for the S open reading frame of HBV, particular combinations of antigens may be preferred for administration in particular geographic regions. Briefly, epitopes that are found in all human hepatitis B virus S samples are defined as determinant "a". Mutually exclusive subtype determinants however have also been identified by two-dimensional double immunodiffusion (Ouchterlony, *Progr. Allergy* 5:1, 1958). These determinants have been designated "d" or "y" and "w" or "r" (LeBouvier, *J. Infect.* 123:671, 1971; Bancroft et al., *J. Immunol.* 109:842, 1972; Courouce et al., *Bibl. Haematol.* 42:1–158, 1976). The immunological variability is due to single nucleotide substitutions in two areas of the hepatitis B virus S open reading frame resulting in the following amino acid changes: (1) exchange of lysine-122 to arginine in the hepatitis B virus S open reading frame causes a subtype shift from d to y, and (2) exchange of arginine-160 to lysine causes the shift from subtype r to w. In black Africa, subtype ayw is predominant, whereas in the U.S. and northern Europe the subtype $adw_2$ is more abundant (*Molecular Biology of the Hepatitis B Virus*, McLachlan (ed.), CRC Press, 1991). As will be evident to one of ordinary skill in the art, it is generally preferred to construct a vector for administration which is appropriate to the particular hepatitis B virus subtype which is prevalent in the geographical region of administration. Subtypes of a particular region may be determined by two-dimensional double immunodiffusion or, preferably, by sequencing the S open reading frame of HBV virus isolated from individuals within that region.

Also presented by HBV are pol ("HBV pol"), ORF 5, and ORF 6 antigens. Briefly, the polymerase open reading frame of HBV encodes reverse transcriptase activity found in virions and core-like particles in infected liver. The polymerase protein consists of at least two domains: the amino terminal domain encodes the protein that primes reverse transcription, and the carboxyl terminal domain which encodes reverse transcriptase and RNase H activity. Immunogenic portions of HBV pol may be determined utilizing methods described herein (e.g, below and in Examples 15Ai and 16), utilizing vector constructs described below, and administered in order to generate an immune response within a warm-blooded animal. Similarly, other HBV antigens such as ORF 5 and ORF 6, (Miller et al., *Hepatology* 9:322–327, 1989), may be expressed utilizing vector constructs as described herein. Representative examples of vector constructs utilizing ORF 5 and ORF 6 are set forth below in Examples 5I and 5J.

Molecularly cloned genomes which encode the hepatitis B virus may be obtained from a variety of sources including, for example, the American Type Culture Collection (ATCC, Rockville, Md.). For example, ATCC No. 45020 contains the total genomic DNA of hepatitis B (extracted from purified Dane particles) (see FIG. 3 of Blum et al., *TIG* 5(5):154–158, 1989) in the Bam HI site of pBR322 (Moriarty et al., *Proc. Natl. Acad. Sci. USA* 78:2606–2610, 1981). (Note that, as described in Example 2A and as shown in FIG. 2, correctable errors occur in the sequence of ATCC No. 45020.)

As noted above, at least one immunogenic portion of a hepatitis B antigen is incorporated into a vector construct. The immunogenic portion(s) which are incorporated into the vector construct may be of varying length, although it is generally preferred that the portions be at least 9 amino acids long, and may include the entire antigen. Immunogenicity of a particular sequence is often difficult to predict, although T cell epitopes may be predicted utilizing the HLA A2.1 motif described by Falk et al. (*Nature* 351:290, 1991). From this analysis, peptides may be synthesized and used as targets in an in vitro cytotoxic assay, such as that described in Example 15Ai. Other assays, however, may also be utilized, including, for example, ELISA which detects the presence of antibodies against the newly introduced vector, as well as assays which test for T helper cells, such as gamma-interferon assays, IL-2 production assays, and proliferation assays (Examples 15B and 15C).

Immunogenic portions may also be selected by other methods. For example, the HLA A2.1/$K^b$ transgenic mouse has been shown to be useful as a model for human T-cell recognition of viral antigens. Briefly, in the influenza and hepatitis B viral systems, the murine T-cell receptor repertoire recognizes the same antigenic determinants recognized by human T-cells. In both systems, the CTL response generated in the HLA A2.1/$K^b$ transgenic mouse is directed toward virtually the same epitope as those recognized by human CTLs of the HLA A2.1 haplotype (Vitiello et al., *J. Exp. Med.* 173:1007–1015, 1991; Vitiello et al., *Abstract of Molecular Biology of Hepatitis B Virus Symposia*, 1992).

Particularly preferred immunogenic portions for incorporation into vector constructs include HBeAg, HBcAg, and HBsAgs as described in greater detail below in the Examples 5A, 5B and 5G, respectively.

Additional immunogenic portions of the hepatitis B virus may be obtained by truncating the coding sequence at various locations including, for example, the following sites: Bst UI, Ssp I, Ppu M1, and Msp I (Valenzuela et al., *Nature* 280:815–19, 1979; Valenzuela et al., *Animal Virus Genetics*: ICN/UCLA *Symp. Mol. Cell Biol*., 1980, B. N. Fields and R. Jaenisch (eds.), pp. 57–70, New York: Acad.emic). Further methods for determining suitable immunogenic portions are also described below in the context of hepatitis C.

As noted above, more than one immunogenic portion may be incorporated into the vector construct. For example, a vector construct may express (either separately or as one construct) all or immunogenic portions of HBcAg, HBeAg, HBsAgs, HBxAg as well as immunogenic portions of HCV antigens as discussed below. In addition, the vector construct may also co-express an immunomodulatory cofactor, such as alpha interferon (Finter et al., *Drugs* 42(5):749–765, 1991; U.S. Pat. No. 4,892,743; U.S. Pat. No. 4,966,843; WO 85/02862; Nagata et al., Nature 284:316–320, 1980; Familletti et al., *Methods in Enz.* 78:387–394, 1981; Twu et al., *Proc. Natl. Acad. Sci. USA* 86:2046–2050, 1989; Faktor et al., *Oncogene* 5:867–872, 1990), beta interferon (Seif et al., *J. Virol.* 65:664–671, 1991), gamma interferons (Radford et al., *The American Society of Hepatology* 20082015, 1991; Watanabe et al., *PNAS* 86:9456–9460, 1989; Gansbacher et al., *Cancer Research* 50:7820–7825, 1990; Maio et al., *Can. Immunol. Immunother*. 30:34–42, 1989; U.S. Pat. No. 4,762,791; U.S. Pat. No. 4,727,138), G-CSF (U.S. Pat. Nos. 4,999,291 and 4,810,643), GM-CSF (WO 85/04188), TNFs (Jayaraman et al., *J. Immunology* 144:942–951, 1990), Interleukin-2 (IL-2) (Karupiah et al., *J. Immunology* 144:290–298, 1990; Weber et al., *J. Exp. Med.* 166:1716–1733, 1987; Gansbacher et al., *J. Exp. Med.* 172:1217–1224, 1990; U.S. Pat. No. 4,738,927), IL-4 (Tepper et al., *Cell* 57:503–512, 1989; Golumbek etal., *Science* 254:713–716, 1991; U.S. Pat. No. 5,017,691), IL-6 (Brakenhof et al., *J. Immunol.* 139:4116–4121, 1987; WO 90/06370), ICAM-1 (Altman et al., *Nature* 338:512–514, 1989), IL-12, IL-15 (Grabstein et al., *Science* 264:965–968, 1994), ICAM-2, LFA-1, LFA-3, MHC class I molecules, MHC class II molecules, $\beta_2$-microglobulin, chaperones, CD3, B7, MHC linked transporter proteins or analogs thereof (Powis et al., *Nature* 354:528–531, 1991).

The choice of which immunomodulatory cofactor to include within a vector construct may be based upon known therapeutic effects of the cofactor, or, experimentally determined. For example, in chronic hepatitis B infections alpha interferon has been found to be efficacious in compensating a patient's immunological deficit, and thereby assisting recovery from the disease. Alternatively, a suitable immunomodulatory cofactor may be experimentally determined. Briefly, blood samples are first taken from patients with a hepatic disease. Peripheral blood lymphocytes (PBLs) are restimulated in vitro with autologous or HLA matched cells (e.g., EBV transformed cells) that have been transduced with a vector construct which directs the expression of an immunogenic portion of a hepatitis antigen and the immunomodulatory cofactor. These stimulated PBLs are then used as effectors in a CTL assay with the HLA matched transduced cells as targets. An increase in CTL response over that seen in the same assay performed using HLA matched stimulator and target cells transduced with a vector encoding the antigen alone, indicates a useful immunomodulatory cofactor. Within one embodiment of the invention, the immunomodulatory cofactor gamma interferon is particularly preferred.

Another example of an immunomodulatory cofactor is the B7 costimulatory factor. Briefly, activation of the full functional activity of T cells requires two signals. One signal is provided by interaction of the antigen-specific T cell receptor with peptides which are bound to major histocompatibility complex (MHC) molecules, and the second signal, referred to as costimulation, is delivered to the T cell by antigen presenting cells. The second signal is required for interleukin-2 (IL-2) production by T cells, and appears to involve interaction of the B7 molecule on antigen-presenting cells with CD28 and CTLA-4 receptors on T lymphocytes (Linsley et al., *J. Exp. Med*., 173:721–730, 1991a and *J. Exp. Med*., 174:561–570, 1991). Within one embodiment of the invention, B7 may be introduced into cells in order to generate efficient antigen presenting cells which prime $CD8^+$ T cells. These $CD8^+$ T cells can kill cells that are not expressing B7 because costimulation is no longer required for further CTL function. Vectors that express both the costimulatory B7 factor, and, for example, an immunogenic HBV core protein, may be made utilizing methods which are described herein. Cells transduced with these vectors will become more effective antigen presenting cells. The HBV core-specific CTL response will be augmented from the fully activated $CD8^+$ T cell via the costimulatory ligand B7. A particular preferred embodiment is shown in Example 6Ci and 6Cii.

Within one aspect of the invention, one or more immunomodulatory cofactors may be included within and coexpressed by a vector construct (or separately administered) in order to shift the balance between a $T_{H1}$ and $T_{H2}$-mediated response. Briefly, based on their cytokine secretion pattern, T helper cells are divided into two mutually exclusive sets known as T helper 1 ($T_{H1}$) or T helper 2 ($T_{H2}$). $T_{H1}$ cells secrete IL-2, IL-12, IL-15, γ-IFN and TNFβ, help B cells to differentiate and secrete $IgG_2a$, and help CTLs to proliferate. $T_{H2}$ cells secrete IL-4, IL-5, IL-6, IL-9, and IL-10, and help B cells to differentiate and secrete IgE or $IgG_1$. Within particularly preferred embodiments of the invention, it is desired to shift the balance between $T_{H1}$ and $T_{H2}$. As described in more detail below, this may be accomplished by introducing a $T_{H1}$ cytokine gene (e.g., an IL-2, IL-12, IL-15, γ-IFN or TNFβ gene) (along with one or more genes which encode the Hepatitis B or Hepatitis C antigens described herein) into target cells, and thereby shifting an immune response to a $T_{H1}$-mediated CTL response. A particularly preferred embodiment is shown in Example 6E.

Molecules which encode the above-described imnunomodulatory cofactors may be obtained from a variety of sources. For example, plasmids which contain these sequences may be obtained from a depository such as the American Type Culture Collection (ATCC, Manassa, Va.), or from commercial sources such as British Bio-technology Limited (Cowley, Oxford England). Representative examples include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon), ATCC Nos. 31902, 31902 and 39517 (which contains sequences encoding beta interferon), ATCC Nos. 39405, 39452, 39516, 39626 and 39673 (which contains sequences encoding Interleukin-2), ATCC No. 57592 (which contains sequences encoding Interleukin-4), and ATCC 67153 (which contains sequences encoding Interleukin-6).

In a similar manner, sequences which encode immunomodulatory cofactors may be readily obtained from cells which express or contain sequences which encode these cofactors. Briefly, within one embodiment, primers are prepared on either side of the desired sequence, which is subsequently amplified by PCR (see U.S. Pat. Nos. 4,683, 202, 4,683,195 and 4,800,159) (see also *PCR Technology: Principles and Applications for DNA Amplification*, Erlich (ed.), Stockton Press, 1989). In particular, a double-stranded DNA is denatured by heating in the presence of heat stable Taq polymerase, sequence specific DNA primers, ATP, CTP, GTP and TTP. Double-stranded DNA is produced when synthesis is complete. This cycle may be repeated many times, resulting in a factorial amplification of the desired DNA.

Sequences which encode immunomodulatory cofactors may also be synthesized, for example, on an Applied Biosystems Inc. DNA synthesizer (e.g., ABI DNA synthesizer model 392 (Foster City, Calif.)). Such sequences may also be linked together through complementary ends, followed by PCR amplification (Vent polymerase, New England Biomedical, Beverly, Mass.) to form long double-stranded DNA molecules (Foguet et al., *Biotechniques* 13:674–675, 1992).

Within another embodiment of the invention, vector constructs may be prepared in order to express a gene which is (or becomes) lethal in the presence of another agent (see also WO 94/13304). For example, cells which express the HSV-1 thymidine kinase gene become sensitive to gancyclovir, whereas normal cells are unaffected. Thus, vector constructs may be prepared in order to express a gene such as the Herpes Simplex Virus (HSV-1) thymidine kinase gene. The length of time the therapeutic gene(s) is expressed within the patent after administration of the vector construct may thus be limited by the administration of gancyclovir. A representative vector construct is described in more detail below in Example 5K.

Once an immunogenic portion(s) (and, if desired, an immunomodulatory cofactor) have been selected, genes which encode these proteins are placed into a vector construct which directs their expression. In general, such vectors encode only these genes, and no selectable marker. Vectors encoding and leading to expression of a specific antigen and immunomodulatory cofactor may be readily constructed by those skilled in the art. In particular, construction of vector constructs as well as administration of retroviral constructs by direct injection is described in greater detail in an application entitled "Recombinant Retroviruses" (see WO 89/09271 and WO 91/02805). These vector constructs may be used to generate transduction competent retroviral vector particles by introducing them into appropriate packaging cell lines (see WO 92/05266 and U.S. Ser. No. 08/437,465, abandoned) in order to generate producer cell lines for the production of retroviral vector particles which are replication incompetent.

Within a particularly preferred embodiment, vector constructs may be constructed to include a promoter such as SV40 (see Kriegler et al., *Cell* 38:483, 1984), cytomegalovirus ("CMV") (see Boshart et al., *Cell* 41:521–530, 1991), or an internal ribosomal binding site ("IRES"). Briefly, with respect to IRES, the upstream untranslated region of the immunoglobulin heavy chain binding protein has been shown to support the internal engagement of a bicistronic message (see Jacejak and Sarnow, *Nature* 353:90–94, 1991). This sequence is small (300 bp), and may be readily incorporated into a retroviral vector in order to express multiple genes from a multi-cistronic message whose cistrons begin with this sequence. A representative vector construct utilizing IRES is set forth in more detail below in Examples 6Ai, 6Bi, 6Ci and 6Di. Another IRES may be obtained from the encephalomyocarditis virus. One representative vector construct is set forth in Example 6E.

Various assays may be utilized in order to detect the presence of any replication competent infectious retroviruses. Representative assays include the extended $S^+$ L-assay and the *Mus dunni* cocultivation assays which are described in Example 9.

In addition, vector constructs may also be developed and utilized with other viral carriers including, for example, poliovirus (Evans et al., *Nature* 339:385–388, 1989; and Sabin, *J. Biol. Standardization* 1:115–118, 1973); rhinovirus; pox viruses, such as canary pox virus or vaccinia virus (Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112 and 4,769,330; WO 89/01973); SV40 (Mulligan et al., *Nature* 277:108–114, 1979); influenza virus (Luytjes et al., *Cell* 59:1107–1113, 1989; McMicheal et al., *N. Eng. J. Med.* 309:13–17, 1983; and Yap et al., *Nature* 273:238–239, 1978); adenovirus (Berkner, *Biotechniques* 6:616–627, 1988; Rosenfeld et al., *Science* 252:431–434, 1991); parvovirus such as adeno-associated virus (Samulski et al., *J. Vir.* 63:3822–3828, 1989; Mendelson et al., *Virol.* 166:154–165, 1988); herpes (Kit, *Adv. Exp. Med. Biol.* 215:219–236, 1989); SV40; HIV (Poznansky, *J. Virol.* 65:532–536, 1991); measles EP 0 440,219); corona virus and Sindbis virus (Xiong et al., *Science* 234:1188–1191, 1989; see also WO94/10469). A representative vector construct utilizing adenovirus is set forth in more detail below in Example 5N.

Once a vector construct has been prepared, it may be administered to a warm-blooded animal in order to treat a hepatitis B infection. Methods for administering a vector construct via a retroviral vector (such as by direct injection of the retroviral construct) are described in greater detail in an application entitled "Recombinant Retroviruses" (U.S. Ser. No. 07/586,603, abandoned) (see also U.S. Ser. No. 08/366,784, abandoned). Such methods include, for example, transfection by methods utilizing various physical methods, such as lipofection (Felgner et al., *Proc. Natl. Acad. Sci. USA* 84:7413–7417, 1989), direct DNA injection (Acsadi et al., *Nature* 352:815–818, 1991); microprojectile bombardment (Williams et al., *PNAS* 88:2726–2730, 1991); liposomes (Wang et al., *PNAS* 84:7851–7855, 1987); $CaPO_4$ (Dubensky et al., *PNAS* 81:7529–7533, 1984); or DNA ligand (Wu et al., *J. Biol. Chem.* 264:16985–16987, 1989). In addition, the vector construct, or nucleic acids which encode the relevant immunogenic portion, may be administered to a patient directly, for example by transfection methods such as lipofection, direct DNA injection, microprojectile bombardment, liposomes, $CaPO_4$, or DNA ligand. Compositions and methods suitable for administering immunogenic proteins themselves, vector constructs, viral vectors, or viral vectors along with immunomodulatory cofactors, are discussed in more detail below. A representative vector construct for direct DNA injection into patients is set forth in more detail in Example 5M.

Within another aspect of the present invention, methods are provided for treating hepatitis C infections, comprising the step of administering to a warm-blooded animal a vector construct which directs the expression of at least one immunogenic portion of a hepatitis C antigen, such that an immune response is generated. Briefly, as noted above, hepatitis C (non-A, non-B (NANB) hepatitis) is a common disease that accounts for more than 90% of the cases of hepatitis that develop after transfusion (Choo et al., *Science* 244:359–362, 1989). Most information on NANB hepatitis was derived from chimpanzee transmission studies which showed that NANB hepatitis was present in most human infections at titers of only $10^2$–$10^3$ CID/ml (chimp infectious doses per ml). In addition, the disease was found to cause the appearance of distinctive, membranous tubules within the hepatocytes of experimentally infected chimpanzees. This "tubule-forming" agent was subsequently termed hepatitis C virus (HCV).

The genomic RNA of HCV has recently been determined to have a sequence of 9379 nucleotides (Choo et al., *Proc. Natl. Acad. Sci. USA* 88:2451–2455, 1991; Choo et al., *Brit. Med. Bull.* 46(2):423–441, 1990; Okamoto et al., *J. Gen. Vir.* 72:2697–2704, 1991; see also Genbank Accession No. M67463, Intelligenetics (Mountain View, Calif.). This sequence expresses a polyprotein precursor of 3011 amino acids, which has significant homology to proteins of the flavivirus family. The polyprotein precursor is cleaved to yield several different viral proteins, including C (nucleocapsid protein) E1, E2/NS1, and non-structural proteins NS2, NS3, NS4, and NS5 (Houghton et al., *Hepatology* 14:381–388, 1991).

As noted above, within one embodiment of the present invention, at least one immunogenic portion of a hepatitis C antigen is incorporated into a vector construct. Preferred immunogenic portion(s) of hepatitis C may be found in the C and NS3–NS4 regions since these regions are the most conserved among various types of hepatitis C virus (Houghton et al., *Hepatology* 14:381–388, 1991). Particularly preferred immunogenic portions may be determined by a variety of methods. For example, as noted above for the hepatitis B virus, identification of immunogenic portions of the polyprotein may be predicted based upon amino acid sequence. Briefly, various computer programs which are known to those of ordinary skill in the art may be utilized to predict CTL epitopes. For example, CTL epitopes for the HLA A2.1 haplotype may be predicted utilizing the HLA A2.1 motif described by Falk et al. (*Nature* 351:290, 1991). From this analysis, peptides are synthesized and used as targets in an in vitro cytotoxic assay, such as that described in Example 15A.

Immunogenic proteins of the present invention may also be manipulated by a variety of methods known in the art, in order to render them more immunogenic. Representative examples of such methods include: adding amino acid sequences that correspond to T helper epitopes; promoting cellular uptake by adding hydrophobic residues; by forming particulate structures; or any combination of these (see generally, Hart, op. cit., Milich et al., *Proc. Natl. Acad. Sci. USA* 85:1610–1614, 1988; Willis, *Nature* 340:323–324, 1989; Griffiths et al., *J. Virol.* 65:450–456, 1991).

Preferred immunogenic portions may also be selected in the following manner. Briefly, blood samples from a patient with HCV are analyzed with antibodies to individual HCV polyprotein regions (e.g., HCV core, E1, E2/SNI and NS2–NS5 regions), in order to determine which antigenic fragments are present in the patient's serum. In patients treated with alpha interferon to give temporary remission, some antigenic determinants will disappear and be supplanted by endogenous antibodies to the antigen. Such antigens are useful as immunogenic portions within the context of the present invention (Hayata et al., *Hepatology* 13:1022–1028, 1991; Davis et al., *N. Eng. J. Med.* 321:1501–1506, 1989).

Once at least one immunogenic portion of hepatitis C (and, if desired, immunomodulatory cofactors and/or immunogenic portions of HBV as discussed above) has been selected, it may be placed into a vector construct which directs its expression. As described above for hepatitis B therapeutics, various recombinant viral vectors may be utilized to carry the vector construct including, for example, recombinant retroviruses (see, U.S. Ser. No. 07/586,603, abandoned). In addition, as noted above, vector constructs may be developed and utilized with other viral carriers including, for example, poliovirus, rhinovirus, pox virus, canary pox virus, vaccinia virus, influenza virus, adenovirus, parvovirus, adeno-associated virus herpes virus, SV40, HIV, measles, Sindbis virus and corona virus. In addition, the vector construct, or nucleic acids which encode the relevant immunogenic portion, may be administered to a patient directly, for example by transfection methods such as lipofection, direct DNA injection, microprojectile bombardment, liposomes, $CaPO_4$, or DNA ligand. Compositions and methods suitable for administering immunogenic proteins themselves, vector constructs, viral vectors, or viral vectors along with immunomodulatory cofactors, are discussed in more detail below. A representative vector construct utilizing hepatitis C virus core and hepatitis C virus NS3/NS4 is set forth in more detail below in Examples 5C and 5D.

Within another aspect of the present invention, methods are provided for destroying hepatitis B carcinoma cells comprising the step of administering to a warm-blooded animal a vector construct which directs the expression of an immunogenic portion of antigen X, such that an immune response is generated. Sequences which encode the HBxAg may readily be obtained by one of skill in the art given the disclosure provided herein. Briefly, within one embodiment of the present invention, a 642 bp Nco I-Taq I is recovered from ATCC 45020, and inserted into vector constructs as described above for other hepatitis B antigens.

The X antigen, however, is a known transactivator which may function in a manner similar to other potential oncogenes (e.g, E1A). Thus, it is generally preferable to first alter the X antigen such that the gene product is non-tumorigenic before inserting it into a vector construct. Various methods may be utilized to render the X antigen non-tumorigenic including, for example, by truncation, point mutation, addition of premature stop codons, or phosphorylation site alteration. Within one embodiment, the sequence or gene of interest which encodes the X antigen is truncated. Truncation may produce a variety of fragments, although it is generally preferable to retain greater than or equal to 50% of the encoding gene sequence. In addition, it is necessary that any truncation leave intact some of the immunogenic sequences of the gene product. Alternatively, within another embodiment of the invention, multiple translational termination codons may be introduced into the gene (see Example 3B). Insertion of termination codons prematurely terminates protein expression, thus preventing expression of the transforming portion of the protein.

The X gene or modified versions thereof may be tested for tumorigenicity in a variety of ways. Representative assays include tumor formation in nude mice (see Example 13A), colony formation in soft agar (see Example 13B), and preparation of transgenic animals, such as transgenic mice.

Tumor formation in nude mice or rats is a particularly important and sensitive method for determining tumorigenicity. Nude mice lack a functional cellular immune system (i.e., do not possess CTLs), and therefore provide a useful in vivo model in which to test the tumorigenic potential of cells. Normal non-tumorigenic cells do not display uncontrolled growth properties if inoculated into nude mice. However, transformed cells will proliferate and generate tumors in nude mice. Briefly, in one embodiment the vector construct is administered by intramuscular and intraperitoneal injection into nude mice. The mice are visually examined for a period of 4 to 16 weeks after injection in order to determine tumor growth. The mice may also be sacrificed and autopsied in order to determine whether tumors are present. (Giovanella et al., *J. Natl. Cancer Inst.* 48:1531–1533, 1972; Furesz et al., "Tumorigenicity testing of cell lines considered for production of biological drugs," *Abnormal Cells*, New Products and Risk, Hopps and Petricciani (eds.), Tissue Culture Association, 1985; Levenbook et al., *J. Biol. Std.* 13:135–141, 1985).

Tumorigenicity may also be assessed by visualizing colony formation in soft agar (MacPherson and Montagnier, *Virol.* 23:291–294, 1964). Briefly, one property of normal non-tumorigenic cells is anchorage-dependent growth. More specifically, normal non-tumorigenic cells will stop proliferation when they are plated in a semi-solid agar support medium, whereas tumorigenic cells will continue to proliferate and form colonies in soft agar. Briefly in one embodiment, the vector construct is transduced onto non-tumorigenic cells, and these transduced cells are cultured in soft agar.

Transgenic animals, such as transgenic mice, may also be utilized to assess the tumorigenicity of an immunogenic portion of antigen X (Stewart et al., *Cell* 38:627–637, 1984; Quaife et al., *Cell* 48:1023–1034, 1987; Koike et al., *Proc. Natl. Acad. Sci. USA* 86:5615–5619, 1989). In transgenic animals, the gene of interest may be expressed in all tissues of the animal (see generally, WO 90/08832). This dysregulated expression of the transgene may serve as a model for the tumorigenic potential of the newly introduced gene.

As noted above, once an immunogenic portion of antigen X has been selected (which is preferably non-tumorigenic), it may be inserted into a vector construct as described above, and carried by a recombinant virus. As noted above, vector constructs of the present invention may be carried in a variety of ways including, for example, by a recombinant retrovirus, or a recombinant virus selected from the group consisting of poliovirus, rhinovirus, pox virus, canary pox virus, vaccinia virus, influenza virus, adenovirus, parvovirus, adeno-associated virus, herpes virus, SV40, HIV, measles, corona and Sindbis virus. In addition, the vector construct, or nucleic acids which encode the relevant immunogenic portion, may be administered to a patient directly, for example, by transfection methods such as lipofection, direct DNA injection, microprojectile bombardment, liposomes, $CaPO_4$, or DNA ligand. Compositions and methods suitable for administering immunogenic proteins themselves, vector constructs, viral vectors, or viral vectors along with immunomodulatoty cofactors, are discussed in more detail below. A representative example is shown in Example 5E.

Within another aspect of the present invention, methods are provided for destroying hepatitis C carcinoma cells comprising the step of administering to a warm-blooded animal a vector construct which directs the expression of an immunogenic portion of a hepatitis C antigen. Preferred immunogenic portion(s) of a hepatitis C antigen may be found in the polyprotein which contains the Core antigen and the NS1–NS5 regions (Choo et al., *Proc. Natl. Acad. Sci. USA* 88:2451–2455, 1991). Particularly preferred immunogenic portions may be determined by a variety of methods. For example, as noted above preferred immunogenic portions may be predicted based upon amino acid sequence. Briefly, various computer programs which are known to those of ordinary skill in the art may be utilized to predict CTL epitopes. For example, CTL epitopes for the HLA A2.1 haplotype may be predicted utilizing the HLA A2.1 motif described by Falk et al. (*Nature* 351:290, 1991). Another method that may also be utilized to predict immunogenic portions is to determine which portion has the property of CTL induction in mice utilizing retroviral vectors (see, Warner et al., *AIDS Res. and Human Retroviruses* 7:645–655, 1991). As noted within Warner et al., CTL induction in mice may be utilized to predict cellular immunogenicity in humans. Preferred immunogenic portions may also be deduced by determining which fragments of the polyprotein antigen or peptides are capable of inducing lysis by autologous patient lymphocytes of target cells (e.g., autologous EBV-transformed lymphocytes) expressing the fragments after vector transduction of the corresponding genes (Example 16).

As noted above, once an immunogenic portion has been selected, it is generally preferable to ensure that it is non-tumorigenic. This may be accomplished by a variety of methods, including for example by truncation, point mutation, addition of premature stop codons, or phosphorylation site alteration. The polyprotein antigen or modified version thereof may also be tested for tumorigenicity utilizing the above-described methods, or by the methods described in Example 13.

Immunogenic portion(s) (as well as immunomodulatory cofactors, if desired) may then be inserted into a vector construct, and carried by a recombinant virus as described above. Additionally, as should be evident to one of ordinary skill in the art, vectors as described above for the treatment of acute and chronic HCV infection may also be utilized to treat hepatocellular carcinoma linked HCV infections. Compositions and methods suitable for administering the immunogenic proteins themselves, vector constructs, viral vectors, or viral vectors along with immunomodulatory cofactors, are discussed in more detail below.

Within another aspect of the present invention, vector constructs may be prepared which direct the co-expression of several of the above described immunogenic portions (as well as immunomodulatory co-factors, if desired). For example, within one embodiment vector constructs may be prepared which direct the co-expression of both an immunogenic portion of the hepatitis B antigen, as well as an immunogenic portion of the hepatitis C polyprotein. Such constructs may be administered as described above and below, in order to prevent or treat acute and chronic hepatitis infections of either type B or C. Similarly, within other embodiments vector constructs may be prepared which direct the co-expression of both an immunogenic portion of the hepatitis B X antigen, as well as an immunogenic portion of the hepatitis C polyprotein. Such constructs may similarly be administered in order to treat hepatocellular carcinoma of which is associated with either hepatitis B or C. In addition, because those individuals chronically infected with hepatitis B and C are at higher risk for developing hepatocellular carcinoma, such a vector may also be utilized as a prophylactic treatment for the disease. A representative example is shown in Example 6Di and 6Dii.

As noted above, various methods may be utilized to administer vector constructs of the present invention, or nucleic acids which encode the immunogenic portion(s) discussed above, to warm-blooded animals such as humans, directly (Curiel et al., *Human Gene and Therapy* 3:147–154, 1992) (see also U.S. Ser. No. 08/366,787).

In addition, an immune response (including CTL) may also be generated by administration of a bacteria or bacterial viruses which expresses the immunogenic portion(s) discussed above on its cell surface. Representative examples include BCG (Stover, *Nature* 351:456–458, 1991) and salmonella (Newton et al., *Science* 244:70–72, 1989) (see also U.S. Ser. No. 08/366,522).

Cell mediated and humoral responses may also be induced against hepatitis by parenteral administration of the immunogenic portion(s) discussed above. Briefly, immunogenic portions carrying relevant epitopes can be produced in a number of known ways (Ellis and Gerety, *J. Med. Virol.* 31:54–58, 1990), including chemical synthesis (Bergot et al., *Applied Biosystems Peptide Synthesizer User Bulletin No.* 16, 1986, Applied Biosystems, Foster City, Calif.) and DNA expression in recombinant systems, such as the insect-derived baculovirus system (Doerfler, *Current Topics in Immunology* 131:51–68, 1986), mammalian-derived systems (such as CHO cells) (Berman et al., *J. Virol.* 63:3489–3498, 1989), yeast-derived systems (McAleer et al., *Nature* 307:178–180), and prokaryotic systems (Burrel et al., *Nature* 279:43–47, 1979).

The proteins or peptides may then be purified by conventional means and delivered by a number of methods to induce cell-mediated responses, including class I and class II responses. These methods include the use of adjuvants of various types, such as ISCOMS (Morein, *Immunology Letters* 25:281–284, 1990; Takahashi et al., *Nature* 344:873–875m, 1990), liposomes (Gergoriadis et al., *Vaccine* 5:145–151, 1987), lipid conjugation (Deres et al., *Nature* 342:561–564, 1989), coating of the peptide on autologous cells (Staerz et al., *Nature* 329:449–451, 1987), pinosomes (Moore et al., *Cell* 54:777–785, 1988), alum, complete or incomplete Freund's adjuvants (Hart et al., *Proc. Natl. Acad. Sci. USA* 88:9448–9452, 1991), or various other useful adjuvants (e.g., Allison and Byars, *Vaccines* 87:56–59, Cold Spring Harbor Laboratory, 1987) that allow effective parenteral administration (Litvin et al.,*Advances in AIDS Vaccine Development*, Fifth Annual Meeting of the National Vaccine Development Groups for AIDS, Aug. 30, 1992).

Alternatively, the proteins or peptides corresponding to the immunogenic portion(s) discussed above can be encapsulated for oral administration to elicit an immune response in enteric capsules (Channock et al., *J. Amer. Med. Assoc.* 195:445–452, 1966) or other suitable carriers, such as poly (DL-lactide-co-glycolate) spheres (Eldridge et al. in Proceedings of the International Conference on Advances in AIDS Vaccine Development, DAIDS, NIAID, U.S. Dept. of Health & Human Services, 1991) for gastrointestinal release.

As noted above, immunogenic proteins of the present invention may also be manipulated by a variety of methods known in the art, in order to render them more immunogenic. Representative examples of such methods include: adding amino acid sequences that correspond to T helper epitopes; promoting cellular uptake by adding hydrophobic residues; by forming particulate structures; or any combination of these (see generally, Hart, op. cit., Milich et al., *Proc. Natl. Acad. Sci. USA* 85:1610–1614, 1988; Willis, *Nature* 340:323–324, 1989; Griffiths et al., *J. Virol.* 65:450–456, 1991). In addition, a monomeric non-particulate form of Hepatitis B virus core protein might be useful for priming T-help for CTL prior to administration of the vector construct. This is shown in Example 14Ai.

Within preferred embodiments of the present invention, pharmaceutical compositions are provided comprising one of the above described recombinant viruses, such as a recombinant retrovirus or recombinant virus selected from the group consisting of poliovirus, rhinovirus, pox virus, canary pox virus, vaccinia virus, influenza virus, adenovirus, parvovirus, adeno-associated virus, herpes virus, SV40, HIV, measles, corona and Sindbis virus in combination with a pharmaceutically acceptable carrier or diluent. The composition may be prepared either as a liquid solution, or as a solid form (e.g., lyophilized see WO 94/11414) which is suspended in a solution prior to administration. In addition, the composition may be prepared with suitable carriers or diluents for either injection (e.g., intramuscular, intraperitoneal, intradermal, subcutaneous, or intravenous injection), oral, or rectal administration. Generally, the recombinant virus is utilized at a concentration ranging from 0.25% to 25%, and preferably about 5% to 20% before formulation. Subsequently, after preparation of the composition, the recombinant virus will constitute about 1 $\mu$g of material per dose, with about 10 times this amount material (10 $\mu$g) as copurified contaminants. Preferably, the composition is prepared in 0.1–1.0 ml of aqueous solution formulated as described below.

Pharmaceutically acceptable carriers or diluents are non-toxic to recipients at the dosages and concentrations employed. Representative examples of carriers or diluents for injectable solutions include water, isotonic saline solutions which are preferably buffered at a physiological pH (such as phosphate-buffered saline or Tris-buffered saline), mannitol, dextrose, glycerol, and ethanol, as well as polypeptides or proteins such as human serum albumin. A particularly preferred composition comprises a vector or recombinant virus in 10 mg/ml mannitol, 1 mg/ml HSA, 20 mM Tris, pH 7.2 and 150 mM NaCl. In this case, since the recombinant vector represents approximately 1 $\mu$g of material, it may be less than 1% of high molecular weight material, and less than 1/100,000 of the total material (including water). This composition is stable at −70° C. for at least six months. The composition may be injected intravenously (i.v.) or subcutaneously (s.c.), although it is generally preferable to inject it intramuscularly (i.m.). The individual doses normally used are $10^7$ to $10^9$ c.f.u. (colony forming units of neomycin resistance titered on HT1080 cells). These are administered at one to four week intervals for three or four doses initially. Subsequent booster shots may be given as one or two doses after 6–12 months, and thereafter annually.

Oral formulations may also be employed with carriers or diluents such as cellulose, lactose, mannitol, poly (DL-lactide-co-glycolate) spheres, and/or carbohydrates such as starch. The composition may take the form of, for example, a tablet, gel capsule, pill, solution, or suspension, and additionally may be formulated for sustained release. For rectal administration, preparation of a suppository may be accomplished with traditional carriers such as polyalkalene glucose, Or a triglyceride.

As noted above, the vector construct may direct expression of an immunomodulatory cofactor in addition to at least one immunogenic portion of a hepatitis antigen. If the vector construct, however, does not express an immunomodulatory cofactor which is a cytokine, this cytokine may be included in the above-described compositions, or may be administered separately (concurrently or subsequently) with the above-described compositions. Briefly, within such an embodiment, the immunomodulatory cofactor (e.g., IL-2, IL-12, IL-15 and/or γ-IFN) is preferably administered according to standard protocols and dosages as prescribed in *The Physician's Desk Reference*. For example, alpha interferon may be administered at a dosage of 1–5 million units/day for 2–4 months, and IL-2 at a dosage of 10,000–100,000 units/kg of body weight, 1–3 times/day, for 2–12 weeks. Gamma interferon may be administered at dosages of 150,000–1,500,000 units 2–3 times/week for 2–12 weeks.

The following examples are offered by way of illustration and not by way of limitation.

EXAMPLES

Example 1

ISOLATION OF HBV E/CORE SEQUENCE

A 1.8 Kb BamH I fragment containing the entire precore/core coding region of hepatitis B is obtained from plasmid pAM6 (ATCC No 45020) and ligated into the BamH I site of KS II+ (Stratagene, La Jolla, Calif.). This plasmid is designated KS II+ HBpc/c, FIG. 1. Xho I linkers are added to the Stu I site of precore/core in KS II+ HBpc/c (at nucleotide sequence 1704), followed by cleavage with Hinc II (at nucleotide sequence 2592). The resulting 877 base pair Xho I-Hinc II precore/core fragment is cloned into the Xho I/Hinc II site of SK II+. This plasmid is designated SK+ HBe, FIG. 1.

Example 2

PREPARATION OF SEQUENCES UTILIZING PCR

A. Site-Directed Mutagenesis of HBV e/core Sequence Utilizing PCR

The precore/core gene in plasmid KS II+ HB pc/c is sequenced to determine if the precore/core coding region is correct. This sequence was found to have a single base-pair deletion which causes a frame shift at codon 79 that results in two consecutive in-frame TAG stop codons at codons 84 and 85, FIG. 2. This deletion is corrected by PCR overlap extension (Ho et al., *Gene* 77:51–59, 1989) of the precore/core coding region in plasmid SK+ HBe. Four oligonucleotide primers are used for the 3 PCR reactions performed to correct the deletion.

Figure 3:
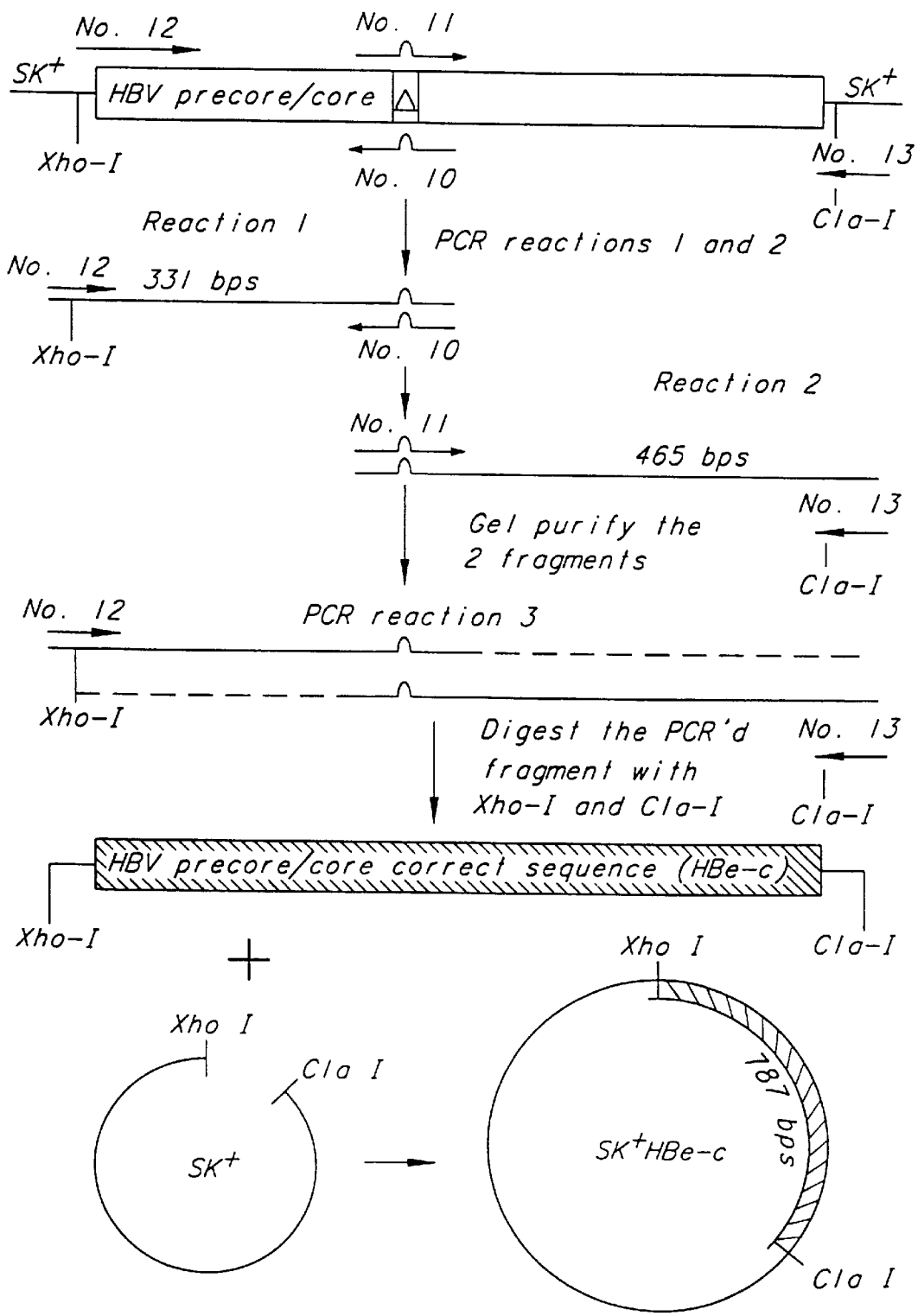
FIG. 3 is a schematic representation of the protocol utilized to correct the mutation in HB precore/core sequence from pAM6 (ATCC 45020).

The first reaction utilizes the plasmid KS II+HB pc/c as the template and as two primers. The sense primer sequence corresponds to the nucleotide sequence 1855 to 1827 of the adw strain and contains two Xho I restriction sites at the 5' end. The nucleotide sequence numbering is obtained from Genbank (Intelligenics, Inc., Mountain View, Calif.).
(SEQUENCE ID. NO. 1)
  5'-3': CTC GAG CTC GAG GCA CCA GCA CCA TGC AAC TTT TT The second primer sequence corresponds to the anti-sense nucleotide sequence 2158 to 2130 of the adw strain of hepatitis B virus, and includes codons 79, 84 and 85.
(SEQUENCE ID. NO. 2)
  5'-3': CTA CTA GAT CCC TAG ATG CTG GAT CTT CC The second reaction also utilizes the plasmid KS II+ HB pc/c as the template and two primers. The sense primer corresponds to nucleotide sequence 2130 to 2158 of the adw strain, and includes codons 79, 84 and 85.
(SEQUENCE ID. NO. 3)
  5'-3': GGA AGA TCC AGC ATC TAG GGA TCT AGT AG The second primer corresponds to the anti-sense nucleotide sequence from SK+ plasmid polylinker and contains a Cla I site 135 bp downstream of the stop codon of the HBV precore/core coding region.
(SEQUENCE ID. NO. 4)
  5'-3': GGG CGA TAT CAA GCT TAT CGA TAC CG The third reaction also utilizes two primers and the products of the first and second PCR reactions. The sense primer corresponds to nucleotide sequence 5 to 27 of the adw strain, and contains two Xho I restriction sites at the 5' end.
(SEQUENCE ID. NO. 1)
  5'-3': CTC GAG CTC GAG GCA CCA GCA CCA TGC AAC TTT TT The second primer sequence corresponds to the anti-sense nucleotide sequence from the SK+ plasmid polylinker and contains a Cla I site 135 bp downstream of the stop codon of the HBV precore/core coding region.
(SEQUENCE ID. NO. 4)
  5'-3': GGG CGA TAT CAA GCT TAT CGA TAC CG The first PCR reaction corrects the deletion in the anti-sense strand and the second reaction corrects the deletion in the sense strands. PCR reactions one and two correct the mutation from CC to CCA which occurs in codon 79 and a base pair substitution from TCA to TCT in codon 81 (see FIG. 2). Primer 1 contains two consecutive Xho I sites 10 bp upstream of the ATG codon of HBV e coding region and primer 4 contains a Cla I site 135 bp downstream of the stop codon of HBV precore/core coding region. The products of the first and second PCR reactions are extended in a third PCR reaction to generate one complete HBV precore/core coding region with the correct sequence (FIG. 3).

The PCR reactions are performed using the following cycling conditions: The sample is initially heated to 94° C. for 2 minutes. This step, called the melting step, separates the double-stranded DNA into single strands for synthesis. The sample is then heated at 56° C. for 30 seconds. This step, called the annealing step, permits the primers to anneal to the single stranded DNA produced in the first step. The sample is then heated at 72° C. for 30 seconds. This step, called the extension step, synthesizes the complementary strand of the single stranded DNA produced in the first step. A second melting step is performed at 94° C. for 30 seconds, followed by an annealing step at 56° C. for 30 seconds which is followed by an extension step at 72° C. for 30 seconds. This procedure is then repeated for 35 cycles resulting in the amplification of the desired DNA product.

The PCR reaction product is purified by gel electrophoresis and transferred onto NA 45 paper (Schleicher and Schuell, Keene, N.H The desired 787 bp DNA fragment is eluted from the NA 45 paper by incubating for 30 minutes at 65° C. in 400 µl high salt buffer (1.5 M NaCl, 20 mM Tris, pH 8.0, and 0.1 mM EDTA). Following elution, 500 µl of phenol:chloroform:isoamyl alcohol (25:24:1) is added to the solution. The mixture is vortexed and then centrifuged 14,000 rpm for 5 minutes in a Brinkmann Eppendorf centrifuge (5415L). The aqueous phase, containing the desired DNA fragment, is transferred to a fresh 1.5 ml microfuge tube and 1.0 ml of 100% EtOH is added. This solution is incubated on dry ice for 5 minutes, and then centrifuged for 20 minutes at 10,000 rpm. The supernatant is decanted, and the pellet is rinsed with 500 µl of 70% EtOH. The pellet is dried by centrifugation at 10,000 rpm under vacuum, in a Savant Speed-Vac concentrator, and then resuspended in 10 µl deionized $H_2O$. One microliter of the PCR product is analyzed by 1.5% agarose gel electrophoresis. The 787 Xho I-Cla I precore/core PCR amplified fragment is cloned into the Xho I-Cla I site of SK+ plasmid. This plasmid is designated SK+ HBe-c. *E. coli* (DH5 alpha, Bethesda Research Labs, Gaithersburg, Md.) is transformed with the SK+ HBe-c plasmid and propagated to generate plasmid DNA. The plasmid is then isolated and purified, essentially as described by Bimboim et al. (*Nuc. Acid Res.* 7:1513, 1979; see also *Molecular Cloning: A Laboratory Manual*, Sambrook et al. (eds.), Cold Spring Harbor Press, 1989).

Figure 4:
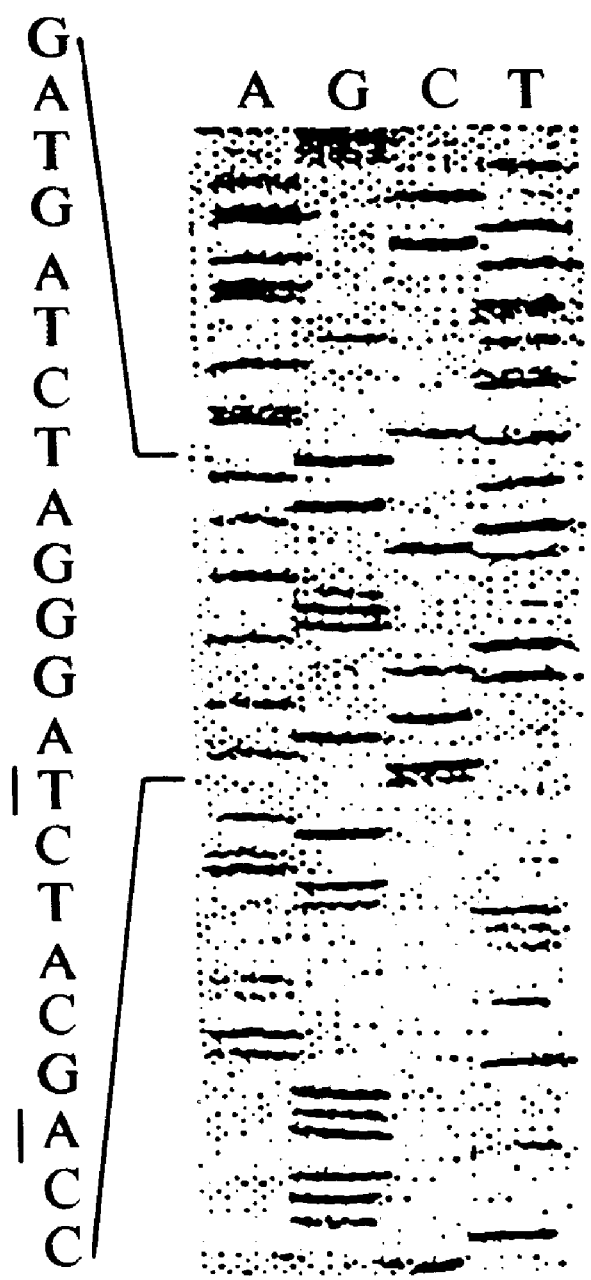
FIG. 4 is a DNA sequencing gel showing the corrected nucleotide sequences from SK+ HBe-c Sequence ID. NO. 57.

The SK+ HB e-c plasmid is analyzed to confirm the sequence of the precore/core gene (FIG. 4).

Isolation of HBV Core Sequence

The single base pair deletion in plasmid SK+ HBe is corrected by PCR overlap extension as described in Example 2A. Four oligonucleotide primers are used for the PCR reactions performed to correct the mutation.

The first reaction utilizes the plasmid KS II + HB pc/c as the template and two primers. The sense primer corresponds to the nucleotide sequence for the T-7 promoter of SK+ HBe plasmid.
SEQUENCE ID. NO. 5)

5'-3': AAT ACG ACT CAC TAT AGG G

The second primer corresponds to the anti-sense sequence 2158 to 2130 of the adw strain, and includes codons 79, 84 and 85.
(SEQUENCE ID. NO. 2)

5'-3': CTA CTA GAT CCC TAG ATG CTG GAT CTT CC

The second reaction utilizes the plasmid KS II + HB pc/c as the template and two primers. The anti-sense primer corresponds to the nucleotide sequence for the T-3 promoter present in SK+ HBe plasmid.
(SEQUENCE ID. NO. 6)

5'-3': ATT AAC CCT CAC TAA AG

The second primer corresponds to the sense nucleotide sequence 2130 to 2158 of the adw strain, and includes codons 79, 84 and 85.
(SEQUENCE ID. NO. 3)

5'-3': GGA AGA TCC AGC ATC TAG GGA TCT AGT AG

The third reaction utilizes two primers and the products of the first and second PCR reactions. The anti-sense primer corresponds to the nucleotide sequence for the T-3 promoter present in SK+ HBe plasmid.
(SEQUENCE ID. NO. 6)

5'-3': ATT AAC CCT CAC TAA AG

The second primer corresponds to the sense sequence of the T-7 promoter present in the SK+ HBe plasmid.
(SEQUENCE ID. NO. 7)

5'-3': AAT ACG ACT CAC TAT AGG G

The PCR product from the third reaction yields the correct sequence for HBV precore/core coding region.

To isolate HBV core coding region, a primer is designed to introduce the Xho I restriction site upstream of the ATG start codon of the core coding region, and eliminate the 29 amino acid leader sequence of the HBV precore coding region. In a fourth reaction, the HBV core coding region is produced using the PCR product from the third reaction and the following two primers.

The sense primer corresponds to the nucleotide sequence 1885 to 1905 of the adw strain and contains two Xho I sites at the 5' end.
(SEQUENCE ID. NO. 8)

5'-3': CCT CGA GCT CGA GCT TGG GTG GCT TTG GGG CAT G

The second primer corresponds to the anti-sense nucleotide sequence for the T-3 promoter present in the SK+ HBe plasmid. The approximately 600 bp PCR product from the fourth PCR reaction contains the HBV core coding region and novel Xho I restriction sites at the 5' end and Cla I restriction sites at the 3' end that was present in the multicloning site of SK+ HBe plasmid.
(SEQUENCE ID. NO. 9)

5'-3': ATT ACC CCT CAC TAA AG

Following the fourth PCR reaction, the solution is transferred into a fresh 1.5 ml microfuge tube. Fifty microliters of 3 M sodium acetate is added to this solution followed by 500 μl of chloroform:isoamyl alcohol (24:1). The mixture is vortexed and then centrifuged at 14,000 rpm for 5 minutes. The aqueous phase is transferred to a fresh microfuge tube and 1.0 ml 100% EtOH is added. This solution is incubated at −20° C. for 4.5 hours, and then centrifuged at 10,000 rpm for 20 minutes. The supernatant is decanted, and the pellet rinsed with 500 μl of 70% EtOH. The pellet is dried by centrifugation at 10,000 rpm under vacuum and then resuspended in 10 μl deionized $H_2O$. One microliter of the PCR product is analyzed by electrophoresis in a 1.5% agarose gel.

C. Isolation of HCV Core Sequence

A 200 μl sample of serum is obtained from a patient with chronic non-A, non-B hepatitis and the viral RNA is prepared by the procedure of Cristiano et al., Hepatology 14:51–55, 1991. The 200 μl of serum is mixed with 550 μl of extraction buffer consisting of 4.2 M guanidinium isothiocyanate (Fluka Chemical Corp., St. Louis, Mo.), 0.5% sodium lauryl sarkosate and 25 mM Tris HCL, pH 8.0, and extracted once with phenol:chloroform (1:1), and once with chloroform. The aqueous phase is precipitated with an equal volume of isopropyl alcohol and centrifuged at 14,000 rpm for 5 minutes. The resulting pellet containing the viral RNA is washed with 70% ethanol and resuspended in 200 μl of RNase-free deionized $H_2O$. Four microliter of RNasin (40,000 U/ml) (Promega Corp., Madison, Wis.) is added to the mixture. This mixture contains the HCV RNA and is the template for the following reverse transcriptase reaction. Using the DNA CYCLE kit (Invitrogen, San Diego, Calif.) a full-length first strand cDNA is generated from the isolated viral mRNA. Seven microliters of the reverse transcription reaction above (100 ng of full-length first strand cDNA) is amplified by PCR in a total volume of 100 μl of reaction mixture containing 10 μl of 10×PCR buffer (vial C16), 2 μl of 25 mM dNTPs (vial C11), 5% DMSO, 4 U of Taq DNA polymerase (Cetus, Los Angeles, Calif.) and 2 1M of each of the two primers.

The sense primer corresponds to the nucleotide sequence 316 to 335 and is the nucleotide sequence for the 5' region of the hepatitis C virus core open reading frame and includes the ATG start codon.
(SEQUENCE ID. NO. 10)

5'-3': GTA GAC COT GCA TCA TGA GC

The second primer corresponds to the anti-sense nucleotide sequence 1172 to 1153 present in the hepatitis C virus envelope open reading frame.
(SEQUENCE ID. NO. 11)

5'-3': ATA GCG GAA CAG AGA GCA GC

The reaction mixture is placed into a PCR Gene AMP System 9600 (Perkin-Elmer, Cetus, Los Angeles, Calif.). The PCR program regulates the temperature of the reaction vessel first at 95° C. for 1 minute, then at 60° C. for 2 minutes, and finally at 72° C. for 2 minutes. This cycle is repeated 40 times. Following the 40th cycle, the final cycle regulates the reaction vessel at 95° C. for 1 minute, then at 67° C. for 2 minutes, and finally at 72° C. for 7 minutes.

In the first PCR reaction, the HCV core open reading frame from the 5' region upstream from the ATG start codon to the beginning of the HCV E1 open reading frame is amplified. The nucleotide numbering sequence is according to the HCV-J strain (Kato et al., Proc. Natl. Acad. Sci. USA 87:9524–9528, 1990).

The product from the first PCR reaction is amplified in a second PCR reaction. The second PCR amplification is performed with the sense primer that corresponds to the nucleotide sequence 329 to 367 (and is the nucleotide sequence for the 5' end of the hepatitis C virus core open reading frame). The 5' end of the sense primer contains two consecutive Xho I restriction sites. The primer also contains a number of nucleotide changes introduced in the area of the initiator ATG start codon to conform to appropriate rules for translation initiation (Kozak, *Mol. Biol.* 196:947–950, 1987).

(SEQUENCE ID. NO. 12)

5'-3': CTC GAG CTC GAG CCA CCA TGA GCA CAA ATC CTA AAC CTC AAA GAA AAA CCA AAC G

The anti-sense primer is designed to contain two consecutive stop codons in frame with HCV core gene. The 5' end of the primer contains two consecutive Hind III restriction sites. This primer corresponds to the nucleotide sequence 902 to 860, and is the junction between the hepatitis C virus core and E1 open reading frame.

(SEQUENCE ID. NO. 13)

5'-3': GC AAG CTT AAG CTT CTA TCA AGC GGA AGC TGG GAT GGT CAA ACA AGA CAG CAA AGC TAA GAG

Using a TA Cloning Kit (Invitrogen, San Diego, Calif.), the 570 bp PCR-amplified product from the second reaction is then ligated into the pCR II vector (Invitrogen, San Diego, Calif.) and transformed into frozen competent *E. coli* cells. After verification by DNA sequencing this construct is designated pCR II Xh-H HCV core.

The product from the first PCR reaction is also amplified in a third PCR reaction. The 5' end of the sense primer contains two consecutive Hind III restriction sites. This primer also contains nucleotide changes to conform to the Kozak rules for translation initiation and corresponds to the nucleotide sequence 329 to 367 of the HCV-J sequence (and is the nucleotide sequence for the 5' end of the hepatitis C virus core open reading frame)

(SEQUENCE ID. NO. 14)

5'-3': AAG CTT AAG CTT CCA CCA TGA GCA CAA ATC CTA AAC CTC AAA GAA AAA CCA AAC G

The anti-sense primer is designed to contain two stop codons in frame with the HCV core gene, and two consecutive Xho I restriction sites at the 5' end of the primer. This primer corresponds to the anti-sense nucleotide sequence 902 to 860, and is the junction between hepatitis C virus core and the E1 reading frame.

SEQUENCE ID. NO. 15)

5'-3': GC CTC GAG CTC GAG CTA TCA AGA GGA AGC TGG GAT GGT CAA ACA AGA CAG CAA AGC TAA GAG

As described above, the 570 bp PCR amplified product from the third reaction is ligated into the pCR II vector. After verification by DNA sequencing this construct is designated pCR II H-Xh HCV core.

D. Isolation of HCV NS3/NS4 Sequence

The hepatitis C virus NS3/NS4 sequence is isolated from 200 µl of serum obtained from a patient with chronic non-A, non-B hepatitis as described in Example 2C. The viral RNA is reverse transcribed by the cDNA CYCLE Kit (Invitrogen, San Diego, Calif.), and amplified by PCR. In the first PCR reaction, the HCV NS3/NS4 open reading frame is amplified.

The first PCR amplification is performed with two primers. The sense primer corresponds to the nucleotide sequence 3088 to 3106 of the hepatitis C virus NS2 open reading frame.

SEQUENCE ID. NO. 16)

5'-3': GTG CAT GCA TGT TAG TGC G

The second primer corresponds to the anti-sense nucleotide sequence 6530 to 6511 of the hepatitis C virus NS5 open reading frame.

(SEQUENCE ID. NO. 17)

5'-3': CGT GGT GTA TGC GTT GAT GG

The product from the first PCR reaction is amplified in a second PCR reaction. The 5' end of the sense primer contains two consecutive Xho I restriction sites. This primer also contains nucleotide changes to conform to the Kozak rules for translation initiation and corresponds to the nucleotide sequence 3348 to 3385 of the 5' region of the NS3 open reading frame of the HCV-J sequence.

(SEQUENCE ID. NO. 18)

5'-3': C CTC GAG CTC GAG CCA CCA TGG GGA AGG AGA TAC TTC TAG GAC CGG CCG ATA GTT TTG G

This primer corresponds to the nucleotide sequence 6368 to 6328 of the 3' region of the NS4 open reading frame of the HCV-J sequence. This primer contains two consecutive stop codons in frame with HCV NS4 NS4 gene and two consecutive Hind III sites at its 5' end.

(SEQUENCE ID. NO. 19)

5'-3': GC AAG CTT AAG CTT CTA TCA GCG TTG GCA TGA CAG GAA AGG GAG TCC CGG TAA CCG CGG C

The 3020 bp PCR product from the second PCR reaction is ligated into the pCR II plasmid, verified by DNA sequencing and designated pCR II Xh-H HCV NS3/NS4.

E. Amplification of Immunomodulatory Cofactor IL-2

Jurkat cells are resuspended at $1\times10^6$ cells/ml to a total volume of 158 ml in T75 flasks. Phytohemagglutinin (PHA; Sigma, St. Louis, Mo.), is added to 1% of total volume (1.58 ml total), and incubated overnight at 37° C., 5% $CO_2$. On the following day, cells are harvested in three 50 ml centrifuge tubes (Corning, Corning, N.Y.). The three pellets are combined in 50 ml PBS, centrifuged at 3,000 rpm for 5 minutes and supernatant decanted. This procedure is repeated. Poly $A^+$ mRNA is isolated using the Micro-Fast Track mRNA Isolation Kit, version 1.2 (Invitrogen, San Diego, Calif.). The isolated intact mRNA is used as the template to generate full-length first strand cDNA by the cDNA CYCLE kit with the following primer.

This oligonucleotide corresponds to the anti-sense nucleotide sequence of the IL-2 mRNA, 25 base pairs downstream of the stop codon.

(SEQUENCE ID. NO. 20)

5'-3': ATA AAT AGA AGG CCT GAT ATG

The product from the reverse transcription reaction is amplified in two separate reactions. The first PCR amplification is performed with the sense primer that corresponds to three bp upstream of the ATG start codon. This primer contains a Hind III site at its 5' end and contains the 5' region of the IL-2 open reading frame including the ATG start codon.

(SEQUENCE ID. NO. 21)

5'-3': GCA AGC TTA CAA TGT ACA GGA TGC AAC TCC TGT CT

The anti-sense primer is complementary to the 3' region of IL-2 open reading frame and starts three bp downstream of the TGA stop codon. This primer contains an Xho I site at the 5' end of the primer.

(SEQUENCE ID. NO. 22)

5'-3': GAC TCG AGT TAT CAA GTC AGT GTT GAG ATG ATG CT

The 467 bp PCR product from the first PCR reaction is ligated into the pCR II plasmid, verified by DNA sequencing and designated pCR II H-Xh IL-2.

The product from the reverse transcription reaction is amplified in a second PCR reaction. The second PCR amplification is performed with the sense primer that corresponds to three bp upstream of the ATG start codon. This primer contains a Xho I site at its 5' end and the 5' region of the IL-2 open reading frame including the ATG start codon.

(SEQUENCE ID. NO. 23)

5'-3': GCC TCG AGA CAA TOT ACA GGA TGC AAC TCC TGT CT

The anti-sense primer is complementary to the 3' region of IL-2 open reading frame and starts three bp downstream of the TGA stop codon. This primer contains an Apa I site at the 5' end of the primer.

(SEQUENCE ID. NO. 24)

5'-3': GAG GGC CCT TAT CAA GTC AGT GTT GAG ATG ATG CT

The 467 bp PCR product from the second PCR reaction is ligated into the pCR II plasmid, verified by DNA sequencing and transformed into frozen competent *E. coli* cells. This vector construct is designated pCR II Xh-A IL-2.

F. Amplification of Immunomodulatory Cofactor B7

Raji cells are suspended at $1 \times 10^6$ cells/ml to a total volume of 158 ml in five T75 flasks and incubated overnight at 37° C., 5% $CO_2$. On the following day, cells are harvested in three 50 ml centrifuge tubes. Cell pellets are combined in 50 ml PBS, centrifuged at 2,000 rpm for 10 minutes and supernatant decanted. This procedure is repeated. Poly $A^+$ mRNA is isolated as described in Example 2E. The isolated intact RNA is used as the template to generate full-length first strand cDNA using the cDNA CYCLE kit, followed by two separate PCR amplification reactions essentially as described in Example 2E, except that 1 µl of oligo dT (vial C5) is used as the primer. The nucleotide numbering system is obtained from Freeman et al. (*J. Immunol.* 143:2714–2722, 1989).

The first PCR amplification is performed with two primers. The sense primer corresponds to the nucleotide sequence 315 to 353 of B7. This primer contains the 5' region of the B7 open reading fame including the ATG start codon and has two Hind III restriction sites at the 5' end.

(SEQUENCE ID. NO. 25)

5'-3': CG AAG CTT AAG CTT GCC ATG GGC CAC ACA CGG AGG CAG GGA ACA TCA CCA TCC

The second primer corresponds to the anti-sense nucleotide sequence 1187 to 1149 of B7. This primer is complementary to the 3' region of the B7 open reading frame ending at the TAA stop codon and contains two Xho I restriction sites at the 5' end.

(SEQUENCE ID. NO. 26)

5'-3': C CTC GAG CTC GAG CTG TTA TAC AGG GCG TAC ACT TTC CCT TCT CAA TCT CTC

The 868 bp PCR product from the first PCR reaction is ligated into the pCR II plasmid, verified by DNA sequencing and transformed into frozen competent *E. coli* cells. This vector construct is designated PCR II H-Xh-B7 and verified by DNA sequencing.

The second PCR amplification is performed with two primers. The sense primer corresponds to the nucleotide sequence 315 to 353 of B7. This primer contains the 5' region of the B7 open reading frame including the ATG start codon and has two Xho I sites at its 5' end.

(SEQUENCE ID. NO. 27)

5'-3': C CTC GAG CTC GAG GCC ATG GGC CAC ACA CGG AGO CAG GGA ACA TCA CCA TCC

The second primer corresponds to the anti-sense nucleotide sequence 1187 to 1149 of B7. This primer is complementary to the 3' region of the B7 open reading frame ending at the TAA stop codon and contains two Apa I restriction sites at the 5' end.

(SEQUENCE ID. NO. 28)

5'-3': C GGG CCC GGG CCC CTG TTA TAC AGG GCG TAC ACT TTC CCT TCT CAA TCT CTC

The 868 bp PCR product from the second PCR reaction is ligated into the pCR II plasmid, verified by DNA sequencing and transformed into frozen competent *E. coli* cells. This vector construct is designated pCR II Xh-A-B7 and verified by DNA sequencing.

G. Synthesis of Immunomodulatory Cofactor GM-CSF

The synthesis of GM-CSF is performed following the protocol of Foguet and Lubbert (*Biotechniques* 13:674–675, 1992). Briefly, ten overlapping oligonucleotides, 53 to 106 nucleotides in length, are synthesized. The first oligonucleotide is the sense sequence of human GM-CSF from nucleotide sequence number 29 to 86 containing two Hind III cleavage sites at the 5' end.

(SEQUENCE ID. NO. 29)

5'-3': GCA AGC TTA AGC TTG AGG ATG TGG CTG CAG AGC CTG CTG CTC TTG GGC ACT GTG GCC TGC AGC ATC TCT GCA

The second oligonucleotide is the sense sequence of human GM-CSF from the nucleotide sequence numbers 29 to 86 containing two Xho I sites at the 5' end.

(SEQUENCE ID. NO. 47)

5'-3': GC CTC GAG CTC GAG GAG GAT GTG GCT GCA GAG CCT GCT GCT CTT GGG CAC TGT GGC CTG CAG CAT CTC TGC A

The third oligonucleotide is the anti-sense sequence of human GM-CSF from nucleotide sequence number 145 to 70.

(SEQUENCE ID. NO. 30)

5'-3': TCC TGG ATG GCA TTC ACA TGC TCC CAG GGC TGC GTG CTG GGG CTG GGC GAG CGG GCG GGT GCA GAG ATG CTG CAG

The fourth oligonucleotide is the sense sequence of human GM-CSF from nucleotide number 131 to 191.

(SEQUENCE ID. NO. 31)

5'-3': GAA TGC CAT CCA GGA GGC CCG GCG TCT CCT GAA CCT GAG TAG AGA CAC TGC TGC TGA GAT G

The fifth oligonucleotide is the anti-sense sequence of human GM-CSF from nucleotide number 282 to 176.

(SEQUENCE ID. NO. 32)

5'-3': CTT GTA CAG CTC CAG GCG GGT CTG TAG GCA GGT CGG CTC CTG GAG GTC AAA CAT TTC TGA GAT GAC TTC TAC TGT TTC ATT CAT CTC AGC AGC AGT

The sixth oligonucleotide is the sense sequence of human GM-CSF from nucleotide number 256 to 346.

(SEQUENCE ID. NO. 33)

5'-3': CCT GGA GCT GTA CAA GCA GGG CCT GCG GGG CAG CCT CAC CAA GCT CAA GGG CCC CTT GAC CAT GAT GGC CAG CCA CTA CAA GCA GCA CTG

The seventh oligonucleotide sequence is the anti-sense sequence of human GM-CSF from nucleotide number 389 to 331.

(SEQUENCE ID. NO. 34)

5'-3': GGT GAT AAT CTG GGT TGC ACA GGA AGT TTC CGG GGT TGG AGG GCA GTG CTG CTT GTA G

The eighth oligonucleotide is the sense sequence of human GM-CSF from nucleotide number 372 to 431.

(SEQUENCE ID. NO. 35)

5'-3': CAA CCC AGA TTA TCA CCT TTG AAA GTT TCA AAG AGA ACC TGA AGO ACT TTC TGC TTG TC

The ninth oligonucleotide sequence is the anti-sense sequence of human GM-CSF from nucleotide number 520 to 416 containing two Xho I restriction sites at the 5' end.

(SEQUENCE ID. NO. 36)

5'-3': GC CTC GAG CTC GAG GTC TCA CTC CTG GAC TGG CTC CCA GCA GTC AAA GGG GAT GAC AAG CAG AAA GTC C

The tenth oligonucleotide sequence is identical to oligonucleotide number nine except that it contains two Xba I restriction sites at the 5' terminus instead of Xho I restriction sites.

(SEQUENCE ID. NO. 37)

5'-3': GC TCT AGA TCT AGA GTC TCA CTC CTG GAC TGG CTC CCA GCA GTC AAA GGG GAT GAC AAG CAG AAA GTC C

All the oligonucleotides except for oligonucleotide Sequence ID Nos. 29, 36, 37 and 47 are phosphorylated. Ligation is performed by mixing 8 pmol of each oligonucleotide and 7.5 µl 10×Sequenase Buffer (US Biochemical, Cleveland, Ohio) to a final volume of 75 µl with sterile distilled deionized $H_2O$. The reaction is heated for 5 minutes at 70° C., followed by 5 minutes at 48° C. Two microliters of dNTP mix (2.5 mM each dNTP) and 10 U Sequenase are added and incubated for 30 minutes at 37° C. To inactivate the Sequenase, the ligation reaction is heated for 10 minutes at 70° C. (*Current Protocols in Molecular Biology*, F. M. Asubel et al., 8.2.8–8.2.13, 1988).

One microliter of the ligation mixture is used in a PCR reaction with Vent polymerase (New England Biolabs, Beverly, Mass.) and the two oligonucleotides Sequence ID Nos. 29 and 36 as primers. The PCR product is ligated into the pCR II vector and transformed into frozen competent *E. coli* cells. This construct is designated pCR II H-Xh GM-CSF and verified by DNA sequencing.

One microliter of the ligation mixture was used in a second PCR reaction with Vent polymerase with the two oligonucleotides Sequence ID Nos. 47 and 37 as primers. The PCR product is ligated into the pCR II vector and transformed into frozen competent *E. coli* cells. This construct is designated pCR II Xh-Xb GM-CSF and verified by DNA sequencing.

H. Isolation of HBV Pre-S2 Open Reading Frame

The Pre-S2 open reading frame (including S) is PCR amplified with two primers and the pAM 6 plasmid (ATCC No. 45020) as the template. The sense primer corresponds to the nucleotides 3178 to 31 of the adw strain of hepatitis B virus, and includes the 5' region of the Pre-S2 open reading frame and the ATG start codon. The 5' end of this primer contains two consecutive Xho I restriction sites.

(SEQUENCE ID. NO. 48)

5'-3': GC CTC GAG CTC GAG GTC ATC CTC AGG CCA TGC AGT GGA ATT CCA CTG CCT TGC ACC AAG CTC TGC AGG

The second primer corresponds to the anti-sense nucleotide sequence 907 to 859, and is complementary to the 3' region of the Pre-S2 open reading frame. The 5' end of this primer contains two Cla I sites.

(SEQUENCE ID. NO. 49)

5'-3': GC ATC GAT ATC GAT GTT CCC CAA CTT CCA ATT ATG TAG CCC ATG AAG TTT AGG GAA TAA CCC C

The 957 bp PCR product is ligated into the pCR II plasmid, verified by DNA sequencing and designated pCR II HB-Pre-S2.

I. Isolation of HBV Polymerase Open Reading Frame

The PCR amplification is performed with two primers and the pAM 6 plasmid (ATCC 40202) as the template. The sense primer corresponds to the nucleotides 2309 to 2370 of the adw strain of hepatitis B virus, and includes the 5' region of the polymerase open reading frame with nucleotide changes to conform to the Kozak rules for translation. The 5' end of this primer contains two consecutive Xho I restriction sites.

(SEQUENCE ID. NO. 50)

5'-3': GC CTC GAG CTC GAG ACC ATG CCC CTA TCT TAT CAA CAC TTC CGG AAA CTA CTG TTG TTA GAC GAC GGG ACC GAG GCA GG

The second primer corresponds to the anti-sense nucleotide sequence 1645 to 1594, and is complementary to the 3' region of the polymerase open reading frame and includes the TGA stop codon. The 5' end of this primer contains two Cla I sites.

(SEQUENCE ID. NO. 51)

5'-3'GC ATC GAT ATC GAT GGG CAG GAT CTG ATG GGC GTT CAC GGT GGT CGC CAT GCA ACG TGC AGA GGT G

The 2564 bp PCR product is ligated into the pCR II plasmid, verified by DNA sequencing and designated pCR II HB-pol.

J. Isolation of HBV ORF 5 Open Reading Frame

The PCR amplification is performed with two primers and the pAM 6 plasmid (ATCC 45020) as the template. The sense primer corresponds to the nucleotides 1432 to 1482 of the adw strain of hepatitis B virus, and includes the 5' region of the ORF5 open reading frame with nucleotide changes to conform to the Kozak rules for translation. The 5' end of this primer contains two consecutive Xho I restriction sites.

(SEQUENCE ID. NO. 52)

5'-3': GC CTC GAG CTC GAG ACC ATG TCC CGT CGG CGC TGA ATC CCG CGG ACG ACC CCT CTC GGG GCC GCT TGG GAC

The second primer corresponds to the anti-sense nucleotide sequence 1697 to 1648, and contains two Cla I sites at the 5' end. This primer is complementary to the 3' region of the ORE 5 open rading frame and includes the TAA stop codon.

(SEQUENCE ID. NO. 53)

5'-3': GC ATC GAT ATC GAT GGT CGG TCG TTG ACA TTG CTG GGA GTC CAA GAG TCC TCT TAT GTA AGA CC

The 293 bp PCR product is ligated into the pCR II plasmid, verified by DNA sequencing and designated pCR II HB-ORF 5.

K. Isolation of HBV ORF 6 Open Reading Frame

The PCR amplification is performed with two primers and the pAM 6 plasmid (ATCC 45020) as the template. The sense primer corresponds to the nucleotides 1844 to 1788 of the adw strain of hepatitis B virus and includes the 5' region of the ORF6 open reading frame with nucleotide changes to conform to the Kozak rules for translation. The 5' end of this primer contains two consecutive Xho I restriction sites.

(SEQUENCE ID. NO. 54)

5'-3': GC CTC GAG CTC GAG ACC ATG ATT AGG CAG AGG TGA AAA AGT TGC ATG GTG CTG GTG CGC AGA CCA ATT TAT GCC

The second primer corresponds to the anti-sense nucleotide sequence 1188 to 1240, and contains two Cla I sites at the 5' end. This primer is complementary to the 3' region of the ORF 6 open reading frame and includes the TAA stop codon.

(SEQUENCE ID. NO. 55)

5'-3':GC ATC GAT ATC GAT GCT GAC GCA ACC CCC ACT GGC TGG GGC TTA GCC ATA GGC CAT CAG CGC ATG CG

The 687 bp PCR product is ligated into the pCR II plasmid, verified by DNA sequencing and designated pCR II HB-ORF 6.

L. Isolation of EMC IRES

The IRES from encephalomyocarditis virus is amplified by PCR from the pCITE-2a(+) plasmid (Novagen, Madison, Wis.) with two primers. The nucleotide sequence of the sense primer containing a Acc I restriction endonuclease site is:

(SEQUENCE ID. NO. 58)

5'-ATAGTCGACTTAATTCCGGTTATTTTCCACC-3'

The nucleotide sequence of the antisense primer containing a Cla I restriction endonuclease site is:
(SEQUENCE ID. NO. 59)

5'-GCCATCGATTTATCATCGTGTTTTTCAAAGO-3'

This 500 base pair PCR product is purified by electrophoresis through an 1.5% agarose gel and purified by Gene Clean II (Bio 101, Vista, Calif.) as described in Example 5B.

M. Isolation of IL-12 p40 Subunit

Normal uninfected human peripheral blood mononucleocytes (PBMC) are activated with *Staphylococcal aureas*. RNA from the stimulated PBMC is extracted and the IL-12 p40 subunit nucleotide sequence is amplified by PCR as described in Example 2C.

The sense primer corresponds to the nucleotides in the 5' region of the p40 subunit of IL-12 open reading frame and additionally contains Bgl II restriction endonuclease sites at the 5' end. The nucleotide sequence of this primer is:
(SEQUENCE ID. NO. 60)

5-GCAGATCTCCCAGAGCAAGATG-3'

The second primer corresponds to the antisense sequences 3' region of the p40 subunit of IL-12 open reading frame and additionally contains the Hpa I restriction endonuclease site at the 5' end. The nucleotide sequence of this primer is:
(SEQUENCE ID. NO. 61)

5'-GCGTTACCTGGGTCTATTCCGTTGTGTC-3'

The product of this PCR reaction is a Bgl II-Hpa I 1140 bp fragment encoding the p40 subunit of IL-12.

N. Isolation of IL-12 p35 Subunit

Normal uninfected PBMC are activated with Staphylococcal aureas. RNA from the stimulated PBMC is extracted and the IL-12 p35 subunit nucleotide sequence is amplified by PCR as described in Example 2C. The sense primer corresponds to the nucleotides in the 5' region of the p35 subunit of IL-12 open reading frame. The nucleotide sequence of this primer is:
(SEQUENCE ID. NO. 62)

5-GCAAGAGACCAGAGTCCC-3'

The second primer corresponds to the antisense sequences 3' region of the p35 subunit of IL-12 open reading frame. The nucleotide sequence of this primer is:
(SEQUENCE ID. NO. 63)

5'-GACAACGGTTTGGAGG-3'

Using a TA cloning kit (Invitrogen, San Diego, Calif.) the PCR amplified product is then ligated into the pCR II vector (Invitrogen, San Diego, Calif.)n and transformed into frozen competent *E. coli* cells. After verification by DNA sequencing, this construct is designated pCR II p35.

O. Site-Directed Mutagenesis to Generate F HBcore/neo$^R$

To generate a construct with a fusion between HBV core and neomycin phosphotransferase genes, PCR overlap extension was used where the termination codon of HBcore is deleted and fused in frame with the 11th amino acid of the neomycin phosphotransferase open reading frame. The KT-HB$_c$ plasmid is used as the template along with four oligonucleotides primers are used for the 3 PCR reactions performed to generate the fusion HBcore/neo$^R$ construct.

The first reaction utilizes two primers. The sense primer sequence corresponds to the Xho I restriction site at the 5' end of HB core gene.
(SEQUENCE ID. NO. 79)

5'-3': CTC GAG GCA CCA GCA CCA TG

The second primer sequence corresponds to the anti-sense nucleotide sequence 2457 to 2441 and 23 base pairs of neomycin phosphotransferase gene coding for codons 11–17.

(SEQUENCE ID. NO. 80)

5'-3': CTC TCC ACC CAA GCG GCC GGA GAA CAT TGA GAT TCC CGA G

The second reaction also utilizes the KT-HBc plasmid as the template and two primers. The sense primer corresponds to nucleotide sequence 2440 to 2457 and 23 base pairs of neomycin phosphotransferase gene coding for codons 11–17.
(SEQUENCE ID. NO. 81)

5'-3': CTC GGG AAT CTC AAT GTT CTC COG CCG CTT GGG TGG AGA G

The second primer corresponds to the anti-sense nucleotide sequence of the neomycin phosphotransferase gene.
(SEQUENCE ID. NO. 82)

5'-3': CGA TGC GAT GTT TCG CTT GG

The products of the first and second PCR reactions are extended in a third reaction to generate the F HBcore/neo$^R$ construct. Two primers are also utilized in the third reaction. The sense primer corresponds to the Xho I restriction site at the 5' end of the HBcore gene.
(SEQUENCE ID. NO. 79)

5'-3': CTC GAG GCA CCA GCA CCA TG

The second primer sequence corresponds to the anti-sense nucleotide sequence of the neomycin phosphotransferase gene.
(SEQUENCE ID. NO. 82)

5'-3': CGA TGC GAT GTT TCG CTT GG

The PCR product from the third reaction yields the fusion HBcore/neo$^R$ construct. Following the PCR reaction, the solution is transferred to a fresh 1.5 ml microfuge tube. Fifty microliters of 3 M sodium acetate is added to this solution followed by 500 µl of chloroform:isoamy alcohol (24:1). The mixture is vortexed and then centrifuged at 14,000 rpm for 5 minutes. The aqueous phase is transferred to a fresh microfuge tube and 1.0 ml 100% EtOH is added. This solution is incubated at −20° C. for 4.5 hours, and then centrifuged at 10,000 rpm for 20 minutes. The supernatant is decanted, and the pellet rinsed with 500 µl of 70% EtOH. The pellet is dried by centrifugation at 10,000 rpm under vacuum and then resuspended in 10 µl deionized $H_2O$. One microliter of the PCR product is analyzed by electrophoresis in a 1.0% agarose gel.

This PCR product, approximately 1.05 kb in length, is digested with Xho I and Pst I restriction endonucleases, electrophoresed through a 1.0% agarose gel and the DNA is purified from the gel slice by Geneclean II (Bio 101, Vista, Calif.).

This Xho I-Pst I PCR product is inserted into the respective sites of pBluescript KS+ II (Stratgene, La Jolla, Calif.). This construct is designated KSII+ Xh-Pst HB Fcore/neo$^R$, and is verified by DNA sequencing.

Example 3

A. Isolation of HBV X Antigen

A 642 bp Nco I-Taq I fragment containing the hepatitis B virus X open reading frame is obtained from the pAM6 plasmid (adw) (ATCC 45020), blunted by Klenow fragment, and ligated into the Hinc II site of SK$^+$ (Stratagene, La Jolla, Calif.).

*E. coli* (DH5 alpha, Bethesda Research Labs, Gaithersburg, Md.) is transformed with the ligation reaction and propagated. Miniprep DNA is then isolated and purified, essentially as described by Bimboim et al. (*Nuc. Acid Res.* 7:1513, 1979; *Molecular Cloning: A Laboratory Manual*, Sambrook et al. (eds.), Cold Spring Harbor Press, 1989).

Since this fragment can be inserted in either orientation, clones are selected that have the sense orientation with respect to the Xho I and Cla I sites in the SK$^+$ multicloning site. More specifically, miniprep DNAs are digested with the diagnostic restriction enzyme, Bain HI. Inserts in the correct orientation yield two fragments of 3.0 Kb and 0.6 Kb in size. Inserts in the incorrect orientation yield two fragments of 3.6 Kb and 0.74 Kb. A clone in the correct orientation is selected and designated SK-X Ag.

B. Truncation of HBV X Antigen

In order to generate truncated X antigen, TAG is inserted via a Nhe I (nonsense codon) linker (NEB#1060, New England BioLabs, Beverly, Mass.). This linker provides nonsense codons in all three reading frames.

SK-XAg is cleaved with Stu I (nucleotide 1704) which linearizes the plasmid. The Nhe I (nonsense codon) linkers are first phosphorylated in the following reaction. One $OD_{260}$ of linkers are dissolved in 100 μl TE (10 mM Tris-HCl pH 7.6, 1 mM EDTA). One microliter of linkers (1.0–2.0) is mixed with one μl of 10×buffer (0.66 M Tris-HCl pH 7.6, 10 mM ATP, 10 mM spermidine, 0.1 M $MgCl_2$, 150 mM DTT, 2 mg/ml BSA), 6 μl $H_2O$ and 2 U of T4 DNA kinase and incubated for 1 hour at 37° C. This reaction mixture is then added to 0.4 μg of linearized SK XAg plasmid (Example 3A) in 10 μl of the above buffer with 10 units of T4 DNA ligase. The reaction is incubated at 22° C. for 6 hours and stopped with 1 μl of 0.5 M EDTA. The reaction is then extracted with phenol:chloroform (a 1:1 ratio), and the DNA is precipitated with ethanol. The DNA is recovered by centrifugation at 14,000 rpm for 5 minutes at room temperature. The pellet is then dried and dissolved in 90 μl of TE (10 mM Tris-HCl pH 7.6, 1 mM EDTA). Ten microliters of 10×NeB2 buffer (New England Biolabs, Beverly, Mass.) is added to the DNA and then digested with 20 U of Nhe I. The plasmid is purified from excess linkers by 1.0% agarose gel electrophoresis, and isolated by Geneclean II (Bio 101, Vista, Calif.).

The DNA is self-ligated and transformed onto competent E. coli. Clones are then screened for the presence of the diagnostic restriction site, Nhe I; these clones will contain the truncated X gene. A clone is selected and designated SK-TXAg.

Example 4

PREPARATION OF VECTOR CONSTRUCT BACKBONE

A. Preparation of Retroviral Backbone KT-3

The Moloney murine leukemia virus (MoMLV) 5' long terminal repeat (LTR) EcoR I-EcoR I fragment, including gag sequences, from the N2 vector (Armentano et al., J. Vir. 61:1647–1650, 1987; Eglitas et al., Science 230:1395–1398, 1985) is ligated into the plasmid $SK^+$ (Stratagene, La Jolla, Calif.). The resulting construct is designated N2R5. The N2R5 construct is mutated by site-directed in vitro mutagenesis to change the ATG start codon to ATT preventing gag expression. This mutagenized fragment is 200 bp in length and flanked by Pst I restriction sites. The Pst I-Pst I mutated fragment is purified from the $SK^+$ plasmid and inserted into the Pst I site of N2 MoMLV 5' LTR in plasmid pUC31 to replace the non-mutated 200 bp fragment. The plasmid pUC31 is derived from pUC19 (Stratagene, La Jolla, Calif.) in which additional restriction sites Xho I, Bgl II, BssH II and Nco I are inserted between the EcoR I and Sac I sites of the polylinker. This construct is designated pUC31/N2R5gM.

A 1.0 Kb MoMLV 3' LTR EcoR I-EcoR I fragment from N2 is cloned into plasmid $SK^+$ resulting in a construct designated N2R3-. A 1.0 Kb Cla I-Hind III fragment is purified from this construct.

The Cla I-Cla I dominant selectable marker gene fragment from pAFVXM retroviral vector (Kriegler et al., Cell 38:483, 1984; St. Louis et al., PNAS 85:3150–3154, 1988), comprising a SV40 early promoter driving expression of the neomycin phosphotransferase gene, is cloned into the $SK^+$ plasmid. This construct is designated $SK^+$ $SV_2$-neo A 1.3 Kb Cla I-BstB I gene fragment is purified from the $SK^+$ $SV_2$-neo plasmid.

The KT-3 retroviral vector is constructed by a three part ligation in which the Xho I-Cla I fragment containing the gene of interest and the 1.0 Kb MoMLV 3' LTR Cla I-Hind III fragment are inserted into the Xho I-Hind III site of pUC31/N2R5gM plasmid. The 1.3 Kb Cla I-BstB I neo gene fragment from the pAFVXM retroviral vector is then inserted into the Cla I site of this plasmid in the sense orientation.

B. Preparation of Retroviral Backbone KT-1

The KT-1 retroviral backbone vector is constructed essentially as described for KT-3 in Example 4A, with the exception that the dominant selectable marker gene, neo, is not inserted into the expression vector. Specifically, in a three part ligation, the Xho I-Cla I fragment containing the gene of interest and the 1.0 Kb MoMLV 3' LTR Cla I-Hind III fragment are inserted into the Xho I-Hind III site of pUC31/N2R5gM plasmid.

C. Preparation of Retroviral Backbone JMR-2

The JMR-2 vector is comprised of the KT-3 retrovector with a polylinker containing a Xho I, Bam HI, Srf I, and Not I restriction endonuclease sites at the Xho I site of KT-3 flanking the 5' end of the encephalomyocarditis virus IRES (Novagen, Madison, Wis.) and a polylinker containing a Cla I, Bgl II, Age I, Hpa I, Mlu I, and Sal I restriction endonuclease sites flanking the 3' end of the encephalomyocarditis virus IRES.

Briefly, the JMR-2 vector is prepared by inserting a linker containing the Xho I, Bam HI, Srf I, Not I, Cia I and Sal I restriction endonuclease sites at the Xho I restriction endonuclease sites of the KT-3 backbone as described in Example 3B. This construct is designated KT3-L1 and verified by DNA sequencing. The sense and antisense strands are synthesized by standard methods of DNA synthesis. The sense strand sequence is:

(SEQUENCE ID NO. 64)

5'-TCG AGG ATC CGC CCG GGC GGC CGC ATC GAT GTC GAC G-3'

The antisense strand sequence is:

(SEQUENCE ID NO. 65)

5'-CGC GTC GAC ATC GAT GCG GCC GCC COG GCG GAT CC-3'

These oligonucleotides are annealed at 37° C., generating 5' overhangs. These double stranded linkers are then hybridized to compatible overhangs of the Xho I digested KT-3 backbone by annealing at 37° C., followed by ligation.

The IRES from encephalomyocarditis virus is excised by digestion with Acc I and Cla I restriction endonucleases of the PCR amplified product (Example 2C) and ligated into the Cla I sites of the KT3-L1 and designated KT3-L1-IRES. The correct orientation of the IRES is determined after analysis with AvrII endonuclease digestion. The multicloning site containing Cla I, Bgl II, Age I, Hpa I, Mlu I, and Sal I restriction endonucleases is then inserted into the Cla I-Sal I sites of KT3-L1-IRES. The resulting vector is designated JMR-2. The sense and antisense strands are synthesized by standard methods of DNA synthesis. The sense strand sequence is:

(SEQUENCE ID NO. 66)

5'-CGA TAG ATC TAC CGG TTA ACG CG-3'

The antisense strand sequence is:

(SEQUENCE ID NO. 83)

5'-TCG ACG CGT TAA CCG GTA GAT CTA T-3'

These oligonucleotides are annealed at 37° C., generating 5' overhangs. These double stranded linkers are then hybridized to compatible overhangs of the Cla I-Sal I digested KT3-L1IRES backbone by annealing at 37° C., followed by ligation.

D. Preparation of CMV Expression Vector

Plasmid pSCV6 (as described in U.S. Pat. Ser. No. 07/800,921) may be utilized to generate pCMV-HBc. Briefly, the pSCV6 plasmid is derived from the pBluescript SK– backbone (Stratagene, La Jolla, Calif.) with the CMV IE promoter followed by a polylinker site allowing insertion of a gene of interest and ending with a SV40 poly A Signal.

E. Preparation of Adenovirus Viral Backbone

The adenovirus vector backbone, the pAdM1 plasmid is obtained from Quantum Biotechnologies (Montreal, Canada). The Ad5delta E1delta E3 plasmid (Gluzman et al., in *Eucaryotic Viral Vectors*, pp. 187–192, Cold Spring Harbor, 1982) is also obtained from Quantum Biotechnologies.

Example 5

CONSTRUCTION OF VIRAL AND EXPRESSION VECTOR

A. Construction of Hepatitis B Virus e Retroviral Vector

The 787 bp Xho I-Cla I fragment from $SK^+$ HBe-c, Example 2A, is then ligated into the Xho I and Cla I sites of the KT-3 retroviral vector backbone. This construct is designated KT-HBe-c.

B. Construction of Hepatitis B Virus core Retroviral Vector

The PCR product from Example 2B, approximately 600 bp in length, is digested with Xho I and Cla I restriction endonucleases, electrophoresed through an 1.5% agarose gel and the DNA is purified from the gel slice by Geneclean II (Bio 101, Vista, Calif.). This Xho I-Cla I HBV core PCR product is inserted into the Xho I and Cla I sites of the KT-3 retroviral vector backbone. The construct is designated KT-HBc.

The HBV core fragment (Xho I-Cla I) from KT-HBc is inserted into the respective sites of pBluescript $KS^+$ II (Stratagene, La Jolla, Calif.). This construct is designated $KS^+$ II HBc, and is verified by DNA sequencing.

C. Construction of Hepatitis C Virus core Retroviral Vector (i) Construction of KT-HCc The Xho I-Hind III fragment from pCR II Xh-H HCV core from Example 2C is inserted into the respective sites of pSP72. This construct is designated pSP72 Xh-H HCc. The Xho I-Cla I fragment from pSP72 Xh-H HCc is then excised and inserted into the KT-3 backbone. This construct is designated KT-HCc.

(ii) Construction of Hepatitis C Virus core-E1 Retroviral Vector

The plasmid $pTM1CE1_{330}$ was digested with Apa L1, blunt-ended, and then digested with Bam H1. The resulting 1.089 Kb (Apa L1 blunt)/Bam H1 $CE1_{330}$ fragment was isolated. Plasmid K3L1 was derived from the KT3 retroviral vector backbone (Example 4A) and contains a polylinker insert consisting of the following restriction sites: Xho 1/Bam H1/Srf 1/Not 1/Cla 1/Sal/1). K3L1 was digested with Xho 1, blunt-ended, and then digested with Bam H1. The resulting 6.6 Kb (Xho 1 blunt)/Bam H1 retroviral vector backbone fragment was isolated. The 1.089 Kb blunt-end/Bam H1 $CE_{330}$ fragment was ligated to the 6.6 Kb blunt-end/Bam H1 retroviral vector backbone fragment to generate the vector encoding HCV $CE1_{330}$, driven by MoMLV LTR, and $neo^r$, driven by the SV40 promoter. The resulting plasmid was named $K3L1-CE1_{330}$ (see FIG. 17).

(iii) Construction of Hepatitis C Virus core-E1-E2 Retroviral Vector

The plasmid pEE14 $CE1E2_{715}$ was digested with ApaL1, blunt-ended, and then digested with Not 1. The resulting 2.161 Kb (Apa L1 blunt)/Not 1 $CE1E2_{715}$ fragment was isolated. Plasmid K3L1 was derived from the KT3 retroviral vector backbone (Example 4A) and contains a polylinker insert consisting of the following restriction sites: Xho 1/Bam H1/Srf 1/Not 1/Cla 1/Sal/1). K3L1 was digested with Srf 1 and Not 1, and the resulting 6.6 Kb Srf 1/Not 1 retroviral vector backbone fragment was isolated. The 2.161 Kb blunt-end/Not $1CE1E2_{715}$ fragment was ligated to the 6.6 Kb Srf 1/Not 1 retroviral vector backbone fragment to generate the vector encoding HCV $CE1E2_{715}$, driven by MoMLV LTR, and $neo^r$, driven by the SV 40 promoter. The resulting plasmid was named $K3L1-CE1E2_{715}$ (see FIG. 17).

D. Construction of Hepatitis C Virus NS3/NS4 Retroviral Vectors

The Xho I-Hind III fragment from pCR II Xh-H HCV NS3/NS4 from Example 2D is inserted into the respective sites of pSP72. This construct is designated pSP72 Xh-H HCV NS3/NS4. The Xho I-Cla I fragment from pSP72 Xh-H HCV NS3/NS4 is then excised and inserted into the KT-3 backbone. This construct is designated KT-HCV NS3/NS4.

E. Construction of Hepatitis B Virus X Retroviral Vector

The Xho I-Cla I fragment from SK-X Ag is excised and inserted into the respective sites of the KT-3 backbone. This construct is designated KT-HB-X.

F. Construction of Hepatitis B Virus Truncated X Retroviral Vector

The Xho I-Cla I fragment from SK-TX Ag is excised and inserted into the respective sites of the KT-3 backbone. This construct is designated KT HB-TX.

G. Construction of Hepatitis B Virus Pre-S2 Retroviral Vector

The Xho I-Cla I fragment from pCR II HB-Pre-S2 from Example 2H is excised and inserted into the respective sites of the KT3 backbone. This construct is designated KT-HB-Pre-S2.

H. Construction of Hepatitis B Virus Polymerase Retroviral Vector

The Xho I-Cla I fragment from pCR II HB-pol from Example 2I is excised and inserted into the respective sites of the KT3 backbone. This construct is designated KT-HB-pol.

I. Construction of Hepatitis B Virus ORF 5 Retroviral Vector

The Xho I-Cla I fragment from pCR II HB-ORF5 from Example 2J is excised and inserted into the respective sites of the KT3 backbone. This construct is designated KT-HB-ORF 5.

J. Construction of Hepatitis B Virus ORF 6 Retroviral Vector

The Xho I-Cla I fragment from pCR II HB-ORF6 from Example 2K is excised and inserted into the respective sites of the KT3 backbone. This construct is designated KT-HB-ORF 6.

K. Construction of Hepatitis B Virus e/Thymidine Kinase Retroviral Vector

The Xho I to Cla I HBV e from KT-HBe-c (Example 5A) is ligated into the Xho I/Cla I site of the KT-1 retroviral vector backbone (Example 4B) resulting in a vector designated KT-1/HBe-c. A 2.0 Kb Cla I/Cla I fragment containing the HSV-1 thymidine kinase gene driven by the thymidine kinase promoter is derived from pSP72-TK/Cla, and ligated into the Cla I/Cla I site of KT-1/HBe-c in the sense orientation. Orientation is determined by Sma I digestion. This construct is designated KT-HBe/TK.

pSP72-TK/Cla is derived as follows. The fragment containing the HSV-1 thymidine kinase promoter and gene is excised by Xho I and Bam HI digestion from PrTKdeltaA. (PrTKdeltaA is described in Example 4 of PCT WO 91/02805.) This fragment is isolated from a 1% agarose gel with NA45 paper as described in Example 2A and inserted into the Xho I and Bam HI sites of pSP72 plasmid. This plasmid is designated pSP72-TK. pSP72TK is linearized with Xho I, blunted with Klenow and ligated with Cla I linkers (New England BioLabs, Beverly, Mass.) as described in Example 3B. This plasmid is self-ligated and transformed onto competent *E. coli*. A clone is selected and designated pSP72-TK/Cla.

L. Construction of Hepatitis B Virus core/Thymidine Kinase Retroviral Vector

The Xho I to Cla I HBV core fragment from KT-HBc (Example 5B) is ligated into the Xho I/Cla I site of the KT-1 retroviral vector backbone (Example 4B) resulting in vectors designated KT-1/HBc. A 2.0 Kb Cla I/Cla I fragment containing the HSV-1 thymidine kinase gene driven by the thymidine kinase promoter is derived from pSP72-TK/Cla and ligated into the Cla I/Cla I site of KT-1/HBc in the sense orientation. This construct is designated KT-HBc/TK.

M. Construction of Hepatitis B Virus Core CMV Expression Vector

The HBV core fragment is obtained from the construct KT-HBc (Example 5B) by digestion of the plasmid with Xho I and Cla I restriction enzymes and isolation from a 1% agarose gel with NA45 paper as described in Example 2A. The fragment is blunted with Klenow and ligated into the Sma I site of the plasmid pSC6. Orientation of the HBcore gene is determined by Eco RI/SSpI double digest. This plasmid is designated pCMV-HBc. *E. coli* (DH5 alpha, Bethesda Research Labs, Gaithersburg, Md.) is transformed with the pCMV-HBc plasmid and propagated to generate plasmid DNA. The plasmid DNA is then isolated and purified by cesium chloride banding and ethanol precipitation essentially as described by Bimboim et al. (*Nuc. Acid Res.* 7:1513, 1979; see also "Molecular Cloning: A Laboratory Manual," Sambrook et al. (eds.), Cold Spring harbor Press, 1989). The DNA is resuspended in 0.9% sterile phosphate-buffered saline at a final concentration of 2 mg/ml.

N. Construction of Hepatatis B Virus e Adenovirus Viral Vector

The Xho I to Cla I HBV e fragment is obtained from KT-HBe-c (Example 5A) by digestion of the plasmid with Xho I and Cla I restriction enzymes and isolation on a 1% agarose gel and NA45 paper as described in Example 2A. The fragment is blunted with Klenow fragment. The adenovirus vector backbone, the pAdM1 plasmid, is cleaved with Bam HI and blunted with Klenow fragment. The blunted HBV e fragent is ligated into the blunted Bam HI site of pAdM1 plasmid. Orientation of the HBV e gene is determined by Eco RI/Ssp I double digestion. This plasmid is designated pAdM1-HBe.

O. Construction of HB Fcore/neo$^R$ Retroviral Vector

Three fragments are purified for the construction of the HB Fcore/neo$^R$ retroviral vector. First, KT-HBc (from Example 5) is digested with Cla I, Pst I and Hind III, and the 1.6 kb Pst I-Hind III fragment containing the neomycin phosphotransferase gene and the 3' LTR is isolated. Second, from KSII+ Xh-Pst HB Fcore/neo$^R$ (Example 2), the 1.05 kb Xho I-Pst I fragment is isolated. Third, from KT-HBc, the 4.3 kb Xho I-Hind III fragment containing the vector backbone is isolated. In a three-part ligation, the Xho I-Pst I fragment containing the HB Fcore/neo$^R$ fragment and the Pst I-Hind III neo/3' LTR fragment are inserted into the Xho I-Hind III sites of KT-HBc. This vector construct is designated KT-HB Fcore/neo$^R$.

Example 6

CONSTRUCTION OF MULTIVALENT RETROVIRAL VECTOR

A. Construction of Hepatitis B e/GM-CSF Retroviral Vector
 i. Multivalent Retroviral Vector with BIP IRES pGEM 5Z+ BIP 5' (Peter Samow, University of Colorado, Health Sciences Center, Denver, human immunoglobulin heavy chain binding protein) is digested with Sac I and Sph I. The 250 bp BIP fragment is isolate by 1.5% agarose gel electrophoresis and subcloned into the respective sites of pSP72. The vector construct is designated pSP72 BIP.

The Hind III-Xho I GM-CSF fragment is excised from pCR II H-Xh GM-CSF of Example 2G, and subcloned into the Hind III-Xho I sites of pSP72 BIP. This construct is designated pSP72 BIP-GM-CSF.

The construct pSP72 BIP GM-CSF is cleaved at the Xho I site and blunted by Klenow fragment, followed by cleavage with Cla I. The KT-1 backbone is cleaved by Cla I and blunted with Klenow fragment followed by cleavage with Xho I restriction endonuclease. In a three-part ligation, the Xho I-Cla I fragment from SK+ HBe-c, Example 2A, and the Cla I-blunted Xho I BIP-GM-CSF fragment is ligated into the Xho I-blunted Cla I sites of the KT-1 retroviral backbone. This construct is designated KT-HBe-c/BIP-GM-CSF.

ii. Multivalent Retroviral Vector with CMV Promoter

The 4.7 Kb CMV Env$^R$ Pst-RI fragment is isolated from pAF/CMV/Env$^R$ (U.S. patent application Ser. No. 07/395, 932), and inserted into the Pst I and Eco RI sites of pUC 18. This construct is designated pUC 18 CMV Env$^R$.

HIV-1 III$_B$ CAR is subeloned as a Sau 3A fragment from pAF/CMV/Env$^R$ into the BamH I site of pBluescript II KS+ (Stratagene, La Jolla, Calif.) to generate pBluescript II KS+/CAR. The CAR fragment is excised from pBluescript II KS+/CAR as a Xba I-Cla I fragment. The Xho I-Xba I HIV-1 III$_B$ gag/pol fragment is excised from SK+ gag/pol SD delta (U.S. patent application Ser. No. 07/395,932). The plasmid backbone containing the CMV promoter is excised from pUC18 CMV/Env$^R$ with Xho I and Cla I. In a three part ligation, the Xho I-Xba I HIV IIIB gag-pol fragment and the Xba I-Cla I CAR fragment is inserted into the Xho I-Cla I sites of the pUC 18 CMV/Env$^R$ backbone to generate pUC 18 CMV gag/pol/CAR.

The Hind III-Xho I fragment containing the CMV IE promoter from pUC 18 CMV-gag/pol/CAR is subcloned into the respective sites of pCDNA II. This construct is designated pCDNA II CMV.

The Xho I-Xba I GM-CSF PCR product is subcloned from the pCR II Xh-Xb GM-CSF of Example 2G and inserted into the respective sites within pCDNA II-CMV. This construct is designated pCDNA II CMV-GM-CSF.

The pCDNA II CMV GM-CSF construct is cleaved at the Xba I site, blunted by Klenow fragment, followed by cleavage with Hind III. The KT-1 backbone is cleaved by Cla I and blunted with Klenow fragment followed by cleavage with Xho I. In a three-part ligation, the Xho I-Hind III fragment from SK+ HBe-c, Example 2A, and the Hind III-blunted Xba I CMV-GM-CSF fragment is ligated into the Xho I-blunted Cla I sites of the KT-1 retroviral backbone. This vector construct is designated KT-HBe-c/CMV-GM-CSF.

B. Construction of Hepatitis C core/IL-2 Retroviral Vector
 i. Multivalent Retroviral Vector with IRES The Hind III-Xho I IL-2 sequence is excised from pCR II H-Xh IL-2 of Example 2E, and subcloned into the Hind III-Xho I sites of pSP72 BIP. This construct is designated pSP72 BIP IL-2. The Xho I-Hind III hepatitis C virus core sequence, Example 2C, is excised from pCRII Xh-H HCV C core and subcloned into the respective sites of pSP72. This construct is designated pSP72 Xh-H HCV core.

The construct pSP72 BIP-IL2 is cleaved at the Xho I site, blunted by Klenow fragment followed by cleavage with Eco RI. The Xho I-Eco RI HCV core fragment is isolated from pSP72 Xh-H HCV core. The KT-1 backbone is cleaved by Cla I and blunted with Klenow fragment followed by cleavage with Xho I. In a three-part ligation, the Xho I-Eco RI HCV core fragment and the Eco RI-blunted Xho I BIP-IL2 fragment is ligated into the Xho I-blunted Cla I sites of the KT-1 retroviral backbone. This vector construct is designated KT-HCV core/BIP-IL2.

ii. Multivalent Retroviral Vector with CMV Promoter

The Xho I-Apa I IL-2 fragment is excised from pCR II Xh-A IL-2 of Example 2E, and subcloned into the respective sites of pCDNA II-CMV promoter. This construct is designated pCDNA II CMV-IL-2.

The KT-1 backbone is cleaved by Cla I and blunted with Klenow fragment followed by cleavage with Xho I. The construct pCDNA II CMV-IL-2 is cleaved at the Apa I site, blunted by Klenow fragment and followed by cleavage with Hind III restriction endonuclease. In a three-part ligation, the Xho I-Hind III HCV core fragment from pCR II Xh-H HCV core from Example 2C and the Hind III-blunted Apa I CMV IL-2 fragment is ligated into the Xho I-blunted Cla I sites of the KT-1 retroviral backbone. This vector construct is designated KT-HCV core/CMV IL-2.

C. Construction of Hepatitis B core/B7 Retroviral Vector i. Multivalent Retroviral Vector with IRES The Hind III-Xho I B7 sequence is excised from pCR II H-Xh B7 of Example 2F, and subcloned into the Hind III-Xho I sites of pSP72 BIP. This construct is designated pSP72 H-Xh BIP-B7.

Figure 8:
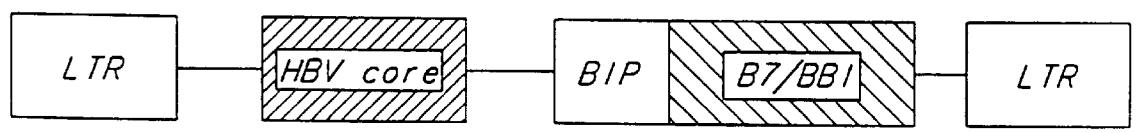
FIG. 8 is a diagrammatic representation of vector construct KT-HBV core/B7 which expresses both HBV core and B7 proteins.

The construct pSP72 H-Xh BIP-B7 is cleaved at the Xho I site, blunted by Klenow fragment followed by cleavage with Cla I. The Xho I-Cla I HBV core fragment is isolated from KS II⁺ HBc, Example 5B. The KT-1 backbone is cleaved by Cla I and blunted with Klenow fragment followed by cleavage with Xho I. In a three-part ligation, the Xho I-Cla I HBV core fragment and the Cla I-blunted Xho I BIP-B7 fragment is ligated into the Xho I-blunted Cla I sites of the KT-1 retroviral backbone. This vector construct is designated KT-HBV core/BIP-B7 (see FIG. 8).

ii. Multivalent Retroviral Vector with CMV Promoter

The Xho I-Apa I B7 sequence is excised from pCR II Xh-A B7 of Example 2F, and subcloned into the respective sites of pCDA II-CMV promoter. This construct is designated pCDNA II CMV-B7.

The KT-1 backbone is cleaved by Cla I and blunted with Klenow fragment followed by cleavage with Xho I. The construct pCDNA II CMV-B7 is cleaved at the Apa I site blunted by Klenow fragment and followed by cleavage with Hind III restriction endonuclease. In a three-part ligation, the Xho I-Hind III HBV core fragment from KS II⁺ HBc, and the Hind III-blunted Apa I CMV B7 fragment is ligated into the Xho I-blunted Cla I sites of the KT-1 retrovital backbone. This vector construct is designated KT-HBc/CMU-B7.

D. Construction of Hepatitis B e/Hepatitis C core Retroviral Vector i. Multivalent Retroviral Vector with BIP IRES The Hind III-Xho I HCV core PCR product is subcloned from the pCR II H-Xh HCV core, Example 2C, and inserted into the respective sites within pSP72-BIP. This construct is designated pSP72 BIP-HCV core.

The construct pSP72 BIP-HCV core is cleaved at the Xho I site, blunted by Klenow fragment, followed by cleavage with Cla I. The KT-1 backbone is cleaved by Cla I and blunted with Klenow fragment followed by cleavage with Xho I. In a three part ligation, the Xho I-Cla I HBV e fragment from SK⁺ HBe-c, Example 2A, and the Cla I-blunted Xho I BIP HCV core fragment is ligated into the Xho I-blunted Cla I sites of the KT-1 retroviral backbone. This vector construct is designated KT-HBV e/BIP HCV core.

ii. Multivalent Retroviral Vector with CMV Promoter

The Xho I-Xba I HCV core fragment from pSP72 Xh-H HCV core (Example 6B i) is inserted into the respective sites of pCDNA II CMV plasmid. This construct is designated pCDNA II CMV HCV core.

The construct pCDNA II CMV HCV core is cleaved at the Xba I site, blunted by Klenow fragment, followed by cleavage with Hind III. The KT-1 backbone is cleaved by Cla I and blunted with Klenow fragment followed by cleavage with Xho I. In a three part ligation, the Xho I-Hind III HBV e sequence from SK⁺ HBe-c, Example 2A, the Hind III-blunted Xba I CMV HCV core fragment is ligated into the Xho I-blunted Cla I sites of the KT-1 retroviral backbone. This vector construct is designated KT-HBVe/CMV HCV core.

E. Construction of Hepatitis B Virus Core/IL-12 Retroviral Vector

The Xho I-Not I HBV core fragment is isolated from KS II + HBc, Example 5B, and subcloned into the Xho I-Not I sites of the JMR-2. This construct is designated JMR-2 HBc.

The Bgl II-Hpa I p40 PCR fragment is then subcloiied into the respective sites of JMR-2 HBc. This construct is designated JMR-2 HBc/p40.

The Xho I-Nsi I p35 fragment is then excised from pCR II p35 and subcloned into the respective sites of pCDA II-CMV, Example 6Ai. This construct is designated pCDNA II CMV-p35.

The pCDNA II CMV-p35 is excised with Nsi I and blunt ended with T4 DNA polymerase (New England Biolabs, Beverly, Mass.). The Nsi I-blunt ended CMV p35 fragment is ligated into the Sal I-blunt ended sites of the JMR-2 HBc/p40. Restriction digests are used to confirm that only one fragment is inserted in the correct orientation. This retrovector construct is designated JMR-2 HBc/p40/CMV-p35.

Example 7

TRANSIENT TRANSFECTION AND TRANSDUCTION OF PACKAGING CELL LINES HX AND DA

A. Generation of Producer Cell Line Via Two Packaging Cell Lines

HX cells (WO 92/05266) are seeded at $5 \times 10^5$ cells on a 10 cm tissue culture dish on day 1 with Dulbecco's Modified Eagle Medium (DMEM) and 10% Fetal Bovine Serum (FBS). On day 2, the media is replaced with 5.0 ml fresh media 4 hours prior to transfection. A standard calcium phosphate-DNA co-precipitation is performed by mixing 40.0 µl 2.5 M $CaCl_2$, 10 µg plasmid DNA and deionized $H_2O$ to a total volume of 400 µl. Four hundred microliters of the DNA-$CaCl_2$ solution is added dropwise with constant agitation to 400 µl precipitation buffer (50 mM HEPES-NaOH, pH 7.1, 0.25 M NaCl and 1.5 mM $Na_2HPO_4$—$NaH_2PO_4$). This mixture is incubated at room temperature for 10 minutes. The resultant fine precipitate is added to a culture dish of cells. The cells are incubated with the DNA precipitate overnight at 37° C. On day 3 the media is aspirated and fresh media is added. The supernatant containing virus is removed on day 4, passed through a 0.45µ filter and used to infect the DA packaging cell line, murine fibroblasts or stored at −80° C.

DA (WO 92/05266) cells are seeded at $5 \times 10^5$ cells/10 cm tissue culture dish in 10 ml DMEM and 10% FBS, 4 µg/ml polybrene (Sigma, St. Louis, Mo.) on day 1. On day 2, 3.0 ml, 1.0 ml and 0.2 ml of the freshly collected virus containing DX media is added to the cells. The cells are incubated with the virus overnight at 37° C. On day 3 the media is removed and 1.0 ml DMEM, 10% FBS with 800 µg/ml G418 is added to the plate. Only cells that have been transduced with the vector and contain the neo selectable marker will survive. A G418 resistant pool is generated over a period of a week. The pool is tested for expression as described (Example 12A). The pool of cells is dilution cloned by removing the cells from the plate and counting the cell suspension, diluting the cells suspension down to 10 cells/ml and adding 0.1 ml to each well (1 cell/well) of a 96 well plate (Corning, Corning, N.Y.). Cells are incubated for 14 days at 37° C., 10% $CO_2$. Twenty-four clones are selected and expanded up to 24 well plates, 6 well plates then 10 cm plates at which time the clones are assayed for expression and the supernatants are collected and assayed for viral titer.

The packaging cell line HX (WO 92/05266), is transduced with vector generated from the DA vector producing cell line in the same manner as described for transduction of the DA cells from HX supernatant.

For transduction of the DA (WO 92/05266) cells with a multivalent vector, lacking a neo selectable marker, the infection procedure as noted above is used. However, instead of adding G418 to the cells on day 3, the cells are cloned by limiting dilution as explained above. Fifty clones are expanded for expression as explained above, and titer assayed as described in Example 8.

The packaging cell line 293 2–3 (WO 92/05266) can also be utilized as the initial cell line in the generation of a producer cell line via two packaging cell lines. Briefly, 293 2–3 cells are seeded at $5\times10^5$ cells on a 10 cm tissue culture dish on day 1 with Dulbecco's Modified Eagle Medium (DMEM) and 10% Fetal Bovine Serum (FBS). On day 2, the media is replaced with 5.0 ml fresh media 4 hours prior to transfection. A standard calcium phosphate-DNA co-precipitation is performed by mixing 40.0 ul 2.5 M $CaCl_2$, 10 ug MLP-G plasmid DNA (U.S. Ser. No. 08/368,574), 10 ug KT3L1-CE1E2$_{715}$ and deionized $H_2O$ to a total volume of 400 ul. Four hundred microliters of the DNA-$CaCl_2$ solution is added dropwise with constant agitation to 400 ml precipitation buffer (50 mM HEPES-NaOH, pH 7.1, 0.25 M NaCl and 1.5 mM $Na_2HPO_4$—$NaH_2PO_4$). This mixture is incubated at room temperature for 10 minutes. The resultant fine precipitate is added to a culture dish of cells. The cells are incubated with the DNA precipitate overnight at 37° C. On day 3 the media is aspirated and fresh media is added. The supernatant containing virus is removed on day 4, passed through a 0.45 m filter and used to infect the DA packaging cell line, murine fibroblasts or stored at −80° C.

B. Generation of Producer Cell Line Via One Packaging Cell Line

DA cells (WO 92/05266) are seeded at $5\times10^5$ cells on a 10 cm tissue culture dish on day 1 with Dulbecco's Modified Eagle Medium (DMEM) and 10% irradiated (2.5 megarads minimum) fetal bovine serum (FBS). On day 2, the media is replaced with 5.0 ml fresh media 4 hours prior to transfection. A standard calcium phosphate-DNA coprecipitation is performed by mixing 60 μl 2.0 M $CaCl_2$, 10 μg MLP-G plasmid, 10 μg KT-HBe-c or KT-HBc retroviral vector plasmid, and deionized water to a volume of 400 μl. Four hundred microliters of the DNA-$CaCl_2$ solution is added dropwise with constant agitation to 400 μl 2xprecipitation buffer (50 mM HEPES-NaOH, pH 7.1, 0.25 M NaCl and 1.5 mM $Na_2HPO_4$—$NaH_2PO_4$). This mixture is incubated at room temperature for 10 minutes. The resultant fine precipitate is added to a culture dish of DA cells plated the previous day. The cells are incubated with the DNA precipitate overnight at 37° C. On day 3 the medium is removed and fresh medium is added. The supernatant containing G-pseudotyped virus is removed on day 4, passed through a 0.45μ filter and used to infect the DA packaging cell.

DA cells (WO 92/05266) are seeded at $5\times10^5$ cells on a 10 cm tissue culture dish in 10 ml DMEM and 10% FBS, 4 μg/ml polybrene (Sigma, St. Louis, Mo.) on day 1. On day 2, 2.0 ml, 1.0 ml or 0.5 ml of the freshly collected and filtered G-pseudotyped virus containing supernatant is added to the cells. The cells are incubated with the virus overnight at 37° C. On day 3 the medium is removed and 10 ml DMEM, 10% irradiated FBS with 800 μg/ml G418 is added to the plate. Only cells that have been transduced with the vector and contain the neo selectable marker will survive. A G418 resistant pool is generated over the period of 1–2 weeks. The pool is tested for expression as described in Example 12A. The pool of cells is dilution cloned by removing the cells from the plate, counting the cell suspension, diluting the cell suspension down to 10 cells/ml and adding 0.1 ml to each well (1 cell/well) of a 96-well plate (Corning, Corning, N.Y.). Cells are incubated for 2 weeks at 37° C., 10% $CO_2$. Twenty-four clones are selected and expanded up to 24-well plates, then 6-well plates, and finally 10 cm plates, at which time the clones are assayed for expression and the supernatants are collected and assayed for viral titer.

Example 8

TITERING OF RETROVIRAL VECTORS

A. Titering of Vectors With Selectable Marker

The titer of the individual clones is determined by infection of HT1080 cells, (ATCC CCL 121). On day 1, $5\times10^5$ HT1080 cells are plated on each well of a 6 well microtiter plate in 3.0 ml DMEM, 10% FBS and 4 μg/ml polybrene. On day 2, the supernatant from each clone is serially diluted 10 fold and used to infect the HT1080 cells in 1.0 ml aliquots. The media is replaced with fresh DMEM, 10% FBS media, and the cells are incubated with the vector overnight at 37° C., 10% $CO_2$. On day 3, selection of transduced cells is performed by replacing the media with fresh DMEM, 10% FBS media containing 800 μg/ml G418. Cells are incubated at 37° C., 10% $CO_2$ for 14 days at which time G418 resistant colonies are scored at each dilution to determine the viral titer of each clone as colony forming units/ml (cfu/ml).

Using these procedures it can be shown that the titers of the HBVcore, HBVe and HCV core-E1-E2 producer cell lines are:

| | |
|---|---|
| DAcore-10 | $1 \times 10^6$ cfu/ml |
| DAcore-6A3 | $4 \times 10^6$ cfu/ml |
| DAcore-2D6 | $2.5 \times 10^6$ cfu/ml |
| DAcore-3A4 | $3 \times 10^6$ cfu/ml |
| DAcore-4A5 | $1.6 \times 10^6$ cfu/ml |
| DAcore-4D3 | $0.7 \times 10^6$ cfu/ml |
| DAcore2A2 | $0.6 \times 10^6$ cfu/ml |
| HXcore-9D2 | $5 \times 10^6$ cfu/ml |
| HXcore-1E11 | $4 \times 10^6$ cfu/ml |
| HVcore-7F3 | $3 \times 10^6$ cfu/ml |
| HXcore-2B2 | $3 \times 10^6$ cfu/ml |
| DAHBe 4-7 | $3 \times 10^6$ cfu/ml |
| DAHBe-2A1 | $2.2 \times 10^6$ cfu/ml |
| DAHBe-4 | $1.2 \times 10^6$ cfu/ml |
| DAHBe-2A2 | $0.83 \times 10^6$ cfu/ml |
| DAHBe-1A4 | $1.02 \times 10^6$ cfu/ml |
| DAHBe-3B2 | $0.39 \times 10^6$ cfu/ml |
| DAHBe-5A2 | $2 \times 10^6$ cfu/ml |
| DAHBe-2B3 | $0.7 \times 10^6$ cfu/ml |
| DACE1E2-7C8 | $5.6 \times 10^6$ cfu/ml |
| DACe1E2-6E5 | $8.1 \times 10^6$ cfu/ml |

B. Titering of Multivalent Vectors i. Endpoint Dilution

Since the multivalent vectors do not contain a selectable marker, such as the neomycin gene, another way of titering the vector is described in more detail below. Briefly, 1.0 ml of vector supernatant is diluted five fold to a final dilution of $10^{-9}$ ml. One milliliter of each dilution is then used to transduce $5\times10^5$ HT1080 cells (ATCC No. CCL 121) essentially as noted in Example 7B. However, instead of adding G418, DNA is extracted from each dish 7 days later as described by Willis (*J. Biol. Chem.* 259:7842–7849, 1984). The HBV e/core is amplified by PCR using the following PCR primers obtained from Genset (Paris, France).

The PCR amplification for HBV e/core is performed with the sense primer that corresponds to the nucleotide sequence 1865 to 1889 of the adw clone.

(SEQUENCE ID. NO. 38)

5'-3': TTC AAG CCT CCA AGC TGT GCC TTG G

This primer corresponds to the anti-sense nucleotide sequence 2430 to 2409 of the adw clone.

(SEQUENCE ID. NO. 39)

5'-3': TCT GCG ACG CGG CGA TTG AGA

This is the probe sequence used to confirm the presence of the desired PCR product and corresponds to the nucleotide sequence 1926 to 1907 of the adw strain of hepatitis B virus.

(SEQUENCE ID. NO. 40)

5'-3': GGA AAG AAG TCA GAA GGC AA

The PCR amplification for hepatitis C core is performed with the sense primer that corresponds to the nucleotide sequence 328 to 342 of the HCV-J clone.

(SEQUENCE ID. NO. 41)

5'-3': CAT GAG CAC AAA TCC

This primer corresponds to the anti-sense nucleotide sequence 907 to 892 of the HCV-J clone.

(SEQUENCE ID. NO. 42)

5'-3': GGG ATG GTC AAA CAA G

This is the probe sequence used to confirm the presence of the desired 564 bp PCR product and corresponds to the nucleotide sequence 674 to 693 of the HCV-J clone.

(SEQUENCE ID. NO. 43)

5'-3': GTC GCG TAA TTT GGG TAA GG

The PCR amplification for hepatitis C NS3/NS4 is performed with the sense primer that corresponds to the nucleotide sequence 4876 to 4896 of the HCV-J clone.

(SEQUENCE ID. NO. 44)

5'-3': TCC TGT GTG AGT GCT ATG ACG

This primer corresponds to the anti-sense nucleotide sequence 6321 to 6302 of the HCV-J clone.

(SEQUENCE ID. NO. 45)

5'-3': GAA GTC ACT CAA CAC CGT GC

This is the probe sequence used to confirm the presence of the desired 1426 bp PCR product and corresponds to the nucleotide sequence 5618 to 5637 of the HCV-J clone.

(SEQUENCE ID. NO. 46)

5'-3': CAC ATG TGG AAC TTC ATC AG

The PCR products are analyzed by Southern blot analysis with the appropriate $^{32}$P-labeled probes (Sambrook et al., *Molecular Cloning, a Laboratory Manual*, 2nd ed., Cold Spring Harbor Laboratory, Cold Spring Harbor, N.Y., 1989). Signal is expected in all of the lower dilutions and gradually decrease at higher dilutions. The last dilution where a signal is visible yields the infectious U/ml of the vector.

ii. Titering Retrovectors by PCR

PCR may also be utilized to determine the titer of vectors that do not contain selectable markers. Briefly, 1.0 ml of vector supernatant is used to transduced $5\times10^5$ HT1080 cells in 6 well plates. The transduced cells are grown to confluency and the cells counted. The concentration of cells is adjusted to $5\times10^5$ cells/ml. The cells are centrifuged at 3000 rpm for 5 minutes at room temperature. The supernatant is discarded and cells lysed with 1 ml of RIPA buffer (10 mM Tris, pH 7.4, 1% NP40, 0.1% SDS, 150 mM NaCL). The cells are resuspended and transferred to an eppendorf tube. Cells are centrifuged for 10 seconds at maximum speed in a microfuge at room temperature. The supernatant is discarded and 10 µl proteinase K (10 mg/ml, Stratagene, La Jolla, Calif.) is added to the cells. This mixture is incubated for 60 minutes at 37° C. TE (10 mM Tris, pH 7.6, 1 mM EDTA) is added to the incubated cells to a final concentration of $1\times10^7$ nuclei/ml. This solution is boiled at 100° C. for 10 minutes.

A standard curve is created using a clone of HT1080 cells that contains one proviral copy of the vector. This positive control of DNA is mixed with the negative control DNA (HT1080) in the following positive:negative control ratios: 100:1, 3:1, 1:1, 1:3, and 1:100. Approximately 2.5 µl of sample DNA is placed in a reaction vessel. Approximately 30 µof $H_2O$, 5 µl 10×PCR buffer 4 µl $MgCl_2$ (25 mM each), 5 µl primer mix containing primer DNAs (aliquoted at 100 ng/µl), and 0.25 µl Amplitaq (Cetus, Los Angeles, Calif.) is added to each reaction vessel containing sample DNA. To this mixture is added 1.0 µl alpha $^{32}$P dCTP. The mixture is mixed and 47.5 µl is aliquoted for the PCR reaction. The PCR program is set at 94° C. for 2 minutes, followed by 26 cycles at 94° C. for 30 seconds, followed by a single cycle at 64° C. for 30 seconds, and a final cycle at 72° C. for 30 seconds. The PCR mixture is then cooled to 4° C.

Approximately 10 µl of the PCR mixture is mixed with 10 µl of gel loading buffer containing 25% glycerol, 75% TE and bromophenol blue and loaded onto a 1% agarose gel. Electrophoresis is performed in 1×TBE (0.045 M Trisborate, 0.001 M EDTA, pH 8.0) running buffer at 130 volts for 30 minutes. Following electrophoresis, the DNA is transferred onto Duralon-UV (Stratagene, San Diego, Calif.) as described (Sambrook et al. (eds.), Cold Spring Harbor Press, 1989). The Duralon-UV membrane is removed from the transfer apparatus, wrapped in Saran Wrap and signals are quantitated using Ambis phosphorimager (Ambis, San Diego, Calif.). The titer value of each sample is determined by comparison to a standard curve described above and presented as % of positive control.

Example 9

DETECTION OF REPLICATION COMPETENT RETROVIRUSES

The extended $S^+$ $L^-$ assay determines if replication competent, infectious virus is present in the supernatant of the cell line of interest. The assay is based on the empirical observation that infectious retroviruses generate foci on the indicator cell line $MiCl_1$ (ATCC CCL 64.1). The $MiCl_1$ cell line is derived from the Mv1Lu mink cell line (ATCC CCL 64) by transduction with Murine Sarcoma Virus (MSV). It is a non-producer, non-transformed, revertant clone containing a murine sarcoma provirus that forms sarcoma ($S^+$) indicating the presence of the MSV genome but does not cause leukemia ($L^-$) indicating the absence of replication competent virus. Infection of $MiCl_1$ cells with replication competent retrovirus "activates" the MSV genome to trigger "transformation" which results in foci formation.

Supernatant is removed from the cell line to be tested for presence of replication competent retrovirus and passed through a 0.45µ filter to remove any cells. On day 1 Mv1Lu cells are seeded at $1\times10^5$ cells per well (one well per sample to be tested) of a 6 well plate in 2 ml DMEM, 10% FBS and 8 µg/ml polybrene. Mv1Lu cells are plated in the same manner for positive and negative controls on separate 6 well plates. The cells are incubated overnight at 37° C., 10% $CO_2$. On day 2, 1.0 ml of test supernatant is added to the Mv1Lu cells. The negative control plates are incubated with 1.0 ml of media. The positive control consists of three dilutions (200 focus forming units, (ffu), 20 ffu and 2 ffu each in 1.0 ml media) of MA virus (Miller et al., *Molec. and Cell. Biol.* 5:431–437, 1985) which is added to the cells in the positive control wells. The cells are incubated overnight. On day 3 the media is aspirated and 3.0 ml of fresh DMEM and 10% FBS is added to the cells. The cells are allowed to grow to confluency and are split 1:10 on day 6 and day 10, amplifying any replication competent retrovirus. On day 13 the media on the Mv1Lu cells is aspirated and 2.0 ml DMEM and 10% FBS is added to the cells. In addition the $MiCl_1$ cells are seeded at $1\times10^5$ cells per well in 2.0 ml DMEM, 10% FBS and 8 µg/ml polybrene. On day 14 the supernatant from the Mv1Lu cells is transferred to the corresponding well of the $MiCl_1$ cells and incubated overnight at 37° C., 10% $CO_2$. On day 15, the media is aspirated and 3.0 ml of fresh DMEM and 10% FBS is added to the cells. On day 21 the cells are examined under the microscope at 10xpower for focus formation (appearing as clustered, refractile cells that overgrow the monolayer and remain attached) on the monolayer of cells. The test article is determined to be contaminated with replication competent retrovirus if foci appear on the $MiCl_1$ cells.

Using these procedures, it can be shown that the HBV core producer cell lines DA core-1, DA core-10, and HBVe producer cell line DA HBe 4–7, are not contaminated with replication competent retroviruses.

Another assay to detect whether replication competent infectious retrovirus is present in the cell line of interest is the *Mus dunni* cocultivation assay. This assay involves cocultering the producer cell clone with the *Mus dunni* cell line to amplify any low level replication competent retrovirus. Supernatants from these cocultivations may then be tested using the MdH marker rescue assays described in U.S. Ser. No. 08/366,788. Briefly, in a marker rescue assay, replication competent retrovirus infects a cell line containing a replication-defective marker provirus. Following infection, the replication competent retrovirus packages or "rescues" the marker provirus such that it can be detected after subsequent transduction and expression in a target cell line. Approximately one cell infected with replication competent virus can be detected by cocultivation with *Mus dunni* cells under these conditions.

Using this assay, it can be shown that the following producer cell lines are not contaminated with replication competent retroviruses.

| HBV core producer cell lines | HBVe producer cell lines |
|---|---|
| DAcore-2D6 | DAHBe-2A1 |
| DAcore-3A4 | DAHBe-4 |
| DAcore-4A5 | DAHBe-2A2 |
| DAcore-2A2 | DAHBe-1A4 |
| DAcore-6A3 | DAHBe-3B2 |
|  | DAHBe-5A2 |
|  | DAHBe-2B3 |

Example 10

GENERATION OF RECOMBINANT ADENOVIRAL VECTORS

One microgram of pAdM1-HBe linearized with Cla I is mixed with one microgram of Cla I-cut Ad5delta e1 delta E3 (Gluzman et al., in *Eucaryotic Viral Vectors*, pp. 187–192, Cold Spring Harbor, 1982) viral DNA. This DNA mixture is transfected onto $5-6 \times 10^5$ 293 cells (ATCC CRL 1573) in 60 mm diameter dishes using 7 ul of Lipofectamine (BRL, Gaithersburg, Md.) in 0.8 ml of Opti-MEM I Reduced Serum Medium (BRL, Gaithersburg, Md.). One milliliter of DMEM media with 20% FBS is added after 5 hours and DMEM media with 10% FBS is replenished the following day. After the appearance of c.p.e. (8–10 days), the culture is harvested and the viral lysates are subjected to two rounds of plaque purification. Individual viral plaques are picked and amplified by infecting 293 cells in 6 well plates (at a cell density of $1 \times 10^5$ cells per well). Recombinants are identified by southern analysis of viral DNA extracted from infected cells by the Hirt procedure (Hirt, 1967). After positive identification, the recombinant virus is subjected to two additional rounds of plaque purification. Titers are determined by plaque assay as described in Graham et al., *J. Gen. Virol.* 36:59–72, 1977. Viral stocks are prepared by infecting confluent 293 cells ($2 \times 10^6$ cells) in 60 mm diameter dishes at a multiplicity of 20 pfu/cell. All viral preparations are purified by CsCl density centrifugation (Graham and Van der Elb, *Virol.* 52:456–457, 1973), dialyzed, and stored in 10 mM Tris-HCl (pH 7.4), 1 mM $MgCl_2$ at 4° C. for inmmediate use, or stored with the addition of 10% glycerol at –70° C.

Example 11

INTRODUCTION OF VECTOR CONSTRUCT INTO CELLS

A. Recombinant Retroviral Vectors i. Transduction of Murine Cells

The murine fibroblast cell lines BC10ME (ATCC No. TIB85) B16 and L-M(TK⁻) (ATCC No. CCL 1.3) are grown in DMEM containing 4500 mg/L glucose, 584 mg/L L-glutamine (Irvine Scientific, Santa Ana, Calif.) and 10% FBS (Gemini, Calabasas, Calif.).

The BC10ME, B16, and L-M(TK⁻) fibroblast cell lines are plated at $1 \times 10^5$ cells each in a 10 cm dish in DMEM, 10% FBS and 4 µg/ml polybrene. Each is transduced with 1.0 ml of the retroviral vector having a vector titer of approximately $10^5$ cfu/ml. Clones are selected in DMEM, 10% FBS and 800 µg/ml G418 as described in Example 7B.

The EL4 (ATCC No. TIB 39) cells and EL4/A2/$K^b$ cells (L. Sherman, Scripps Institute, San Diego, Calif.) are transduced by co-culture with the DA producer cells. Specifically, $1.0 \times 10^6$ EL4 cells or $1.0 \times 10^6$ EL4/A2/$K^b$ are added to $1 \times 10^6$ irradiated (10,000 rads) DA (vector titer of approximately $10^5$–$10^6$) producer cells in RPMI 1640 (Irvine Scientific, Santa Ana, Calif.), 10% FBS, and 4 µg/ml polybrene (Sigma, St. Louis, Mo.) on day 1. On day 2, $1.0 \times 10^6$ irradiated (10,000 rad) DA producer cells are added to the co-culture. On day 5 selection of the transduced EL4 or EL4/A2/KB cells is initiated with 800 µg/ml G418. The pool is dilution cloned as described in Example 7A.

BC10ME, B16, L-M(TK⁻), EL-4 cells transduced by multivalent vectors are not selected in G418; they are cloned by limiting dilution as in Example 7A and assayed for expression as described in Exanple 12A.

ii. Transduction of Macaque Cells

Peripheral blood mononuclear cells (PBMC) are spun through a Ficoll-hypaque column at 2000 rpm for 30 minutes at room temperature. Lymphoblastoid cell lines (LCL) are established for each macaque by infecting (transforming) their B cells with Herpes papio virus at a 1:1000 dilution of cell supernatant (594-S, Southwest Institute for Biomedical Research).

Three to five weeks after Herpes papio transformation, the actively growing cells are transduced twice with retrovital vector expressing HBV core or e antigen. Transduction of LCL is accomplished by co-culturing $1 \times 10^6$ LCL cells with $1 \times 10^6$ irradiated (10,000 rads) DA/HBe or DA/HB core producer cells in a 6 cm plate containing 4.0 ml of medium and 4.0 ug/ml polybrene. The culture medium consists of RPMI 1640, 20% heat inactivated fetal bovine serum (Hyclone, Logan, Utah), 5.0 mM sodium pyruvate, 5.0 mM non-essential amino acids and 2 mM L-glutamine. After overnight culture at 37° C. and 5% $CO_2$, the LCL suspension cells are removed and cocultured with $1 \times 10^6$ irradiated (10,000 rads) DA/HBe or DA/HB core producer cells as in the first transduction. Transduced LCL cells are selected by adding 800 ugm/ml G418 and cloned by limiting dilution.

iii. Transduction of Chimpanzee and Human Cells

Lymphoblastoid cell lines (LCL) are established for each patient by infecting (transforming) their B-cells with fresh Epstein-Barr virus (EBV) taken from the supernatant of a 3-week-old culture of B95-8, EBV transformed marmoset leukocytes (ATCC CRL 1612). Three weeks after EBV-transformation, the LCL are transduced with retroviral vector expressing HBV core or e antigen. Transduction of LCL is accomplished by co-culturing $1.0 \times 10^6$ LCL cells with $1.0 \times 10^6$ irradiated (10,000 rads) HX producer cells in a 6 cm plate containing 4.0 ml of medium and 4.0 µg/ml polybrene. The culture medium consists of RPMI 1640, 20% heat inactivated fetal bovine serum (Hyclone, Logan, Utah), 5.0 mM sodium pyruvate and 5.0 mM non-essential amino acids. After overnight co-culture at 37° C. and 5% $CO_2$, the LCL suspension cells are removed and 1×10$^6$ cells are again co-cultured for another 6–18 hours in a fresh plate containing 1.0×10$^6$ irradiated (10,000 rads) HX producer cells. Transduced LCL cells are selected by adding 800 µg/ml G418 and cloned to obtain high expression clones. The Jurkat A2/K$^b$ cells (L. Sherman, Scripps Institute, San Diego, Calif.) are transduced essentially as described for the transduction of LCL cells. LCLs transduced by multivalent vectors, Jurkat A$_2$/K$^b$ and EL4 A2/K$^b$ cells, are not selected in G418; they are cloned by limiting dilution as in Example 7A and assayed for expression as in Example 12A.

B. Transfection with Hepatitis B Virus Core CMV Expression Vector

L-M(TK$^-$) cells are seeded at 5×10$^5$ cells on a 10 cm tissue culture dish on day 1 with Dulbecco's Modified Eagle Medium (DMEM) and 10% fetal bovine serum (FBS). On day 2, the media is replaced with 5.0 ml fresh media 4 hours prior to transfection. A standard calcium phosphate-DNA coprecipitation is performed by mixing 60 µl 2.0 M $CaCl_2$, 10 µg CMV-HBc plasmid, and deionized water to a volume of 400 µl. Four hundred microliters of the DNA-$CaCl_2$ solution is added dropwise with constant agitation to 400 µl 2×precipitation buffer (50 mM HEPES-NaOH, pH 7.1, 0.25 M NaCl and 1.5 mM $Na_2HPO_4$—$NaH_2PO_4$). This mixture is incubated at room temperature for 10 minutes. The resultant fine precipitate is added to a culture dish of L-M(TK$^-$) cells plated the previous day. The cells are incubated with the DNA precipitate overnight at 37° C. On day 3 the medium is removed and fresh medium is added. On day 4, cell extracts are harvested and assayed for expression as in Example 12A.

C. Infection with Recombinant Adenoviral Vector

Subconfluent monolayers of L-M(TK$^-$) cells (approximately 10$^6$ cells) growing in 35 mm (diameter) dishes are infected with recombinant HBe adenovirus vectors at a multiplicity of 100 pfu/cell. One hour after adsorption at 37° C., the virus inocula is removed and DMEM supplemented with 2% FBS is added. Thirty to forty hours after infection when pronounced c.p.e. is observed, cell extracts are harvested and assayed for expression as in Example 12A.

Example 12

EXPRESSION OF TRANSDUCED GENES

A. Elisa i. HBV Core Antigen and HBVe Antigen

Cell lysates from cells transduced by KT-HBe-c or KT-HBc are made by washing 1.0×10$^7$ cultured cells with PBS, resuspending the cells to a total volume of 600 µl on PBS, and sonicating for two 5-second periods at a setting of 30 in a Branson sonicator, Model 350, (Fisher, Pittsburgh, Pa.) or by freeze thawing three times. Lysates are clarified by centrifugation at 10,000 rpm for 5 minutes.

Core antigen and precore antigen in cell lysates and secreted e antigen in culture supernatant are assayed using the Abbott HBe, rDNA EIA kit (Abbott Laboratories Diagnostic Division, Chicago, Ill.). Another sensitive EIA assay for precore antigen in cell lysates and secreted e antigen in culture supernatant is performed using the Incstar ETI-EB kit, (Incstar Corporation, Stillwater, Minn.). A standard curve is generated from dilutions of recombinant hepatitis B core and e antigen obtained from Biogen (Geneva, Switzerland).

Using these procedures approximately 20–40 ng/ml HBV e antigen is expressed in transduced cell lines, and 38–750 ng/ml of HBV core antigen is expressed in transduced cell lines (FIG. 5).

ii. HCV E2/NS1

The ELISA assay to measure expression levels of $E2_{715}$ in retrovirally transduced cells was conducted essentially as described by Spaete, R. R. et al., in *Virology* 188:819–830, 1992. Briefly, microtiter plates (Immulon 2, Dynatech Laboratories, Inc., Chantilly, Va.) coated with affinity-purified goat antibodies to E2/NS1 expressed in yeast were incubated one hour at 37° C. with the lysates of retrovirally transduced cells. Washed wells were then incubated for one hour at 37° C. with a monoclonal antibody against yeast-derived E2/NS1, followed by incubation for 1 hour at 37° C. with a goat anti-mouse Ig conjugated with alkaline phosphatase (Boehringer-Mannheim). After aspiration of the unbound material and washing of the wells, the reaction was developed by the addition of p-nitrophenylphosphate. The E2/NS1 protein which was used as a quantitation standard for the ELISA was prepared from conditioned media of *Spodoptera frugiperda* insect cells infected with a recombinant baculovirus expressing E2/NS1.

B. Expression of Transduced Genes by Western Blot Analysis

Proteins are separated according to their molecular weight (MW) by means of SDS polyacrylarnde gel electrophoresis. Proteins are then transferred from the gel to a IPVH Immobilon-P membrane (Millipore Corp., Bedford, Mass.). The Hoefer HSI TTE transfer apparatus (Hoefer Scientific Instruments, Calif.) is used to transfer proteins from the gel to the membrane. The membrane is then probed with polyclonal antibodies from patient serum that reacts specifically with the expressed protein. The bound antibody is detected using $^{125}$I-labeled protein A, which allows visualization of the transduced protein by autoradiography.

Alternatively, proteins may be separated by SDS polyacrylamide gel electrophoresis, followed by transfer from the set to a nylon membrane (Immobilon-P, Millipore Corp.). The membrane is then probed with a primary rabbit antibody of either anti-HB core specificity, or anti-neo$^r$ specificity, followed by a secondary antibody, horseradish peroxidase-conjugated goat anti-rabbit IgG. Antibody bound protein was then visualized on the membrane utilizing the ECL detection kit (Amersham Cat. No. RPN 2108), essentially according to the manufacturers instructions.

Figure 15A:
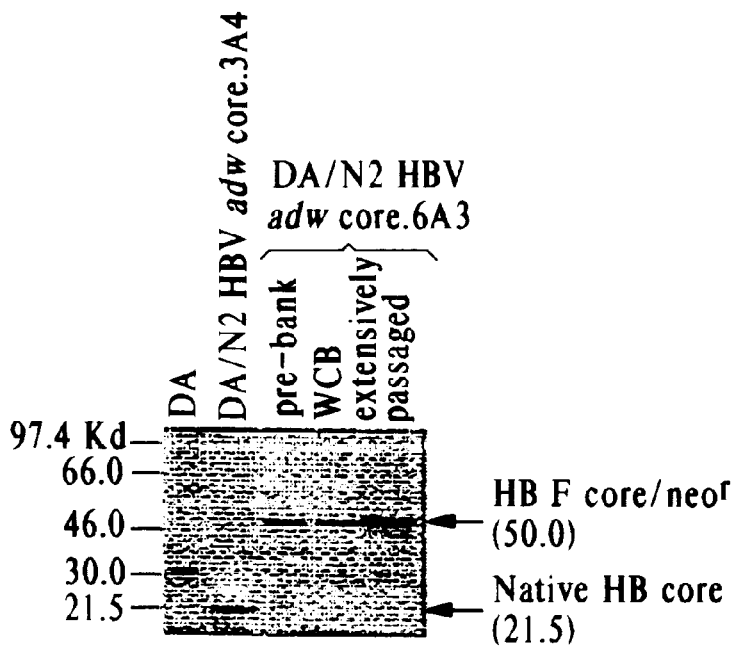
FIGS. 15A and B are a pair of Western blots showing the expression of the 50.0 kd fusion HBcore/neo protein in DAcore 6A3.
Figure 15B:
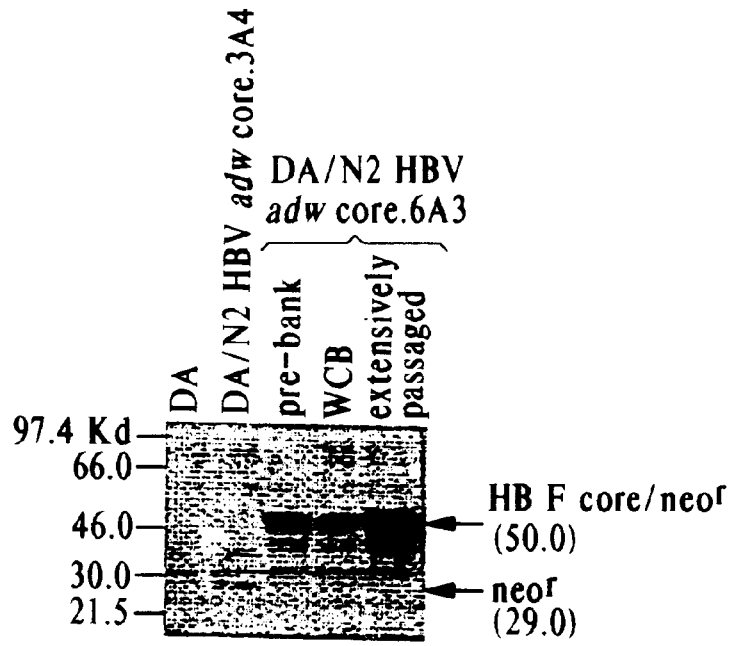

Results of such experiments are shown in FIGS. 15A and B, and 16A and B. Briefly, FIGS. 15A and 15B show the expression of HB F core/neo$^r$ in DA/N2 HBV adw core. 6A3. Cell lysates were obtained from pre-bank, working cell bank (WCB) and extensively passaged samples. Lane 1 is non-transduced DA. Lane 2, DA/N2 HBV adw core. 3A4, is DA transduced with vector encoding both the native form of HB core, 21.5 Kd (A), and neo$^r$ driven by the SV40 promoter, 29.0 Kd (B). Lanes 3–5 are prebank, WCB and extensively passaged samples of DA/N2 HBV adw core. 6A3 producing vector encoding the HB F core/neo$^r$ fusion protein, 50.0 Kd (A, B).

Figure 16A:
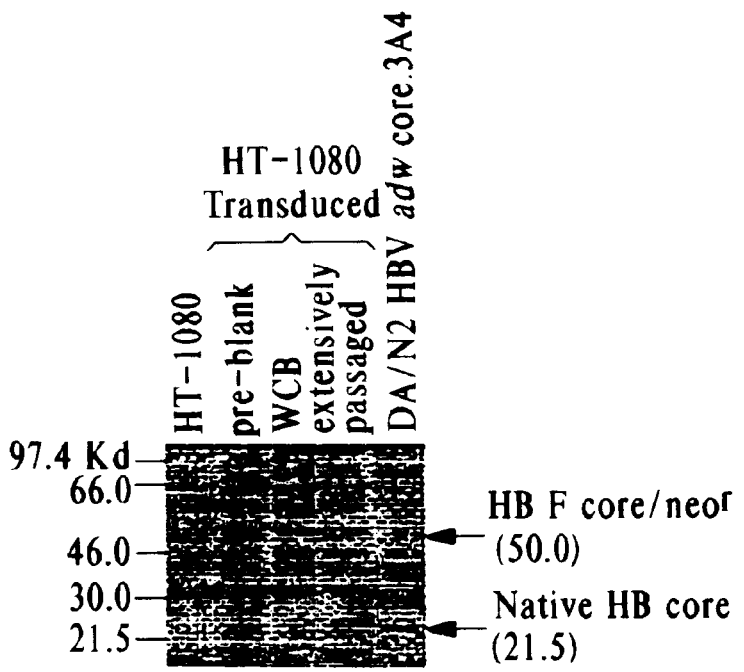
FIGS. 16A and B are a pair of Western blots showing the expression of the 50.0 kd fusion HBcore/neo protein in HT-1080 cells transduced by the retrovector from DAcore 6A3.
Figure 16B:
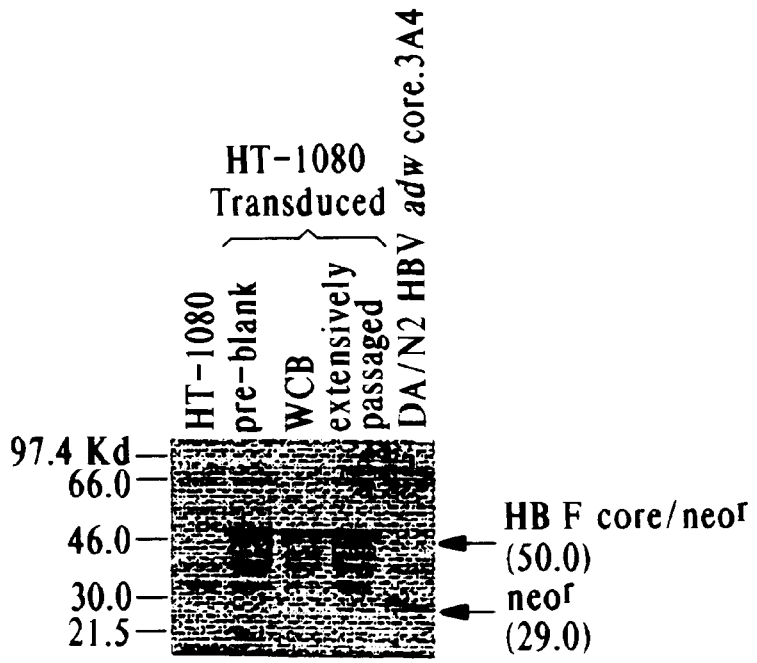

FIGS. 16A and 16B show the expression of HB F core/neo$^r$ in HBV-IT(V) transduced human cells using vector from DA/N2 HBV adw core. 6A3. Cell lysates were obtained from HT-1080 cells transduced with vector from DA/N2 HBV adw core. 6A3 cultures derived from prebank, WCB and extensively passaged samples. Lane 1 is non-transduced HT-1080. Lanes 2–4 are HT-1080 transduced with vector encoding HB F core/neo$^r$ fusion protein, 50.0 Kd from prebank, WCB and extensively passaged samples of DA/N2 HBV adw core. 6A3 (A, B). Lane 5 is DA/N2 HBV adw core. 3A4 cell lysates, described above, expressing both native HB core protein, 21.5 Kd (A) and neo$^r$, 29.0 Kd (B).

C. Immunoprecipitation/Western Blot

Characterization of the precore/core and e antigens expressed by transduced cells is performed by immunoprecipitation followed by Western blot analysis. Specifically, 0.5–1.0 ml of cell lysate in PBS or culture supernatant is mixed with polyclonal rabbit anti-hepatitis B core antigen (DAKO Corporation, Carpinteria, Calif.) bound to G-Sepharose (Pharmacia LKB, Uppsala, Sweden) and incubated overnight at 4° C. Samples are washed twice in 20 mM Tris-HCl, pH 8.0, 100 mM NaCl, 10 mM EDTA and boiled in sample loading buffer with 0.5% beta 2-mercaptoethanol. Proteins are first resolved by SDS polyacrylamide gel electrophoresis, and then transferred to Immobilon (Millipore Corp., Bedford, Me.) and probed with the DAKO polyclonal rabbit anti-hepatitis core antigen, followed by $^{125}$I-protein A.

Figure 6:
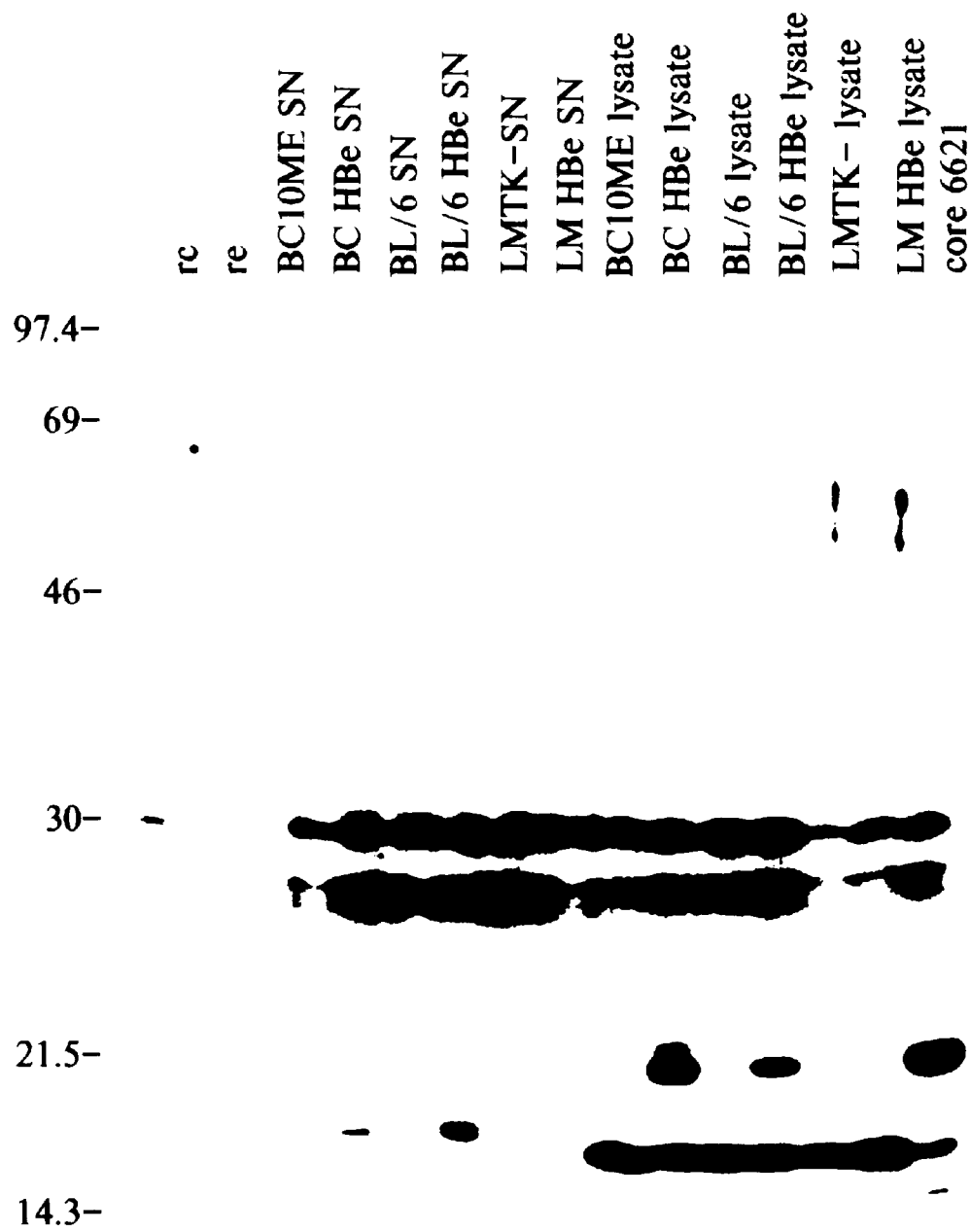
FIG. 6 is a Western blot showing immunoprecipitation/expression of secreted p17 kD HBV e protein and p23 kD pre-core intermediate protein by retrovirally transduced BC10ME and B1/6 cells. This blot also shows expression of p21 HBV core protein in cell lysates from retrovirally transduced BC10ME cells.

Using these procedures, it can be shown from FIG. 6 that the 17 Kd HB e protein is secreted by transduced mouse cells into the culture supernatant and the p22, p23 intermediate hepatitis B e products are present mainly in the lysates of transduced mouse cells. This figure also shows expression of p21 HBV core protein in cell lysates from retrovirally transduced BC10ME cells.

Example 13

TUMORIGENICITY AND TRANSFORMATION

A. Tumorigenicity Assay

Tumor formation in nude mice is a particularly sensitive method for determining tumorigenicity. Nude mice do not possess mature T-cells, and therefore lack a functional cellular immune system, providing a useful in vivo model in which to test the tumorigenic potential of cells. Normal non-tumorigenic cells do not display uncontrolled growth properties if injected into nude mice. However, tumorigenic cells will proliferate and generate tumors in nude mice. Briefly, the vector construct is administered by intramuscular and intraperitoneal injection into nude mice. The mice are visually examined for a period of 4 to 16 weeks after injection in order to determine tumor growth. The mice may also be sacrificed and autopsied in order to determine whether tumors are present (Giovanella et al., *J. Natl. Cancer Inst.* 48:1531–1533, 1972; Furesz et al., "Tumorigenicity testing of cell lines considered for production of biological drugs," *Abnormal Cells*, New Products and Risk, Hopps and Petricciani (eds), Tissue Culture Association, 1985; Levenbook et al., *J. Biol. Std.* 13:135–141, 1985). This test is performed by Quality Biotech Inc., (Camden, N.J.).

B. Transformation Assay

Tumorigenicity has shown to be closely correlated with the property of transformation. One assay which may be utilized to determine transformation is colony formation of cells plated in soft agar (MacPherson et al., *Vir.* 23:291–294, 1964). Briefly, one property of normal non-transformed cells is anchorage dependent growth. Normal non-transformed cells will stop proliferating when they are in semi-solid agar support medium, whereas transformed cells will continue to proliferate and form colonies in soft agar.

HT1080 (ATCC CCL 121), a neoplastic cell line derived from human fibrosarcoma and known to cause tumors in 100% of nude mice, is used as the assay positive control. WI-38 (ATCC CCL 75), a diploid embryonic human lung cell line which is not tumorigenic in nude mice, is used as the assay negative control.

WI-38 cell lines are transduced with the vector construct as described in Example 11Ai. Duplicate samples of each of the transduced cell lines, HT1080, and WI-38, are cultured in agar. Briefly, a lower layer of 5.0 ml 0.8% Bactoagar (Difco, Detroit, Mich.) in DMEM 17% FBS is set on 60 mm tissue culture plates. This is overlaid with 2.0 ml 0.3% Bactoagar in the same medium with the cells suspended at a concentration of $5 \times 10^5$ cells/ml. To reduce background clumps, each cell line is strained through a 70 ml nylon mesh before suspending in the agar solution. The plates are incubated at 37° C. in a humidified atmosphere of 5% $CO_2$ for 14 days. Within 24 hours of plating, representative plates of each cell line are examined for cell clumps present at the time of plating. On day 13, the plates are stained with 1.0 ml INT vital stain (Sigma, St. Louis, Mo.) and on day 14, they are scanned for colonies of 150 ml in diameter using a 1 mm eyepiece reticle.

Only colonies spanning 150 $\mu$m or larger in any orientation are scored, because colonies of this size can be readily observed in all planes under the microscope and non-transformed cells rarely form colonies of this size. At the end of the assay, the plating efficiencies for each cell line are calculated as b/a x 100, where b equals the sum of colonies on all plates, and a equals the total number of cells plates. A non-transformed cell line is one which has a plating efficiency of lower than or equal to 0.001%. Therefore, a transformed cell line will have a plating efficiency of greater than 0.001% (Risser et al., *Virol.* 59:477–489, 1974).

Example 14

ADMINISTRATION PROTOCOLS

A. Mice i. Administration of Recombinant Protein

A monomeric, non-particulate form of Hepatitis B virus core protein (D. Milich, Scripps Institute, San Diego, Calif.) might be useful for priming T-help for CTL. Six- to eight-week old female C3H/He CR, HLA A2.1, HLA A2.1/$K^b$ mice are primed with 10 $\mu$g of monomeric HBV core emulsified in complete Freund's adjuvant. Two to three weeks later, the mice are injected with either formulated HBV e or HBV core retroviral vector (Example 14A iv a).

ii. Administration of Recombinant Protein with Adjuvax

BALB/c, C57BL/6 amd C3H/He mice are injected with a suspension of recombinant HBV e or recombinant HBV core/Adjuvax. The antigen-Adjuvax suspension is prepared by adding 1.0 ml of antigen solution in PBS per mg of dry Adjuvax powder (Alpha-Beta Technology, Inc., Worchester, Mass.). The antigenAdjuvax mixture is hydrated by drawing it into a syringe with an 18 gauge needle and making multiple (8–10) passages of the suspension through the needle and syringe. Mice are injected two or more times with 0.2 ml of the antigen-Adjuvax preparation. The injections are given intraperitoneally or intramuscularly one to two weeks apart. One to two weeks after the last injection, mice are bled and serum is tested for antibody specific for HBV e antigen and HBV core antigen. At the same time, spleens are removed and splenocytes are restimulated in vitro with irradiated (10,000 rads) syngeneic cells expressing HBV e or HBV core antigen. Effectors are tested for HBV e/core-specific CTL activity in a standard $^{51}$Cr release assay (see Example 15A i).

iii. Administration of Retroviral-Transduced Cells

Six- to eight-week old female BALB/c, C57BL/6, C3H/He mice (Charles River Laboratories, Charles River, Ma.) are injected intraperitoneally (i.p.) with $1 \times 10^7$ irradiated (10,000 rads at room temperature) syngeneic cells expressing the antigen. Four injections are given at one week intervals. After each injection sera is removed by retro-orbital bleeds for detection of antibody induction as described in Example 15B. Seven days after the last injection, animals are sacrificed, and the splenocytes removed for the chromium release CTL assays as described in Example 15Ai.

iv. Administration of Vector Construct a. Recombinant Retroviral Vector

Six- to eight-week-old female BALB/c, C57BL/6, C3H/He (Charles River Laboratories, Charles River, Ma.), HLA A2.1 (V. Engelhard, Charlottesville, Va.) or HLA $A_{2.1}/K^b$ (L. Sherman, Scripps Institute, San Diego, Calif.) mice are injected intramuscularly (i.m.) at two sites, or intradermally at the base of the tail with 0.1 ml of formulated HBV core, HBV e, or HB Fcore/neo$^R$ retroviral vector. Two, four, or six injections are given at one week intervals. After each injection, sera is removed by retro-orbital bleeds for detection of antibody induction as described in Example 15B. Fourteen days after the last injection, the animals are sacrificed. Chromium release CTL assays are then performed essentially as described in Example 15Ai.

b. Recombinant Retroviral Vector with Cytokine

Six- to eight-week-old female C3H/HE Charles River, HLA A2.1 or HLA A2.1/Kb are also injected intramuscularly with 0.05 ml of formulated HBV core retroviral vector and 0.05 ml of 25,000 units of either murine γ-interferon (m γ-IFN), or murine IL-2. Two to three injections are given at one week intervals. Fourteen days after the last injection, the animals are sacrificed. Chromium release CTL assays are then performed essentially as described in Example 15Ai c. Direct DNA Administration Female C3H, HLA A2.1, or HLA A2.1/K$^b$ mice at 5–6 weeks of age are injected into the tibialis anterior muscle of both legs. Each leg receives 50 ul of sterile 0.9% sterile phosphate-buffered saline (PBS) pH 7.3 containing 100 ugm of DNA with a 27-gauge needle and a TB syringe. Three injections are given at 3-week intervals. Animals are sacrificed and spleens harvested 4 weeks after the last injection.

d. Recombinant Adenoviral Vectors

Six to eight week old female C3H/He, HLA A2.1 or HL A2.1/K$^b$ mice are injected intravenously or intraperitoneally with $5\times10^7$ pfu of recombinant HBe adenovirus. Seven days after the injection, the animals are sacrificed for chromium release CTL assays as described in Example 15Ai.

B. Macaque

Male and female macaques of variable age (Primate Research Institute, White Sands, N. Mex.) are injected intramuscularly (4 sites), or intradermally in the nape of the neck with 0.5 ml of formulated HB Fcore/neo$^R$ vector, HBV core or HBV e retroviral vector. Four injections are given at 14 day intervals. Fourteen days after each injection, blood samples are collected for chromium release CTL assays as described in Example 15Aiii.

C. Chimpanzee

1. Hepatitis B Therapy

The data generated in the mouse and macaque systems is used to determine the protocol of administration of vector in chimpanzees chronically infected with hepatitis B virus. Based on the induction of HBV-specific CTLs in mice and macaques, the subjects in chimpanzee trials (White Sands Research Center, Alamorgordo, N. Mex., Southwest Foundation for Biomedical Research, San Antonio, Tex.) will receive four doses of formulated HB Fcore/neo$^R$ vector at 14 day intervals. The dosage is $10^9$ cfu/ml of formulated HB Fcore/neo$^R$ vector given in four 0.5 ml injections i.m. on each injection day. Blood samples are drawn during treatment in order to measure serum alanine aminotransferase (ALT) levels, the presence of antibodies directed against the hepatitis B e antigen, HBV DNA levels and to assess safety and tolerability of the treatment. The hepatitis B e antigen and antibodies to HB e antigen are detected by Abbott HB e rDNA EIA kit as described in Example 12A. Efficacy of the induction of CTLs against hepatitis B core or e antigen is determined as in Example 15Aiv.

Based on the safety and efficacy results from the chimpanzee studies, the dosage and inoculation schedule is determined for administration of the vector to subjects in human trials. These subjects are monitored for serum ALT levels, presence of hepatitis B e antigen, the presence of antibodies directed against the hepatitis B e antigen, and HBV DNA levels, essentially as described above. Induction of human CTLs against hepatitis B core or e antigen is determined as in Example 15A iv.

2. Hepatitis C Therapy

Similar to the above-discussed hepatitis B therapy, chimpanzees chronically infected with hepatitis C virus receive four doses of formulated HCVCE1E2 vector at 14 day intervals. A dosage of $10^9$ cfu/ml of formulated HCVCE1E2 vectors given in four 0.5 ml injections i.m. on each injection day. Blood samples are drawn during treatment in order to measure serum alanine aminotransferase (ALT) levels, circulating HCV antibodies (Kuo et al., Science 244:362–364, 1989), HCV RNA levels (Gretch et al., J. Clin. Microbiol. 31, 289–291), liver biopsies and peripheral blood lymphocytes using PCR and to assess safety and tolerability of the treatment. Efficacy of the induction of CTLs against hepatitis C core antigen is determined as in Example 15Aiv.

Based on the safety and efficacy results from the chimpanzee studies, the dosage and inoculation schedule is determined for administration of the vector to subjects in human trials these subjects are monitored for serum ALT levels, presence of HCV RNA essentially as described above. Induction of human CTLs against hepatitis C core antigen is determined as in Example 15Aiv Example 15

A. Cytotoxicity Assays i. Inbred Mice

Animals are sacrificed after administration of vector or transduced syngeneic cells. Splenocytes ($3\times10^6$/ml) are harvested and cultured in vitro with their respective irradiated transduced cells ($6\times10^4$/ml) in T-25 flasks (Corning, Corning, N.Y.). Culture medium consists of RPMI 1640, 5% heat-inactivated fetal bovine serum, 1 mM sodium pyruvate, 50 µg/ml gentamycin and $10^{-5}$M b 2-mercaptoethanol (Sigma, St. Louis, Mo.). Effector cells are harvested 4–7 days later and tested using various effector:target cell ratios in 96 well microtiter plates (Corning, Corning, N.Y.) in a standard chromium release assay. Targets are the HB core or HBC transduced L-M(TK$^-$) cells whereas the non-transduced L-M(TK$^-$) cell lines are used as a control for background lysis. Specifically, $Na_2^{51}CrO_4$-labeled (Amersham, Arlington Heights, Ill.)(100 uCi, 1 hr at 37° C.) target cells ($1\times10^4$ cells/well) are mixed with effector cells at various effector to target cell ratios in a final volume of 200 µl. Following incubation, 100 µl of culture medium is removed and analyzed in a Beckman gamma spectrometer (Beckman, Dallas, Tex.). Spontaneous release (SR) is determined as CPM from targets plus medium and maximum release (MR) is determined as CPM from targets plus 1M HCl. Percent target cell lysis is calculated as: [(Effector cell+target CPM)−(SR)/(MR)−(SR)]×100. Spontaneous release values of targets are typically 10%–20% of the MR.

For certain CTL assays, the effectors may be in vitro stimulated multiple times, such as, for example, on day 8–12 after the primary in vitro stimulation. More specifically, $10^7$ effector cells are mixed with $6\times10^5$ irradiated (10,000 rads) stimulator cells, and $2\times10^7$ irradiated (3,000 rads) "filler" cells (prepared as described below) in 10 ml of "complete" RPMI medium. (RPMI containing: 5% heat inactivated Fetal Bovine Serum. 2 mM L-glutamine, 1 mM Sodium Pyruvate, 1×Non Essential Amino Acids, and $5\times10^5$ M β-mercaptoethanol). "Filler" cells are prepared from naive syngeneic mouse spleen cells resuspended in RPMI, irradiated with 3,000 rads at room temperature. Splenocytes are washed with RPMI, centrifuged at 3,000 rpm for 5 minutes at room temperature, and the pellet is resuspended in RPMI. The resuspended cells are treated with 1.0 ml Tris-Ammonium Chloride (100 ml of 0.17 M Tris Base, pH 7.65, plus 900 ml of 0.155 M NH$_4$Cl; final solution is adjusted to a pH of 7.2) at 37° C. for 3–5 minutes. The secondary in vitro restimulation is then cultured for 5–7 days before testing in a CTL assay. Any subsequent restimulations are cultured as described above with the addition of 2–10 U of recombinant human IL-2 (200 U/ml, catalog #799068, Boehringer Mannheim, W. Germany).

In certain cases, it may be necessary to add unlabeled non-transduced or β-gal/neo-transduced targets to labeled targets at a predetermined ratio. This reduces the background lysis of negative control cells.

The β-gal/neo-transduced targets are generated as follows. The plasmid pSP65 containing the bacterial β-gal gene is obtained, and the 3.1 Kb β-gal gene isolated as a Xba I-Sma I fragment and inserted into pC15 CAT (Anya et al., *Science* 229:69–73, 1985) digested with Xba I-Sma I. The β-gal gene is resected as a 3.1 Kb Sal I-Sma I fragment and inserted into the N2 IIIB gag/prot retroviral vector backbone at the Xho I and the blunted Cla I-site. This plasmid is designated CB-β gal.

The construction of $N_2$ III B gag/prot is described below. The major splice donor (SD) site of HIV-1 gag gene is removed by changing GT to AC by PCR of pSLCATdelBgl II (a vector that expresses gag/pol, tat, and rev, derived from a clone of HIV-1 IIIB called HXB2). During the PCR mutagenesis procedure, a Sac I site is also created upstream of the SD delta site so that a 780 bp Sac I-Spe I SD delta gag fragment could be purified. The 1.5 Kb Spe I-Eco RV gag-prot-RT fragment and the 780 bp Sac I-Spe I SD delta gag fragment are inserted into pUC18 Sac I-Sma I site. The resulting 2.3 Kb Sac I-blunt-Bam HI SD delta gag-prot-RT fragment is isolated from this pUC18 vector. A $SK^+$ gag-prot-RT expression vector is produced by a three-part ligation in which the 239 bp Xho I-Ssp I 5' rev DNA fragment and the 2.3 Kb Sac I-blunt-Bam HI SD delta gag-prot-RT fragment are inserted into the Xho I-Byl II 4.2 Kb rre/3' rev in $SK^+$ vector fragment. The resulting construct is designated $SK^+$ gag-prot-RT/rre/rev. An N2-based gag-prot-RT expression vector is produced by a two-part ligation in which the 3.8 Kb Xho I-Cla I gag-prot-RT/rre/rev fragment, from $SK^+$ gag-prot-RT-rre/rev, is inserted into the Xho I-Cla I site of fragment of N2 IIIB env, which contains the LTR's. N2 IIIB env is a derivative of $pAF/Env^r/SV_2neo$ with a modified 5' end based on the N2 recombinant retrovirus (Arnentano et al., *J. Virol.* 61:1647–1650, 1987; Eglitas et al., *Science* 230:1395–1398, 1985).

A Cla I-Cla I dominant selectable marker gene fragment from pAFVXM retroviral vector (Kriegler et al., *Cell* 38:483, 1984; St. Louis et al., *PNAS (USA)* 85:3150–3154, 1988) composed of a SV40 early promoter driving expression of the neomycin phosphotransferase gene, is cloned into plasmid $SK^+$. From this, a 1.3 Kb Cla I-Bst BI neo gene fragment is inserted into the N2-based gag/prot/RT expression vector at the Cla I site to facilitate isolation of infected and transfected cell lines. This vector was called N2 IIIB gag/prot.

Infectious retroviral particles are produced through the generation of a stable producer cell line by transfection of CB-β gal plasmid as described in Example 7A. The stable producer cell line utilized in these studies is derived from the DA cell line (WO 92/05266), and is designated DA-b gal. DA-b gal is then used to generate retroviral vector expressing b gal/neo. The C3H (H-2k) cell line LMTK- is transduced with b gal/neo vector as described in Example 11Ai. Clones are screened for b gal expression and the highest expressing line is chosen for use as a negative "neo" control in CTL assays.

Figure 9:
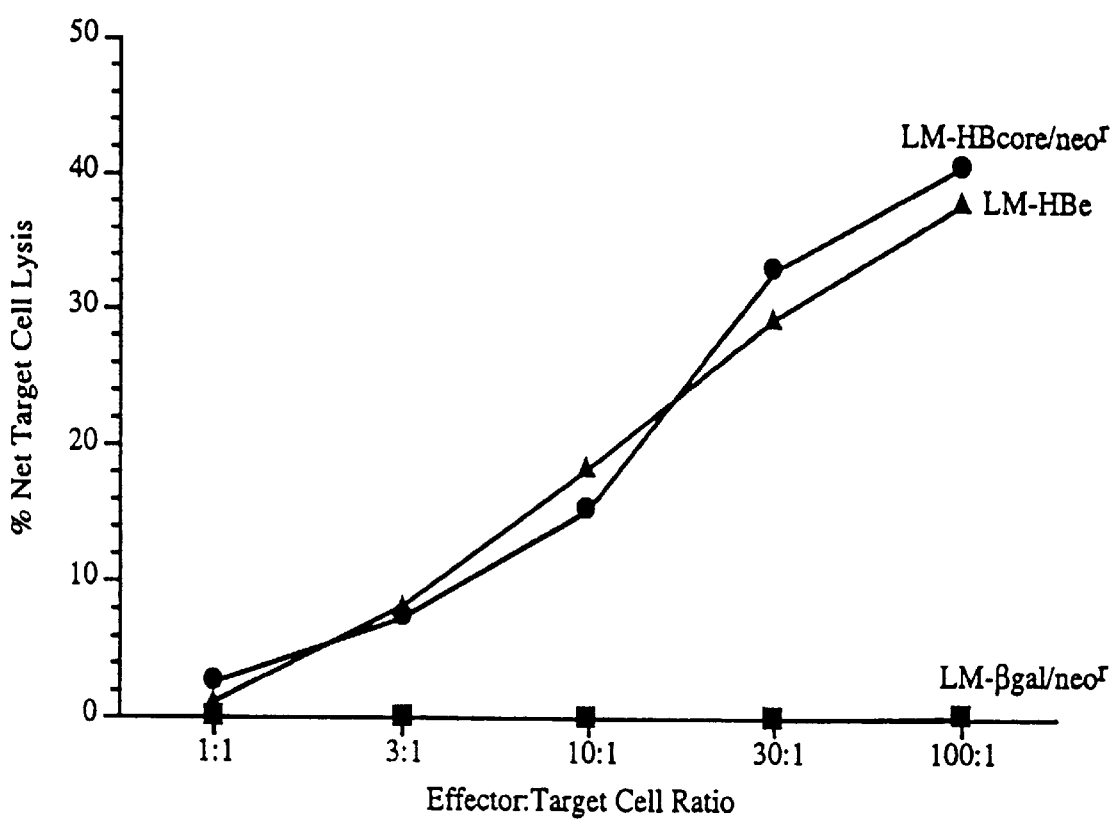
FIG. 9 is a graph showing induction of CTL responses against HBV core antigen and HBV e antigen in the C3H/He mice after i.m. administration of HBV core formulated HB Fcore/neo$^R$ vector.

Using these procedures, it can be shown that i.m. administration of HBV core formulated vector induces CTL responses against HBV core and HBV e antigen in C3H/He CR mice (see FIG. 9).

Figure 10:
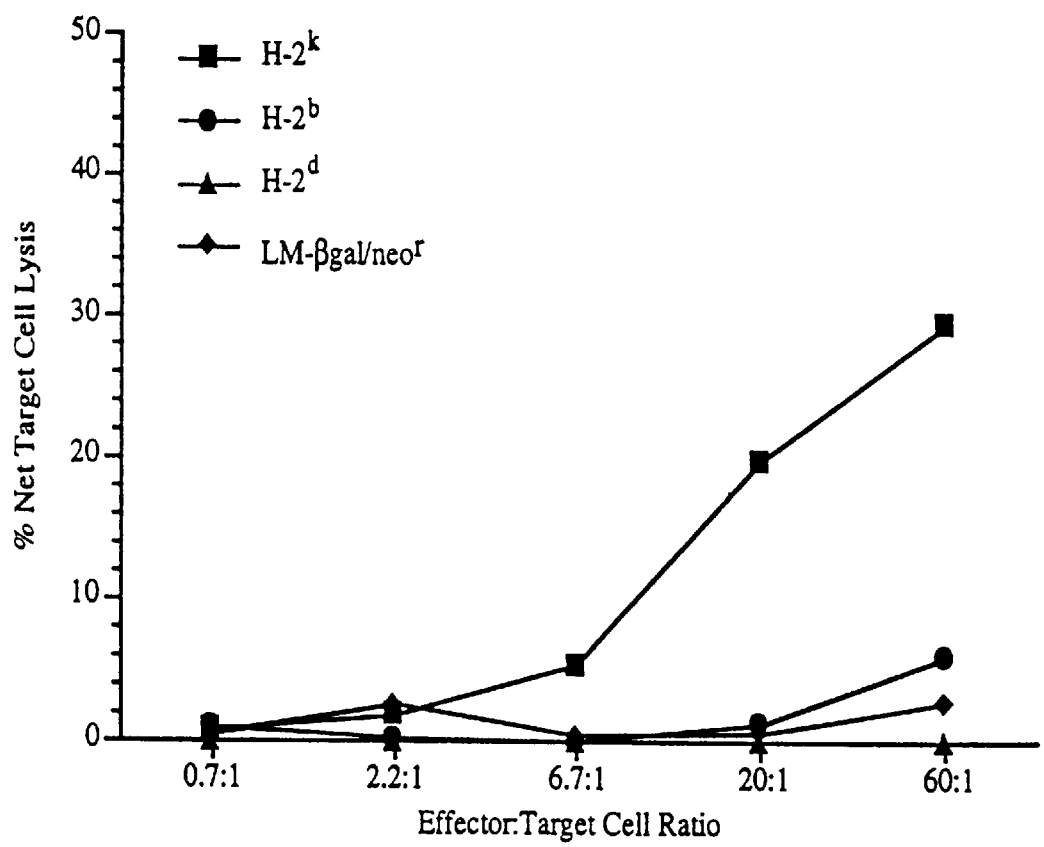
FIG. 10 is a graph showing that CTL response against HBV core antigen in the C3H/He CR mice are MHC class I restricted.

Effector cells obtained from C3H/He CR mice ($H2^k$) primed by i.m. administration of HBV core formulated vector are tested for their cytolytic activity using HB cAg retrovector-transduced LMTK-cells ($H-2^k$), HBcAg retrovector-transduced BL/6 cells ($H-2^b$), or HBcAg retrovector-transduced BC10ME cells ($H-2^d$) as targets in a chromium release assay. Results in FIG. 10 show that the effectors induced by immunization with HBcAg retrovector are $H-2^k$ MCH class I restricted because the effectors kill targets that present HBcAg in the context of $H-2^k$ but do not kill targets that present HBcAg in the context of $H-2^b$ or $H-2^d$.

From the above procedures, the stimulated effector cells by administered formulated HB core vector, were depleted of CD4 cells or CD8 cells by treatment with either anti-CD4 or anti-CD8 antibodies conjugated to magnetic beads.

Stimulated effector cells depleted of CD4 cells are isolated by immunomagnetic separation using Dynabeads (Dynal Inc., Skoyen, NO) as follows: a) restimulated spenocytes are incubated 30 minutes at 4° C. with monoclonal rat anti-L3T4 (Collaborative Biomedical Products, Becton Dickinson Labware, Bedford, Me.), b) cells are washed twice with DMEM containing 10% FCS and resuspended to $1\times10^7$ cells/ml in medium, c) approximately $75\mu l/1\times10^7$ cells/ml of prewashed Dynabeads coated with sheep anti-rat IgG (Dynal Inc., cat #M-450) are added to the cells, and $CD4^+$ cells are recovered magnetically. The remaining CD4-depleted cells are then tested for their cytolytic activity using LM core/$neo^r$ and B-gal/$neo^r$ as targets in a chromium release assay.

Figure 11A:
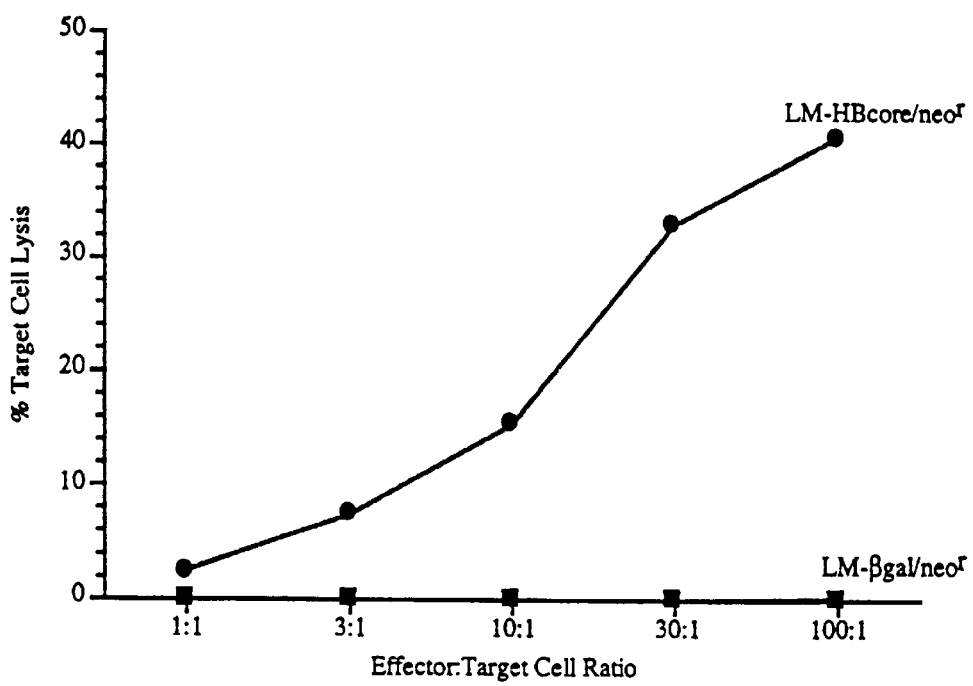
FIGS. 11A and B is a pair of graphs showing that CTL response against HBV core antigen in the C3H/He CR mice are CD4⁻ CD8⁺ cells.
Figure 11B:
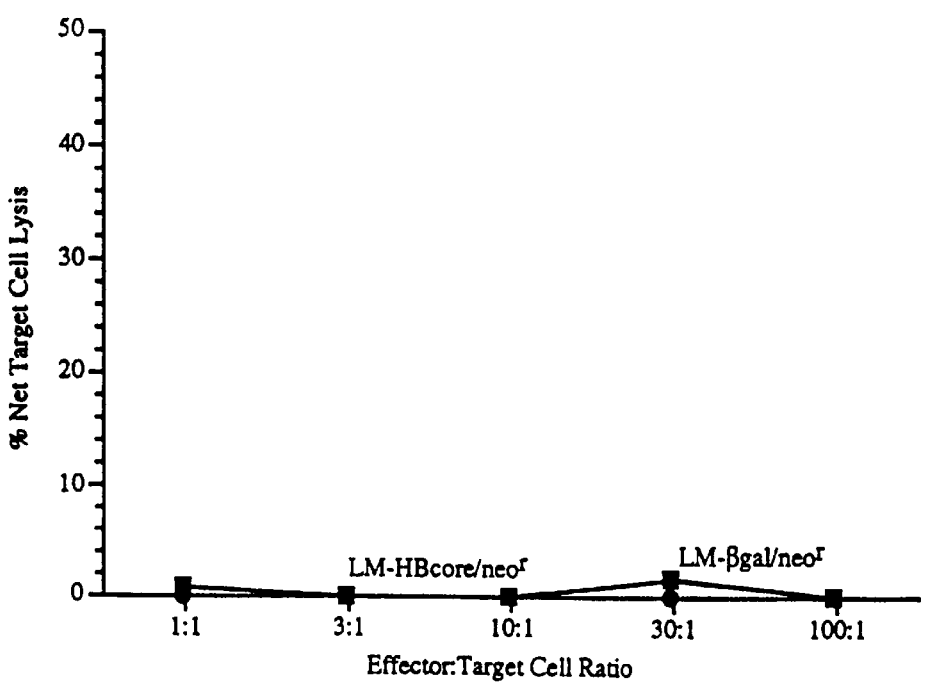
Figure 13:
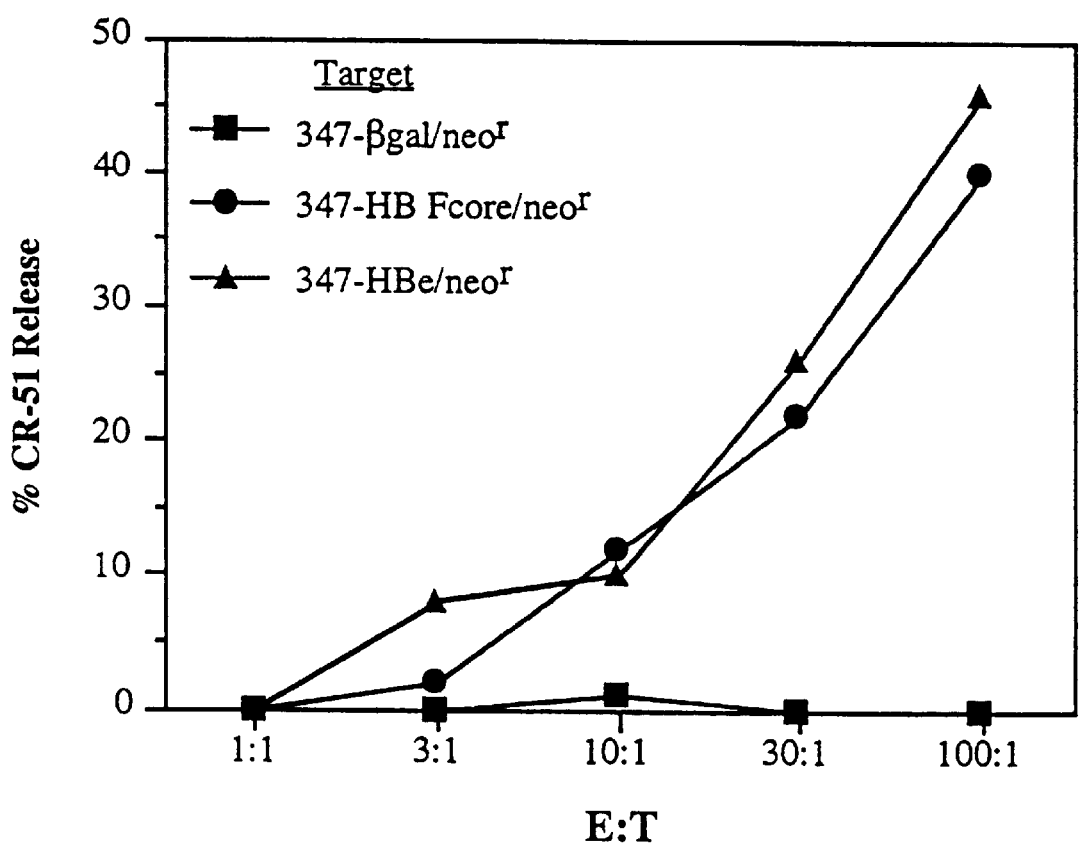
FIG. 13 is a graph showing induction of CTL responses against HBV core antigen and HBV e antigen in rhesus macaques after intramuscular injection of formulated HB Fcore/neo$^R$ vector.
Figure 14A:
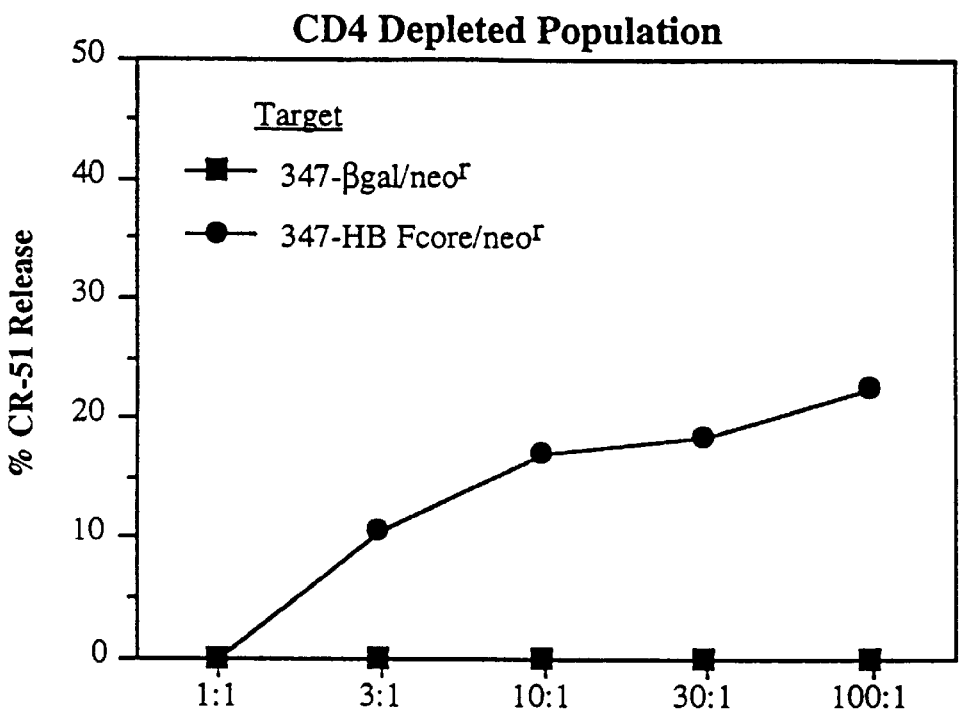
FIGS. 14A and B is a pair of graphs showing that CTL responses against HBV core antigen in the rhesus macaques are CD4⁻ CD8⁺ cells.
Figure 14B:
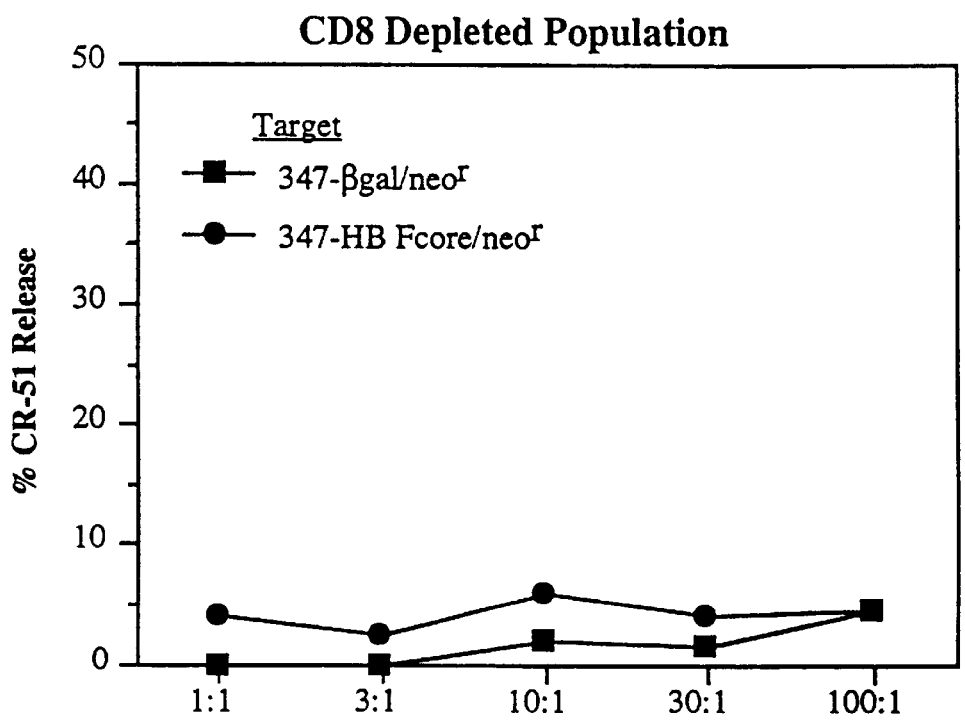

Stimulated effector cells depleted of CD8 cells are isolated by immunomagnetic separation using Dynabeads (Dynal Inc., Skoyen, NO) as follows: a) restimulated spenocytes are incubated 30 minutes at 4° C. with monoclonal rat anti-Lyt-2 (Collaborative Biomedical Products, Becton Dickinson Labware, Bedford, Me.), b) cells are washed twice with DMEM containing 10% FCS and resuspended to $1\times10^7$ cells/ml in medium, c) approximately $75 \mu l/1\times10^7$ cells/ml of prewashed Dynabeads coated with sheep anti-rat IgG (Dynal Inc., cat #M-450) are added to the cells, and $CD4^+$ cells are recovered magnetically. The remaining CD8-depleted cells are then tested for their cytolytic activity using i.m. core/$neo^r$ and B-gal/$neo^r$ as targets in a chromium release assay. Results shown in FIG. 11 show that the CTL effectors are CD8+, CD4–.

ii. HLA A2.1 and HLA A2.1/$K^b$ Transgenic Mice

Animals are sacrificed and the splenocytes ($3\times10^6$/ml) cultured in vitro with irradiated (10,000 rads) transduced Jurkat A2/$K^b$ cells or with peptide coated (Example 16) Jurkat A2/$K^b$ cells ($6\times10^4$/ml) in flasks (T-25, Corning, Corning, N.Y.). The remainder of the chromium release assay is performed as described in Example 15Ai, where the targets are transduced and non-transduced EL4 A2/$K^b$ and Jurkat A2/$K^b$ cells. Non-transduced cell lines are utilized as negative controls. The targets may also be peptide coated EL4 A2/$K^b$ cells as described in Example 16.

iii. Macaque CTL Assays

Blood samples are collected in heparinized tubes 14 days after each injection. The peripheral blood mononuclear cells (PBMCs) are then spun through a Ficoll-hypaque column at 2000 rpm for 30 minutes at room temperature. The PBMCs are stimulated in vitro with their autologous transduced LCL at a stimulator:effector ratio of 10:1 for 7–10 days. Culture medium consists of RPMI 1640 with 5% heat-inactivated fetal bovine serum (Hyclone, Logan, Utah), 1 mM sodium pyruvate, 10 mM HEPES, 2 mM L-glutamine, and 50 ugm/ml gentamycin. The resulting stimulated CTL effectors are tested for CTL activity against transduced and non-transduced autologous LCL in the standard chromium release assay.

iv. Chimpanzee and Human CTL Assays

Human PBMC are separated by Ficoll (Sigma, St. Louis, Mo.) gradient centrifugation. Specifically, cells are centrifuged at 3,000 rpm at room temperature for 5 minutes. The PBMCs are restimulated in vitro with their autologous transduced LCL, Example 10B, at a stimulator:effector ratio of 10:1 for 10 days. Culture medium consists of RPMI 1640 with prescreened lots of 5% heat-inactivated etal bovine serum, 1 mM sodium pyruvate and 50 $\mu$g/ml gentamycin. The resulting timulated CTL effectors are tested for CTL activity using transduced autologous LCL or HLA matched cells as targets in the standard chromium release assay, Example 12Ai. Since most patients have immunity to EBV, the non-transduced EBV-transformed B-cells (LCL) used as negative controls, will also be recognized as targets by EBV-specific CTL along with the transduced LCL. In order to reduce the high background due to killing of labeled target cells by EBV-specific CTL, it is necessary to add unlabeled non-transduced LCL to labeled target cells at a ratio of 50:1.

B. Detection of Humoral Immune Response

Humoral immune responses in mice specific for HBV core and e antigens are detected by ELISA. The ELISA protocol utilizes 100 $\mu$g/well of recombinant HBV core and recombinant HBV e antigen (Biogen, Geneva, Switzerland) to coat 96-well plates. Sera from mice immunized with cells or direct vector expressing HBV core or HBV e antigen are then serially diluted in the antigen-coated wells and incubated for 1 to 2 hours at room temperature. After incubation, a mixture of rabbit anti-mouse IgG1, IgG2a, IgG2b, and IgG3 with equivalent titers is added to the wells. Horseradish peroxidase ("HRP")-conjugated goat anti-rabbit antiserum is added to each well and the samples are incubated for 1 to 2 hours at room temperature. After incubation, reactivity is visualized by adding the appropriate substrate. Color will develop in wells that contain IgG antibodies specific for HBV core or HBV e antigen.

Using these procedures, it can be shown that IgG antibody to HBV core and e antigens can be induced in mice, FIG. 7. (The antibody titer is expressed as the reciprocal for the dilution required to yield 3 times the CD reading of pre-immunication sera.)

The isotype(s) of the humoral response in mice that have been immunized with HBV core or e retrovector are detected by an ELISA assay described above, with the following modification: sera from mice are serially diluted into the wells of a 96 well titer plate in which the wells have been coated with either recombinant core or e protein as described previously. The specific isotype is determined by incubation with one of the following rabbit anti-mouse antisera: IgG1, IgG2a, IgG2b, or IgG3. The assay is developed as previously described. Using this procedure, it can be shown that IgG2a antibody is preferentially induced in C3H/He (CR) mice immunicaed with formulated HBV core vector (6A3), and IgG1 antibody is preferentially induced in C3H/2699 He CR mice immunized with formulated HBV3 vector (5A2) (see FIG. 12).

C. T Cell Proliferation

Antigen induced T-helper activity resulting from two or three injections of direct vector preparations expressing HBV core or e antigen, is measured in vitro. Specifically, splenocytes from immunized mice are restimulated in vitro at a predetermined ratio with cells expressing HBV core or e antigen or with cells not expressing HBV core or e antigen as a negative control. After five days at 37° C. and 5% $CO_2$ in RPMI 1640 culture medium containing 5% FBS, 1.0 mM sodium pyruvate and $10^{-5}$ beta 2-mercaptoethanol, the supernatant is tested for IL-2 activity. IL-2 is secreted specifically by T-helper cells stimulated by HBV core or e antigen, and its activity is measured using the CTL clone, CTLL-2 (ATCC TIB 214). Briefly, the CTLL-2 clone is dependent on IL-2 for growth and will not proliferate in the absence of IL-2. CTLL-2 cells are added to serial dilutions of supernatant test samples in a 96-well plate and incubated at 37° C. and 5%, $CO_2$ for 3 days. Subsequently, 0.5 lCi $^3$H-thymidine is added to the CTLL-2 $^3$H-thymidine is incorporated only if the CTLL-2 cells proliferate. After an overnight incubation, cells are harvested using a PHD cell harvester (Cambridge Technology Inc., Watertown, Mass.) and counted in a Beckman beta counter. The amount of IL-2 in a sample is determined from a standard curve generated from a recombinant IL-2 standard obtained from Boehringer Mannheim (Indianapolis, Ind.).

D. Measurements of Cytokines from T Cells

As noted above, there are primarily two types of T-lymphocyte helper cells ($T_H$) designated $T_{H1}$ and $T_{H2}$. One method for measuring the type of $T_H$ induced is to determine the predominant isotype of the humoral immune response (see Example 15B) and thereby indirectly determine the type of $T_H$ response produced. Alternatively, the cytokine secretion pattern of the TH cell population from the mouse splenocytes restimulated in vitro as described above. After 5–7 days in culture, supernatant is tested for IL-2, IFN-$\gamma$, IL-4, and IL-10 using an ELISA assay that is specific for each cytokine (Pharmagen, San Diego, Calif.).

Yet another direct method for defining the type of TH induction is to measure the cytokine secretion pattern directly from the CD4$^+$ selected population of splenocytes restimulated in vitro, by reverse transcriptase-polymerase chain reaction (RT-PCR). Briefly, CD4$^+$ T cell populations are isolated by immunomagnetic separation using Dynabeads (Dynal Inc., Skoyen, NO) as follows: (a) restimulated spenocytes are incubated 30 minutes at 4° C. with monoclonal rat anti-L3T4 (Collaborative Biomedical Products, Becton Dickinson Labware, Bedford Me.), (b) cells are washed twice with DMEM containing 10% FCS and resuspended to 1×10$^7$ cells/ml in medium, (c) approximately 75 ml/1×10$^7$ cells/ml of prewashed Dynabeads coated with sheep anti-rat IgG (Dynal Inc., cat #M450) are added to the cells, and CD4$^+$ cells are recovered magnetically. Flow cytometry is used to determine concentration of CD4$^+$ T-cells. The RNA from the selected CD4$^+$ population is isolated by the method of Chomczynski and Sacchi (*Anal. Biochem.* 162:156, 1987). CD4$^+$ selected cells are added to a 4M guanidinium buffer and samples are treated with DNase 1 (Promega, Madison, Wis.) for 30 minutes at 37° C. cDNA is synthesized from 1 mg of RNA isolated from the CD4$^+$ selected cells. Briefly, 1 mg of RNA in 13 ml DEPC-treated $H_2O$ is primed by adding 1 ml (0.5 mg/ml) oligo-dT primer, 1 ml of Avian Myeloblastosis Virus (AMV) reverse transcriptase and 0.5 mM dNTP to the RNA and incubating at 42° C. for 1 hour. Approximately 20 ml of primed RNA is mixed with 30 ml of PCR reaction mixture containing 50 mM Tris-HCl, pH 9.0, 50 mM KCl, 2.5 mM $MgCl_2$, 0.1% (w/v) gelatin, 0.2 mM dNTP, 25 pM 5' and 3' oligonucleotide primers, and 2.5 U Taq polymerase (Promega, Madison Wis.). Aliquots are amplified in a DNA Thermocycler (Perkin-Elmer Corp., Norwalk, Conn.). A 40 cycle program is used in which each cycle consists of denaturation step at 94° C. for 1 min. and annealing/extension step at 55° C. (for IL-2 and g-IFN) or 65° C. for 2 min (IL-4 and IL-10). An aliquot of PCR product is then electrophoresed on a 2% agarose gel. The sequences of the cytokine specific primer pairs, 5' and 3', are as follows: IL-2; (SEQUENCE ID NO. 67)

5'-3': ACTCACCAGGATGCTCACAT
(SEQUENCE ID NO. 68)

5'-3': AGGTAATC-CATCTGTTCAGA IL-4;
(SEQUENCE ID NO. 69)

5'-3': CTTCCCCCTCTGTTCTTCCT
(SEQUENCE ID NO. 70)

5'-3': TTCCTGTCGAGCCGT-TTCAG IL-10;
(SEQUENCE ID NO. 71)

5'-3': ATGCCCCAAGCTGAGAACCAAGACCCA
(SEQUENCE ID NO. 72)

5'-3': TCTCAAGGGGCT-GGGTCAGCTATCCCA IFN-$\gamma$;
(SEQUENCE ID NO. 73)

5'-3': AGTTATATCTTGGCTTTTCA
(SEQUENCE ID NO. 74)

5'-3': ACCGAATAA-TTAGTCAGCTT

To verify PCR results (that IL-2 is IL-2, IL-4 is IL-4, IL-10 is IL-10 and IFN-γ is IFN-γ, PCR products are electrophoresed and transferred to Hybond-N nylon membranes (Amersham Corp., Arlington Heights, Ill.). Alternatively, PCR products are directly applied to nylon membranes by slot blotting. An oligonucleotide complementary to sequences within the region flanked by the PCR amplification primers is labeled at the 5' end by T4 polynucleotide kinase (Boehringer Mannheim Biochemicals, Indianapolis, Ind.) and $^{32}$P-γATP (7000 Ci/mM, ICN, Costa Mesa, Calif.) for use as a radioactive probe. Blots are then hybridized essentially as described by Sambrook et al. with probe for 4 hr., washed for 5 min. with 2×SSC and 0.1% SDS, followed by 0.2×SSC and 0.5% SDS, at ambient temperature. The blots were then exposed to X-ray film with intensifying screens at −80° C. overnight. The Sequences of the oligonucleotide probes 5' and 3' are: IL-2; (SEQUENCE ID NO. 75)

5'-3': AGCTAAATTFAGGCACTTCCTCCAG IL-4; (SEQUENCE ID NO. 76)

5'-3': CTCGGTG-CTCAGAGTCTTCTGCTCT IL-10; (SEQUENCE ID NO. 77)

5'-3': CAGGTGAAGAATGCCTTTAATAAGCTCCA-ACAGAAAGGCATCTACAAAGCCATGAGT-GACTTTGACATC γ-IFN; (SEQUENCE ID NO. 78)

5'-3': ATTTGGC-TCTGCATTATTTTTCTGT

Membranes are hybridized with radioactive probes and scanned using an AMBIS radioanalytic imaging system (Automated Microbiology Systems Inc., San Diego, Calif.).

Example 16

IDENTIFICATION OF IMMUNOGENIC DOMAINS OF HBV PRECORE/CORE

Cytotoxic T lymphocyte epitopes may be predicted utilizing the HLA A2.1 motif described by Falk et al., Nature 351:290, 1991). From this analysis, peptides are synthesized and used to identify CTL epitopes. These peptides are tested on individuals with acute hepatitis B infection or on HLA A2.1 or HLA $A_{2.1}/K^b$ transgenic mice. Effector cells from individuals with acute hepatitis B infection are stimulated in vitro with transduced autologous (Example 11Aiii) LCL and tested on autologous LCLs coated with the peptide. The chromium release assay is performed as described in Example 15Aiv, except that peptide is added at a final concentration of 1–100 μg/ml to non-transduced $Na_2{}^{51}CrO_4$-labeled LCL along with effector cells. The reaction is incubated 4–6 hours and a standard chromium release assay performed as described in Example 12Ai.

Effector cells from HLA A2.1 or HLA A2.1/$K^b$ transgenic mice are harvested and CTL assays performed as described in Example 15Aii. The peptide is added at a final concentration of 1–10 ug/ml to non-transduced $Na_2{}^{51}CrO_4$-labeled ELA A2/$K^b$ cells. These peptide coated cells are utilized as targets in a CTL assay.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A recombinant retrovirus which directs the expression of at least one immunogenic portion of a hepatitis B virus antigen wherein said antigen is selected from the group consisting of HBcAg, ORF 5, ORF 6, HBV pol, and HBxAg.

2. A vector construct which directs the expression of at least one immunogenic portion of a hepatitis B virus antigen wherein said antigen is selected from the group consisting of ORF 5, ORF 6, and HBV pol.

3. A vector construct which directs the co-expression of at least one immunogenic portion of a hepatitis B virus antigen and at least one immunogenic portion of a hepatitis C virus antigen.

4. The vector construct of claim 3 wherein said hepatitis C antigen is selected from the group consisting of core antigen C, antigen E1, antigen E2/NS1, antigen NS2, antigen NS3, antigen NS4, and antigen NS5.

5. A recombinant retrovirus which directs the expression of at least one immunogenic portion of two or more hepatitis B virus antigens selected from the group consisting of HBeAg, HBcAg, ORF 5, ORF 6, HBV pol, and HBxAg.

6. A recombinant retrovirus which directs the expression of at least one immunogenic portion of two or more hepatitis B virus antigens selected from the group consisting of HBcAg, HBsAg, S, Pre-S1, Pre-S2, ORF 5, ORF 6, HBV pol antigen, and HBxAg.

7. A vector construct which directs the expression of at least one immunogenic portion of two or more hepatitis B virus antigens selected from the group consisting of HBeAg, HbcAg, HbsAg, S, Pre-S1, Pre-S2, ORF 5, ORF 6, HBV pol, and HBxAg.

* * * * *

UNITED STATES PATENT AND TRADEMARK OFFICE
CERTIFICATE OF CORRECTION

PATENT NO. : 6,297,048 B1
APPLICATION NO. : 08/483511
DATED : October 2, 2001
INVENTOR(S) : Douglas J. Jolly et al.

It is certified that error appears in the above-identified patent and that said Letters Patent is hereby corrected as shown below:

Column 85, line 36, claim 2, after "A" and before "vector" insert --retroviral--

Column 85, line 39, claim 3, after "A" and before "vector" insert --retroviral--

Column 85, line 43, claim 4, after "A" and before "vector" insert --retroviral--

Column 86, line 39, claim 7, after "A" and before "vector" insert --retroviral--

Signed and Sealed this

Fifth Day of December, 2006

JON W. DUDAS
*Director of the United States Patent and Trademark Office*